US010625673B2

(12) United States Patent
Shibata et al.

(10) Patent No.: US 10,625,673 B2
(45) Date of Patent: *Apr. 21, 2020

(54) INFORMATION PROCESSING SYSTEM, INFORMATION PROCESSING METHOD, AND READABLE MEDIUM

(71) Applicant: PANASONIC INTELLECTUAL PROPERTY MANAGEMENT CO., LTD., Osaka (JP)

(72) Inventors: Tadashi Shibata, Osaka (JP); Toshiya Mori, Osaka (JP); Masanaga Tsuji, Osaka (JP); Nobuyuki Nakano, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 323 days.

This patent is subject to a terminal disclaimer.

(21) Appl. No.: 15/840,129

(22) Filed: Dec. 13, 2017

(65) Prior Publication Data

US 2018/0194280 A1    Jul. 12, 2018

(30) Foreign Application Priority Data

Dec. 16, 2016 (JP) .................................. 2016-244642

(51) Int. Cl.
*G01C 21/00* (2006.01)
*G01C 21/36* (2006.01)
(Continued)

(52) U.S. Cl.
CPC .............. *B60Q 9/00* (2013.01); *A61B 5/0205* (2013.01); *A61B 5/02416* (2013.01); *A61B 5/18* (2013.01); *B60K 28/02* (2013.01); *B60K 35/00* (2013.01); *B60R 16/0237* (2013.01); *B60W 50/14* (2013.01); *G01C 21/3415* (2013.01); *G01C 21/3484* (2013.01); *G01C 21/3658* (2013.01); *G01C 21/3676* (2013.01); *G01C 21/3697* (2013.01); *G06K 9/00335* (2013.01); *G06K 9/00845* (2013.01); *G08G 1/167* (2013.01);
(Continued)

(58) Field of Classification Search
CPC ......... B60Q 9/00; B60W 30/00; B60W 30/08; B60W 50/10; B60R 16/023; G05D 1/00; G01P 13/00; G01C 21/00; G01C 21/36
See application file for complete search history.

(56) References Cited

U.S. PATENT DOCUMENTS 9,739,634 B2 * 8/2017 Trivedi ................ H04L 67/306
10,241,509 B1 * 3/2019 Fields ................. A61B 5/4094
(Continued)

FOREIGN PATENT DOCUMENTS

JP    2005-067483    3/2005

*Primary Examiner* — Yuri Kan
(74) *Attorney, Agent, or Firm* — Greenblum & Bernstein, P.L.C.

(57) ABSTRACT

An information processing system is provided with a modeling unit. The modeling unit models, based on a degree of similarity among individual travel histories of a plurality of drivers, individual travel histories of at least one or more drivers from among the individual travel histories of the plurality of drivers to construct a driver model indicating a relationship between conditions of the at least one or more drivers and travel environments of at least one or more vehicles.

11 Claims, 48 Drawing Sheets

(51) Int. Cl.
*B60W 50/10* (2012.01)
*B60Q 9/00* (2006.01)
*G01C 21/34* (2006.01)
*A61B 5/18* (2006.01)
*A61B 5/024* (2006.01)
*B60R 16/023* (2006.01)
*B60K 28/02* (2006.01)
*A61B 5/0205* (2006.01)
*G08G 1/16* (2006.01)
*B60K 35/00* (2006.01)
*B60W 50/14* (2020.01)
*G06K 9/00* (2006.01)
*A61B 5/00* (2006.01)
*A61B 5/11* (2006.01)
*B60W 50/00* (2006.01)

(52) U.S. Cl.
CPC ............ *A61B 5/1116* (2013.01); *A61B 5/1118* (2013.01); *A61B 5/4812* (2013.01); *A61B 5/7264* (2013.01); *B60W 2050/0029* (2013.01)

(56) References Cited

U.S. PATENT DOCUMENTS

| | | | |
|---|---|---|---|
| 2014/0142867 A1* | 5/2014 | Shirakata | G01P 13/00 702/33 |
| 2014/0316702 A1* | 10/2014 | Cardonha | G01C 21/20 701/537 |
| 2015/0029014 A1* | 1/2015 | Bande Martinez | G08B 21/06 340/439 |
| 2015/0120086 A1* | 4/2015 | Endo | B60W 30/08 701/1 |
| 2015/0166058 A1* | 6/2015 | Mizutani | B60W 50/14 701/1 |
| 2019/0283773 A1* | 9/2019 | Mori | G06N 3/08 |

* cited by examiner

FIG. 16

| Travel environment | Approach to merging lane | | | There is a low-speed vehicle ahead | | | ... |
|---|---|---|---|---|---|---|---|
| Behavior | Deceleration | Acceleration | Lane change | Follow | Overtake | Lane change | ... |
| Driver x | 3 | 1 | 5 | 2 | 2 | 1 | ... |
| Driver y | 9 | 1 | 2 | 0 | 0 | 0 | ... |

FIG. 17

| | Travel environment | Approach to merging lane | | | There is a low-speed vehicle ahead | | | ... |
|---|---|---|---|---|---|---|---|---|
| | Behavior | Deceleration | Acceleration | Lane change | Follow | Overtake | Lane change | ... |
| Model A | Driver a | 3 | 1 | 5 | 1 | 1 | 5 | ... |
| | Driver b | 4 | 2 | 7 | 2 | 0 | 3 | ... |
| | Driver c | 3 | 2 | 2 | 1 | 2 | 8 | ... |
| Model B | Driver d | 5 | 2 | 2 | 5 | 2 | 2 | ... |
| | Driver e | 7 | 2 | 2 | 5 | 0 | 3 | ... |
| | Driver f | 5 | 2 | 5 | 4 | 1 | 1 | ... |
| | ... | ... | ... | ... | ... | ... | ... | ... |

FIG. 18

| Travel environment | Approach to merging lane | | | There is a low-speed vehicle ahead | | | ... |
|---|---|---|---|---|---|---|---|
| Behavior | Deceleration | Acceleration | Lane change | Follow | Overtake | Lane change | ... |
| Model A | 3.3 | 1.7 | 4.6 | 1.3 | 1 | 5.3 | ... |
| Model B | 5.7 | 2 | 3 | 4.7 | 1 | 2 | ... |

FIG. 19

| Travel environment | Approach to merging lane | There is a low-speed vehicle ahead | ... |
|---|---|---|---|
| Model A | Lane change | Lane change | ... |
| Model B | Deceleration | Follow | ... |

FIG. 20

| Travel environment | Approach to merging lane | | | There is a low-speed vehicle ahead | | | ... |
|---|---|---|---|---|---|---|---|
| Behavior | Deceleration | Acceleration | Lane change | Follow | Overtake | Lane change | ... |
| Driver a | 3 | 1 | 5 | 1 | 1 | 5 | ... |
| Driver b | 4 | 2 | 7 | 2 | 0 | 3 | ... |
| Driver c | 3 | 2 | 2 | 1 | 2 | 8 | ... |
| Driver d | 5 | 2 | 2 | 5 | 2 | 2 | ... |
| Driver e | 7 | 2 | 2 | 5 | 0 | 3 | ... |
| Driver f | 5 | 2 | 5 | 4 | 1 | 1 | ... |
| ... | ... | ... | ... | ... | ... | ... | ... |

Model of driver y

FIG. 21

| Travel environment | Approach to merging lane | | | There is a low-speed vehicle ahead | | | ... |
|---|---|---|---|---|---|---|---|
| Behavior | Deceleration | Acceleration | Lane change | Follow | Overtake | Lane change | ... |
| Model of driver y | 5 | 2 | 2 | 3.7 | 1.3 | 4.3 | ... |

FIG. 22

| | Behavior | Fellow passenger | Speed | Steering wheel | Brake | Accelerator | ... | Number of times |
|---|---|---|---|---|---|---|---|---|
| Driver x | Lane change | None | 8 | 4 | 6 | 8 | ... | 80 |
| | | 1 adult and 2 children | 3 | 3 | 4 | 3 | ... | 40 |
| | | 1 adult | 5 | 7 | 5 | 5 | ... | 60 |
| | | ... | ... | ... | ... | ... | ... | ... |
| | Overtake | ... | ... | ... | ... | ... | ... | ... |
| | ... | ... | ... | ... | ... | ... | ... | ... |
| Driver y | Lane change | ... | ... | ... | ... | ... | ... | ... |
| | Overtake | ... | ... | ... | ... | ... | ... | ... |
| | ... | ... | ... | ... | ... | ... | ... | ... |
| ... | ... | ... | ... | ... | ... | ... | ... | ... |

FIG. 27

Driver x

| History | Behavior | Environmental parameters ||||||||||||||||| |
|---|---|---|---|---|---|---|---|---|---|---|---|---|---|---|---|---|---|
| | | Host vehicle information | Front vehicle information || Adjacent lane information |||||||| Merging lane information ||| Location information || |
| | | | | | Adjacent following vehicle || Adjacent leading vehicle |||| | | | | | | |
| | | Va | Vba | DRba | RSb | Vca | Dca | Rca | Vda | Dda | Rda | DRda | Vma | Dma | Rma | Travel lane | Distance to merging point | |
| (a) | Deceleration | 4 | 1 | 2 | 5 | 4 | 2 | 2 | 3 | 3 | 1 | 3 | 0 | 0 | 0 | 2 | 0 | ⋮ |
| (b) | Lane change | 3 | 2 | 5 | 4 | 2 | 2 | 1 | 0 | 0 | 0 | 10 | 1 | 2 | 3 | 1 | 4 | ⋮ |
| (c) | Deceleration | 3 | 2 | 5 | 4 | 3 | 1 | 3 | 3 | 1 | 3 | 2 | 2 | 2 | 2 | 1 | 4 | ⋮ |
| ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ |

| Behavior | Environmental parameters | | | | | | | | | | | | | |
|---|---|---|---|---|---|---|---|---|---|---|---|---|---|---|
| | Host vehicle information | Leading vehicle information | | | Adjacent lane information | | | | | | | Merging lane information | | Location information |
| | | | | | Adjacent following vehicle | | | Adjacent leading vehicle | | | | | | |
| | $V_a$ | $V_{ba}$ | $DR_{ba}$ | $RS_b$ | $V_{ca}$ | $D_{ca}$ | $R_{ca}$ | $V_{da}$ | $D_{da}$ | $R_{da}$ | $DR_{da}$ | $V_{ma}$ $D_{ma}$ $R_{ma}$ | Travel lane | Distance to merging point |
| ??? | 3 | 3 | 5 | 4 | 1 | 2 | 1 | 0 | 0 | 0 | 9 | 1  2  3 | 1 | 4  ... |

(b)

| History | Behavior | Environmental parameters | | | | | | | | | | | | | |
|---|---|---|---|---|---|---|---|---|---|---|---|---|---|---|---|
| | | Host vehicle information | Leading vehicle information | | | Adjacent lane information | | | | | | | Merging lane information | | Location information |
| | | | | | | Adjacent following vehicle | | | Adjacent leading vehicle | | | | | | |
| | | $V_a$ | $V_{ba}$ | $DR_{ba}$ | $RS_b$ | $V_{ca}$ | $D_{ca}$ | $R_{ca}$ | $V_{da}$ | $D_{da}$ | $R_{da}$ | $DR_{da}$ | $V_{ma}$ $D_{ma}$ $R_{ma}$ | Travel lane | Distance to merging point |
| (d) | Deceleration | 4 | 1 | 2 | 5 | 4 | 2 | 2 | 3 | 3 | 1 | 3 | 0  0  0 | 1 | 0  ... |
| (e) | Lane change | 3 | 2 | 5 | 4 | 2 | 2 | 1 | 0 | 0 | 0 | 10 | 1  2  3 | 1 | 4  ... |
| (f) | Deceleration | 3 | 2 | 5 | 4 | 3 | 1 | 3 | 3 | 1 | 3 | 2 | 2  2  2 | 1 | 4  ... |
| ... | ... | ... | ... | ... | ... | ... | ... | ... | ... | ... | ... | ... | ... ... ... | ... | ... |

FIG. 37

Vehicle speed DB

| Driver ID | Environmental parameters | | | | | | | ... | Vehicle speed [km/h] |
|---|---|---|---|---|---|---|---|---|---|
| | ① | ② | ③ | ④ | ⑤ | ⑥ | ⑦ | | |
| 0001 | 0.1 | 0.2 | 0.5 | 0.0 | 1.0 | 0.0 | 0.3 | ... | 70 |
| 0002 | 0.5 | 0.1 | 0.4 | 0.1 | 0.2 | 0.5 | 0.0 | ... | 68 |
| 0003 | 1.0 | 0.5 | 0.0 | 0.0 | 0.0 | 0.1 | 0.7 | ... | 30 |
| 0004 | 1.0 | 1.0 | 0.1 | 0.2 | 0.5 | 0.0 | 0.1 | ... | 52 |
| ... | | | | | | | | | |

Inter-vehicular distance DB

| Driver ID | Environmental parameters | | | | | | | ... | Inter-vehicular distance DB [m] |
|---|---|---|---|---|---|---|---|---|---|
| | ① | ② | ③ | ④ | ⑤ | ⑥ | ⑦ | | |
| 0001 | 0.1 | 0.2 | 0.5 | 0.0 | 1.0 | 0.0 | 0.3 | ... | 60 |
| 0002 | 0.5 | 0.1 | 0.4 | 0.1 | 0.2 | 0.5 | 0.0 | ... | 100 |
| 0003 | 1.0 | 0.5 | 0.0 | 0.0 | 0.0 | 0.1 | 0.7 | ... | 32 |
| 0004 | 1.0 | 1.0 | 0.1 | 0.2 | 0.5 | 0.0 | 0.1 | ... | 90 |
| ... | | | | | | | | | |

FIG. 38

Acceleration/deceleration rate pattern DB

| Driver ID | Environmental parameters | | | | | | | | Pattern |
|---|---|---|---|---|---|---|---|---|---|
| | ① | ② | ③ | ④ | ⑤ | ⑥ | ⑦ | ... | |
| 0001 | 0.1 | 0.2 | 0.5 | 0.0 | 1.0 | 0.0 | 0.3 | ... | A |
| 0002 | 0.5 | 0.1 | 0.4 | 0.1 | 0.2 | 0.5 | 0.0 | ... | A |
| 0003 | 1.0 | 0.5 | 0.0 | 0.0 | 0.0 | 0.1 | 0.7 | ... | C |
| 0004 | 1.0 | 1.0 | 0.1 | 0.2 | 0.5 | 0.0 | 0.1 | ... | B |

| Vehicle ID | Situation description parameter (characteristic amount) | | | | | | | | Depression amount (behavior) |
|---|---|---|---|---|---|---|---|---|---|
| | Vehicle type ID | Acceleration rate [m/s²] | Vehicle speed [km/h] | Road surface condition(*) | Gradient [%] | Wind speed [m/s] | Load [kg] | ... | |
| A | 001 | 0.5 | 10 | 1 | 3.0 | 5.0 | 60 | | 0.5 |
| A | 001 | 0.3 | 15 | 0 | 0 | 4.0 | 120 | | 0.3 |
| B | 003 | 0.1 | 30 | 0 | -0.5 | 0.0 | 150 | | 0.7 |
| B | 003 | 0.1 | 31 | 2 | 0.3 | 1.0 | 100 | | 0.1 |

*Road condition ... 0: not slippery, 1: wet, a little slippery, 2: icy, slippery

FIG. 46

| Driver ID | Environmental parameters ||||| Risk |
| --- | --- | --- | --- | --- | --- | --- |
| | Vehicle speed | Inter-vehicular distance with leading vehicle | Relative change rate of leading vehicle | Inter-vehicular distance with leading vehicle on left side | Relative change rate of leading vehicle on left side | |
| 0001 | 60 | 20 | 1.5 | 50 | -0.3 | Rear-end collision |
| 0001 | 50 | — | — | 60 | 0 | lane departure |
| 0001 | 40 | 50 | 1.5 | 30 | 0 | Minor collision with following vehicle on right side |
| | | | | | ... | |

FIG. 49

| Travel environment | Approach to merging lane (lane change) | | | Approach to urban area (traffic jam) | | | | | | Dangerous object ahead | |
|---|---|---|---|---|---|---|---|---|---|---|---|
| Driver condition | Gaze to meter | High stress | Unsafe posture | Visual distraction | Doze | Loss of consciousness | High heart rate | High stress | Discomfort | Perception delay | High heart rate |
| Driver ID:01 | 5 | 10 | 2 | 7 | 3 | 1 | 7 | 10 | 1 | 4 | 7 |
| Driver ID:02 | 4 | 0 | 1 | 5 | 2 | 0 | 5 | 2 | 2 | 5 | 10 |
| Driver ID:03 | 1 | 4 | 6 | 5 | 1 | 3 | 1 | 1 | 1 | 2 | 1 |
| Driver ID:04 | 4 | 2 | 10 | 9 | 0 | 0 | 0 | 0 | 4 | 0 | 0 |
| Driver ID:05 | 5 | 5 | 3 | 10 | 1 | 1 | 2 | 2 | 3 | 3 | 1 |

FIG. 50

| | Environmental parameters(travel environment) | | | | | | Condition parameters(driver condition) | | | | | | |
|---|---|---|---|---|---|---|---|---|---|---|---|---|---|
| | Inter-vehicular distance | Speed | Degree of lane departure | Spot | Time | Ambient temperature | Visual distraction | Drowsiness | Stress | Heart rate | Level of discomfort | Unsafe posture | Loss of consciousness |
| Driver ID: 01 | 3 | 5 | 0 | 4 | 6 | 2 | 1 | 5 | 2 | 5 | 6 | 1 | 0 |
| | 10 | 1 | 3 | 3 | 1 | 1 | 1 | 8 | 1 | 3 | 4 | 2 | 0 |
| | 5 | 5 | 7 | 8 | 3 | 6 | 8 | 2 | 2 | 5 | 3 | 4 | 2 |
| | 1 | 9 | 1 | 7 | 8 | 9 | 9 | 6 | 1 | 2 | 4 | 7 | 0 |
| | ... | ... | ... | ... | ... | ... | ... | ... | ... | ... | ... | ... | ... |
| Driver ID: 02 | 1 | 1 | 3 | 9 | 6 | 1 | 1 | 1 | 6 | 8 | 1 | 8 | 1 |
| | 4 | 3 | 1 | 0 | 3 | 2 | 2 | 0 | 3 | 1 | 2 | 3 | 3 |
| | 10 | 9 | 5 | 0 | 7 | 6 | 5 | 3 | 7 | 2 | 7 | 2 | 0 |
| | 8 | 2 | 9 | 1 | 1 | 3 | 9 | 9 | 1 | 9 | 3 | 6 | 2 |
| | ... | ... | ... | ... | ... | ... | ... | ... | ... | ... | ... | ... | ... |
| ... | ... | ... | ... | ... | ... | ... | ... | ... | ... | ... | ... | ... | ... |

FIG. 53

| | Behavior | Environmental parameters(travel environment) | | | | | | Condition parameters(driver condition) | | | | | |
|---|---|---|---|---|---|---|---|---|---|---|---|---|---|
| | | Inter-vehicular distance | Speed | Degree of lane departure | Spot | Time | Ambient temperature | Visual distraction | Drowsi-ness | Stress | Heart rate | Level of discomfort | Unsafe posture | Loss of consciousness |
| Driver ID: 01 | Acceleration | 3 | 5 | 0 | 4 | 6 | 2 | 1 | 5 | 2 | 5 | 6 | 1 | 0 |
| | Deceleration | 10 | 1 | 3 | 3 | 1 | 1 | 1 | 8 | 1 | 3 | 4 | 2 | 0 |
| | Overtake | 5 | 5 | 7 | 8 | 3 | 6 | 8 | 2 | 2 | 5 | 3 | 4 | 2 |
| | Lane change | 1 | 9 | 1 | 7 | 8 | 9 | 9 | 6 | 1 | 2 | 4 | 7 | 0 |
| | ... | ... | ... | ... | ... | ... | ... | ... | ... | ... | ... | ... | ... | ... |
| Driver ID: 02 | Acceleration | 1 | 1 | 3 | 9 | 6 | 1 | 1 | 1 | 6 | 8 | 1 | 8 | 1 |
| | Deceleration | 4 | 3 | 1 | 0 | 3 | 2 | 2 | 0 | 3 | 1 | 2 | 3 | 3 |
| | Overtake | 10 | 9 | 5 | 0 | 7 | 6 | 5 | 3 | 7 | 2 | 7 | 2 | 0 |
| | Lane change | 8 | 2 | 9 | 1 | 1 | 3 | 9 | 9 | 1 | 9 | 3 | 6 | 2 |
| | ... | ... | ... | ... | ... | ... | ... | ... | ... | ... | ... | ... | ... | ... |
| ... | ... | ... | ... | ... | ... | ... | ... | ... | ... | ... | ... | ... | ... | ... | ically recognize the operating state of autonomous steering control or autonomous acceleration/deceleration control, in the autonomous steering control or the autonomous acceleration/deceleration control of a host vehicle.

INFORMATION PROCESSING SYSTEM, INFORMATION PROCESSING METHOD, AND READABLE MEDIUM

TECHNICAL FIELD

The present invention relates to an information processing system, an information processing method, and a program for processing information pertaining to a vehicle.

BACKGROUND ART

Recently, there have been proposed various technologies relating to a vehicle which can be driven in a manual driving mode in which a driver oneself drives the vehicle or in an autonomous driving mode in which a portion of or all of driving operations are autonomously performed, or technologies relating to a fully automated self-driving vehicle, based on a surrounding situation of the vehicle or a travel state (for example, the speed of the vehicle or control information such as steering, acceleration, braking, turn signal indicator, or actuator) of the vehicle, and these technologies have been put into practical use.

For example, PTL 1 discloses a travel control device configured to allow a driver to visually recognize the operating state of autonomous steering control or autonomous acceleration/deceleration control, in the autonomous steering control or the autonomous acceleration/deceleration control of a host vehicle.

CITATION LIST

Patent Literature

PTL 1: Unexamined Japanese Patent Publication No. 2005-67483

SUMMARY OF THE INVENTION

Technical Problem

However, the travel control device (that is, an information processing system) disclosed in PTL 1 entails a problem of being difficult to estimate a condition of a driver.

In view of this, the present invention provides an information processing system or the like capable of estimating a condition of a driver.

Solution to Problem

An information processing system according to one aspect of the present invention is an information processing system including at least one processor, wherein the at least one processor models, based on a degree of similarity among individual travel histories of a plurality of drivers, individual travel histories of at least one or more drivers from among the individual travel histories of the plurality of drivers to construct a driver model indicating a relationship between driver conditions of the at least one or more drivers and travel environments of at least one or more vehicles.

According to this configuration, the driver model indicating the relationship between a driver condition of a driver and a travel environment of a vehicle is constructed, whereby a condition of a driver can be estimated from a travel environment of a vehicle by using this driver model.

For example, the information processing system may further include an environment acquisition unit that acquires a travel environment of a vehicle driven by a driver to be estimated, and the at least one processor may estimate a driver condition associated with the travel environment acquired by the environment acquisition unit, from among the driver conditions of the at least one or more drivers, in the driver model as a condition of the driver to be estimated.

The information processing system may also include a notification unit that provides notification to the driver to be estimated, wherein the at least one processor may determine whether or not an estimated condition of the driver to be estimated is dangerous, and when determining that the estimated condition of the driver to be estimated is dangerous, the at least one processor may execute a danger avoidance process for causing the notification unit to provide information for avoiding danger to the driver to be estimated.

According to this configuration, if the estimated condition of the driver to be estimated is dangerous, information for avoiding the danger is presented to the driver, whereby the danger can be avoided in advance.

In addition, the at least one processor may estimate a direction of a gaze of the driver to be estimated as the condition of the driver to be estimated, and when an estimated gaze is not turned to an advancing direction of the vehicle driven by the driver to be estimated, the at least one processor may determine that the estimated gaze is dangerous, and execute the danger avoidance process to cause the notification unit to issue a warning to the driver to be estimated.

Thus, visual distraction of the driver can be avoided in advance, for example.

In addition, the at least one processor may estimate an intensity level of drowsiness of the driver to be estimated as the condition of the driver to be estimated, and when an estimated intensity level of drowsiness is higher than a threshold, the at least one processor may determine that the estimated intensity level of drowsiness is dangerous, and execute the danger avoidance process to cause the notification unit to play predetermined music.

Thus, the driver can be prevented from dozing off in advance.

In addition, the notification unit may provide a display of a travel route of the vehicle driven by the driver to be estimated, and the at least one processor may estimate a heart rate of the driver to be estimated as the condition of the driver to be estimated, and when an estimated heart rate is higher than a threshold, the at least one processor may determine that the estimated heart rate is dangerous, and execute the danger avoidance process to cause the notification unit to change the travel route of the vehicle to a travel route for avoiding danger.

Thus, an elevation of the heart rate of the driver can be suppressed in advance by making a detour around a road having heavy traffic, for example.

In addition, the at least one processor may estimate a posture of the driver to be estimated as the condition of the driver to be estimated, and when an estimated posture is a predetermined posture, the at least one processor may determine that the estimated posture is dangerous, and execute the danger avoidance process to cause the notification unit to issue a warning to the driver to be estimated.

Thus, a dangerous posture of the driver, such as a posture while the driver searches a baggage on a passenger seat, can be avoided in advance, for example.

Further, in constructing the driver model, the at least one processor may construct the driver model indicating a relationship among the driver conditions of the at least one or more drivers, the travel environments of the at least one or more vehicles, and behaviors of the at least one or more vehicles, and estimate a behavior of a vehicle associated with the travel environment of the vehicle driven by the driver to be estimated and the condition of the driver to be estimated in the driver model as a behavior of the vehicle driven by the driver to be estimated.

Thus, a behavior of the vehicle is estimated not merely based on a travel environment of the vehicle but based on the travel environment and a condition of the driver, whereby a more accurate behavior of the vehicle can be estimated.

Note that those comprehensive or specific aspects may be implemented by a system, a method, an integrated circuit, a computer program, or a non-transitory computer-readable recording medium such as a CD-ROM, or may be implemented by any combination of the system, the method, the integrated circuit, the computer program, and the recording medium.

Advantageous Effect of Invention

According to the present invention, a condition of a driver can be estimated.

BRIEF DESCRIPTION OF DRAWINGS

FIG. 16 is a diagram illustrating one example of a travel history.

FIG. 17 is a diagram illustrating a method for constructing a clustering-type driver model.

FIG. 18 is a diagram illustrating one example of the constructed clustering-type driver model.

FIG. 19 is a diagram illustrating another example of the constructed clustering-type driver model.

FIG. 20 is a diagram illustrating a method for constructing an individually-adapted-type driver model.

FIG. 21 is a diagram illustrating one example of the constructed individually-adapted-type driver model.

FIG. 22 is a diagram illustrating one example of a driving characteristic model.

FIG. 27 is a diagram illustrating one example of a travel history.

FIG. 28 is a diagram illustrating a method for using a driver model according to a present modification.

FIG. 37 is a diagram illustrating one example of information stored in a storage unit in the fifth exemplary embodiment.

FIG. 38 is a diagram illustrating one example of another information stored in the storage unit in the fifth exemplary embodiment.

FIG. 43 is a diagram illustrating vehicle characteristics according to one exemplary embodiment of the present invention.

FIG. 46 is a diagram illustrating one example of a danger travel history stored in a danger travel history storage unit in an information processing system according to the modification of one exemplary embodiment of the present invention.

FIG. 49 is a diagram illustrating one example of a travel history in the sixth exemplary embodiment.

FIG. 50 is a diagram illustrating another example of a travel history in the sixth exemplary embodiment.

FIG. 53 is a diagram illustrating one example of a travel history in the modification of the sixth exemplary embodiment.

DESCRIPTION OF EMBODIMENTS

Figure 1:
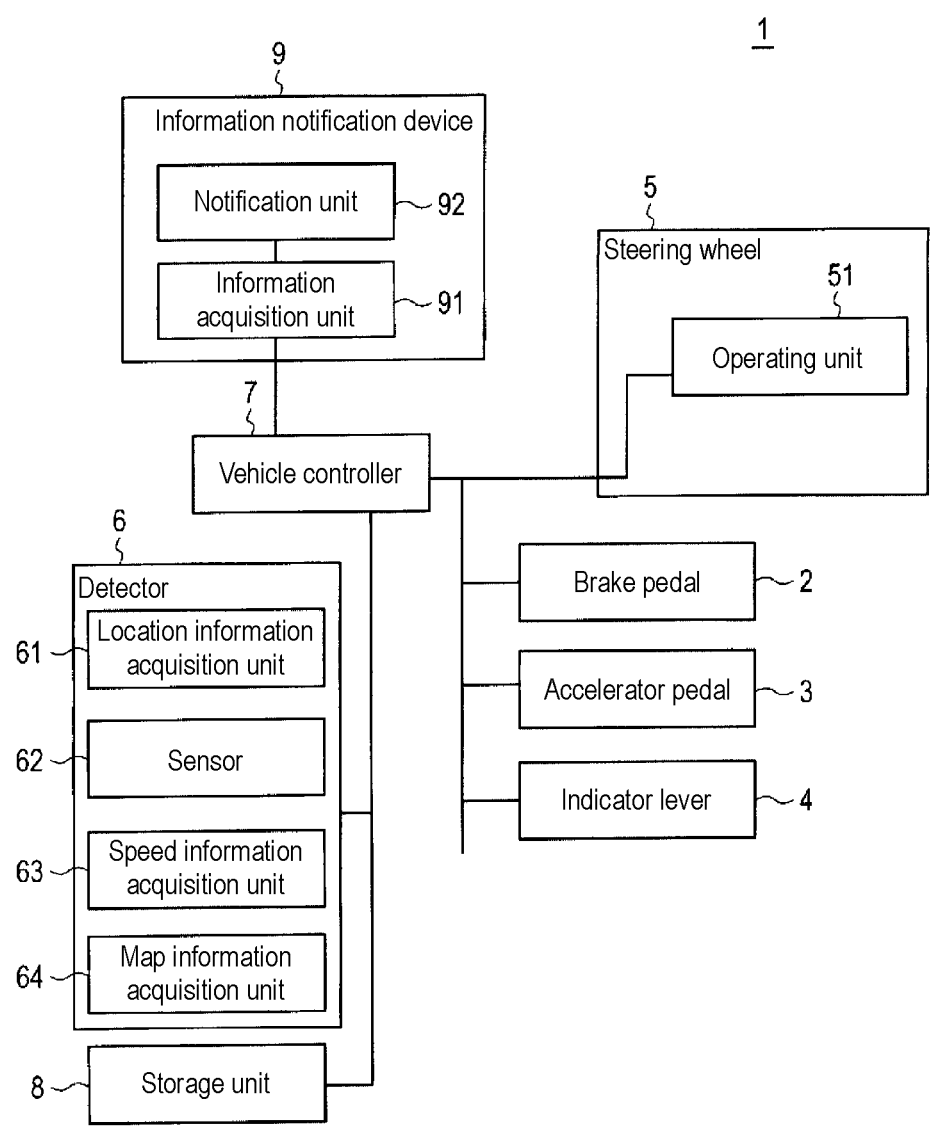
FIG. 1 is a block diagram illustrating a configuration of a main part of a vehicle including an information notification device according to a first exemplary embodiment of the present invention.

Hereinafter, exemplary embodiments of the present invention will be described in detail with reference to the drawings. First to third exemplary embodiments describe an information notification device, an information notification method, or an information notification program capable of appropriately transmitting information so as to enable comfortable autonomous driving in which a vehicle operation and a driver's operation are difficult to be incompatible with each other. Fourth and fifth exemplary embodiments describe an information processing system, an information processing method, and a program capable of estimating a driving action suitable for a driver. A sixth exemplary embodiment describes an information processing system, an information processing method, and a program for estimating a condition of a driver and performing a process according to the estimated condition.

Note that each of the exemplary embodiments described below is only illustrative, and does not limit the present invention. Specifically, the following exemplary embodiments provide a comprehensive, specific example of the present invention. Numerical values, shapes, materials, constituent elements, arrangement positions and connection modes of the constituent elements, steps, and order of the steps, for example, illustrated in the following exemplary embodiments are merely examples, and therefore are not intended to limit the present invention. Furthermore, among constituent elements in the following exemplary embodiments, constituent elements not recited in the independent claim indicating the broadest concept are described as optional constituent elements.

It should be noted that each of the diagrams is schematic, and is not necessarily strictly accurate. Further, in each diagram, the same components are denoted by the same reference marks.

(First Exemplary Embodiment)

Firstly, knowledge which has led up to an information processing device according to the first exemplary embodiment will be described.

During autonomous driving (including both full autonomous driving and limited autonomous driving), a driver relies on a vehicle to autonomously drive, so that a trust relationship between the vehicle and the driver is significantly important, and it is necessary to transmit appropriate information between the vehicle and the driver (occupant). In PTL 1, a driver is notified of only a current operating state.

There arises a first problem in which the driver has a large amount of anxiety, if he/she is notified of only a current behavior (operating state or control content) of the vehicle and not notified of a behavior that the vehicle is about to perform (for example, a control content such as a lane change, acceleration, or deceleration, which is about to be performed by the vehicle particularly before merging, before entering an intersection, when an emergency vehicle is close to the vehicle, or when other vehicles around the vehicle are about to do or have done a certain action), during autonomous driving.

In addition, there is a second problem as follows. During full autonomous driving, it is highly likely that the driver takes actions other than monitoring driving. Therefore, when only the current operating state is suddenly displayed, the driver is unable to recognize the current surrounding situation of the vehicle or the travel state of the vehicle, and even if the driver tries to issue a driving instruction by his/her own will, he/she is unable to promptly respond, and he/she cannot smoothly give an instruction to the vehicle.

There is also a third problem in which the driver is notified of only the current operating state, and even if the driver tries to directly and manually drive the vehicle, the driving mode is not promptly switched from the autonomous driving to the manual driving.

In addition, there is a fourth problem as follows. Even if the vehicle takes the same action by the driver or an occupant, a timing of the action or an operation amount is different for each person, and it is likely to be deviated from a sense of the driver when the driver actually manually drives the vehicle. In the worst case, an unnecessary intervention of the driver may be induced during autonomous driving.

In view of this, the present invention provides an information notification device, an information notification method, an information notification program, and an information processing system capable of solving at least one of the foregoing problems during full autonomous driving or limited autonomous driving.

Specifically, an information notification device according to one aspect of the present invention is mounted to a vehicle including a detector that detects a surrounding situation of the vehicle and a travel state of the vehicle, and a vehicle controller that determines a behavior of the vehicle based on the surrounding situation of the vehicle and the travel state of the vehicle which have been detected by the detector, the information notification device being provided with: an information acquisition unit that, when it is determined that there is a possibility of updating a behavior of the vehicle during autonomous driving, acquires information of the behavior to be executed; and a notification unit that provides notification regarding the behavior to be executed before the behavior of the vehicle is updated.

An information notification method according to one aspect of the present invention is an information notification method executed in a vehicle which detects a surrounding situation of the vehicle and a travel state of the vehicle, and determines a behavior of the vehicle based on the surrounding situation of the vehicle and the travel state of the vehicle which have been detected, the method including: when it is determined that there is a possibility of updating a behavior of the vehicle during autonomous driving, acquiring information of the behavior to be executed; and providing notification regarding the behavior to be executed before the behavior of the vehicle is updated.

An information notification program according to one aspect of the present invention is an information notification program executed by a computer in a vehicle which detects a surrounding situation of the vehicle and a travel state of the vehicle, and determines a behavior of the vehicle based on the surrounding situation of the vehicle and the travel state of the vehicle which have been detected, the program causing the computer to function as: information acquisition means for, when it is determined that there is a possibility of updating a behavior of the vehicle during autonomous driving, acquiring information of the behavior to be executed; and notification means for providing notification regarding the behavior to be executed before the behavior of the vehicle is updated.

According to the information notification device, the information notification method, or the information notification program described above, information can be appropriately transmitted so as to enable comfortable autonomous driving in which a vehicle operation and a driver's operation are difficult to be incompatible with each other.

Hereinafter, the information processing device and the like according to the first exemplary embodiment will be described.

FIG. 1 is a block diagram illustrating a configuration of a main part of vehicle 1 including the information notification device according to the first exemplary embodiment of the present invention. Vehicle 1 enables all of or a portion of driving control autonomously without requiring an operation by a driver.

Vehicle 1 includes brake pedal 2, accelerator pedal 3, indicator lever 4, steering wheel 5, detector 6, vehicle controller 7, storage unit 8, and information notification device 9.

Brake pedal 2 receives a brake operation performed by the driver to decelerate vehicle 1. Brake pedal 2 may also receive a result of control performed by vehicle controller 7, and vary in an amount corresponding to the degree of deceleration of vehicle 1. Accelerator pedal 3 receives an acceleration operation performed by the driver to accelerate vehicle 1. Accelerator pedal 3 may also receive a result of control performed by vehicle controller 7, and vary in an amount corresponding to the degree of acceleration of vehicle 1. Indicator lever 4 receives a lever operation performed by the driver to turn on an unillustrated turn indicator of vehicle 1. Indicator lever 4 may also receive a result of control performed by vehicle controller 7 to bring indicator lever 4 into a state corresponding to the indicated direction of vehicle 1 and turn on the unillustrated turn indicator of vehicle 1.

Steering wheel 5 receives a steering operation performed by the driver to change the travel direction of vehicle 1. Steering wheel 5 may also receive a result of control performed by vehicle controller 7, and vary in an amount corresponding to the change in the travel direction of vehicle 1. Steering wheel 5 includes operating unit 51.

Operating unit 51 is provided on a front face (face facing the driver) of steering wheel 5, and receives an input operation from the driver. Operating unit 51 is a device such as a button, a touch panel, or a grip sensor, for example. Operating unit 51 outputs the information about the input operation received from the driver to vehicle controller 7.

Detector 6 detects a travel state of vehicle 1 and a surrounding situation of vehicle 1. Then, detector 6 outputs information about the detected travel state and the detected surrounding situation to vehicle controller 7.

Detector 6 includes location information acquisition unit 61, sensor 62, speed information acquisition unit 63, and map information acquisition unit 64.

Location information acquisition unit 61 acquires, as the information about the travel state, information about the location of vehicle 1 by a global positioning system (GPS) or the like.

Sensor 62 detects the surrounding situation of vehicle 1, that is, the location of another vehicle present around vehicle 1 and the determination of whether this vehicle is a leading vehicle or not from information about the location of this vehicle and lane position information, a time to collision (TTC) from the speed of the other vehicle and the speed of vehicle 1, or an obstacle present around vehicle 1.

Speed information acquisition unit 63 acquires, as information about the travel state, information about the speed or the travel direction of vehicle 1 by an unillustrated speed sensor or the like.

Map information acquisition unit 64 acquires, as information about the surrounding situation of vehicle 1, map information around vehicle 1 such as the road on which vehicle 1 is traveling, a merging point with another vehicle on the road, the lane in which vehicle 1 is currently traveling, a position of an intersection, or the like.

Note that sensor 62 includes a millimeter-wave radar, a laser radar, a camera, or a combination thereof.

Storage unit 8 is a storage device such as a read only memory (ROM), a random access memory (RAM), a hard disk drive, or a solid state drive (SSD), and stores a correspondence between the travel environment at present and a candidate of a behavior that can be performed next (after a lapse of a first predetermined time).

The travel environment at present is an environment determined based on the location of vehicle 1, the road on which vehicle 1 is traveling, and the location and speed of another vehicle present around vehicle 1, for example. Notably, for example, whether vehicle 1 is now accelerating or decelerating, and in addition, even a possibility of collision with another vehicle after one second because of the other vehicle cutting in front of vehicle 1 may also be determined, according to the location or speed of the other vehicle, based on not only momentary data but also data before and after the moment. Thus, the action of the other vehicle can be predicted, whereby the travel environment can be recognized in more detail with higher accuracy. The behavior candidate is a candidate of a behavior that can be performed next by vehicle 1 (after a lapse of the first predetermined time) in response to the travel environment at present.

For example, storage unit 8 stores in advance three behavior candidates which are acceleration of vehicle 1, deceleration of vehicle 1, and lane change of vehicle 1 to the right, in association with a travel environment in which there is a merging lane ahead on the lane in which vehicle 1 is traveling, there is a vehicle merging from the left side of the lane, and it is possible to change lanes to the right relative to the lane in which vehicle 1 is traveling.

Storage unit 8 also stores in advance, in association with a travel environment in which a vehicle traveling in front of vehicle 1 in the same lane of vehicle 1 (hereinafter such a vehicle will be referred to as a "leading vehicle") is traveling with the speed lower than the speed of vehicle 1, and it is possible to change the lane to the adjacent lane, three behavior candidates which are a travel mode for overtaking the leading vehicle, a travel mode for changing the lane to the adjacent lane, and a travel mode for decelerating vehicle 1 to follow the leading vehicle.

In addition, storage unit 8 may store the priority order of each of the behavior candidates. For example, storage unit 8 may store the number of times each behavior has been actually selected for the same previous travel environment, and may store such that the most frequently selected behavior has a higher priority order.

Vehicle controller 7 can be implemented as a part of a large scale integration (LSI) circuit or an electronic control unit (ECU) that controls the vehicle, for example. Vehicle controller 7 controls the vehicle based on information about the travel state and the surrounding situation acquired from detector 6, and controls brake pedal 2, accelerator pedal 3, indicator lever 4, and information notification device 9 according to the result of the vehicle control. Note that the target to be controlled by vehicle controller 7 is not limited to those described above.

Firstly, vehicle controller 7 determines the travel environment at present based on the information about the travel state and the surrounding situation. Conventionally proposed various methods can be used for this determination.

For example, vehicle controller 7 determines the travel environment at present to be "a travel environment in which there is a merging lane ahead on the lane in which vehicle 1 is traveling, there is a vehicle merging from the left side of the lane, and it is possible to change the lane to the right relative to the lane in which vehicle 1 is traveling", based on the information about the travel state and the surrounding situation.

Further, vehicle controller 7 determines, for example, that the time sequence of the travel environment is a "travel environment in which a vehicle traveling in front of vehicle 1 in the same lane of vehicle 1 is traveling with the speed lower than the speed of vehicle 1, and it is possible to change the lane to the adjacent lane", based on the information about the travel state and the surrounding situation.

Vehicle controller 7 causes notification unit 92 of information notification device 9 to provide notification regarding information pertaining to the travel environment indicating the travel state and the surrounding situation. Vehicle controller 7 also reads, from storage unit 8, behavior candidates that can be performed next by vehicle 1 (after a lapse of the first predetermined time) in response to the determined travel environment.

Vehicle controller 7 determines which is the most suitable for the current travel environment from among the read behavior candidates, and sets the behavior most suitable for the current travel environment as a first behavior. Notably, the first behavior may be the same as the behavior the vehicle 1 is currently doing, that is, vehicle 1 may continue the current behavior. Then, vehicle controller 7 sets, as a second behavior (different from the behavior to be performed), the behavior candidate executable by the driver other than the first behavior in the current travel environment.

For example, vehicle controller 7 may set the most suitable behavior as the first behavior using a conventional technology for determining the most suitable behavior based on the information about the travel state and the surrounding situation.

Alternatively, vehicle controller 7 may set, from among a plurality of behavior candidates, a predefined behavior as the most suitable behavior, or vehicle controller 7 may store in storage unit 8 the information about the last selected behavior, and determine this behavior as the most suitable behavior. Alternatively, vehicle controller 7 may store in storage unit 8 the number of times each behavior has been previously selected, and determine the most frequently selected behavior as the most suitable behavior.

Then, vehicle controller 7 causes notification unit 92 of information notification device 9 to provide notification regarding the information about the first behavior and the second behavior. Note that, when determining that there is no second behavior, vehicle controller 7 causes notification unit 92 to provide notification regarding only the first behavior.

It is to be noted that vehicle controller 7 may cause notification unit 92 to simultaneously provide notifications regarding the information about the first behavior and the second behavior and the information about the travel state and the surrounding situation.

In addition, vehicle controller 7 acquires information about the operation received by operating unit 51 from the driver. Vehicle controller 7 determines whether or not operating unit 51 has received an operation within a second predetermined time after the notification regarding the first behavior and the second behavior. This operation corresponds to an operation for selecting one of behaviors included in the second behavior, for example.

When operating unit 51 has not received an operation within the second predetermined time, vehicle controller 7 controls the vehicle such that the vehicle executes the first behavior, and controls brake pedal 2, accelerator pedal 3, and indicator lever 4 according to the result of the vehicle control.

When operating unit 51 has received an operation within the second predetermined time, vehicle controller 7 performs the control corresponding to the received operation.

Information notification device 9 acquires various types of information regarding the traveling of vehicle 1 from vehicle controller 7, and provides notification regarding the acquired information. Information notification device 9 includes information acquisition unit 91 and notification unit 92.

Information acquisition unit 91 acquires various types of information regarding the traveling of vehicle 1 from vehicle controller 7. For example, when determining that vehicle controller 7 may update the behavior of vehicle 1, information acquisition unit 91 acquires the information about the first behavior and the information about the second behavior from vehicle controller 7.

Then, information acquisition unit 91 temporarily stores the acquired information in an unillustrated storage unit, and reads the stored information from the storage unit and outputs the read information to notification unit 92 as needed.

Notification unit 92 notifies the driver of the information regarding the traveling of vehicle 1. Notification unit 92 may be: a display for displaying information, including a light emitting element such as a light emitting diode (LED) provided on, for example, a car navigation system, a head-up display, a center display, steering wheel 5, and a pillar installed in the vehicle; a speaker for notifying the driver of information by converting the information into a sound; or a vibrator provided on a position (for example, a seat for the driver, steering wheel 5, and the like) where the driver can sense the vibration. In addition, notification unit 92 may be a combination of these elements.

In the following description, notification unit 92 is described as a display device.

In this case, notification unit 92 is, for example, a head up display (HUD), a liquid crystal display (LCD), a head-mounted display or a helmet-mounted display (HMD), smart glasses, and other exclusive displays. HUD may be a windshield of vehicle 1, or a glass surface or a plastic surface (for example, combiner) separately provided, for example. Further, the windshield may be a front windscreen, or a side windscreen or a rear windscreen of vehicle 1, for example.

In addition, the HUD may be a transmission display provided on the surface or the inside of the windshield. Herein, the transmission display is, for example, a transmission organic electroluminescence (EL) display or a transparent display using glass that emits light when being irradiated with light of a specific wavelength. The driver can visually recognize the display on the transmission display while viewing a background. As described above, notification unit 92 may be a display medium that transmits light. In any case, an image is displayed on notification unit 92.

Notification unit 92 notifies the driver of the information regarding the traveling acquired from vehicle controller 7 through information acquisition unit 91. For example, notification unit 92 notifies the driver of the information about the first behavior and the second behavior acquired from vehicle controller 7.

Hereinafter, a specific display content and an operation performed on operating unit 51 will be described.

Figure 2:
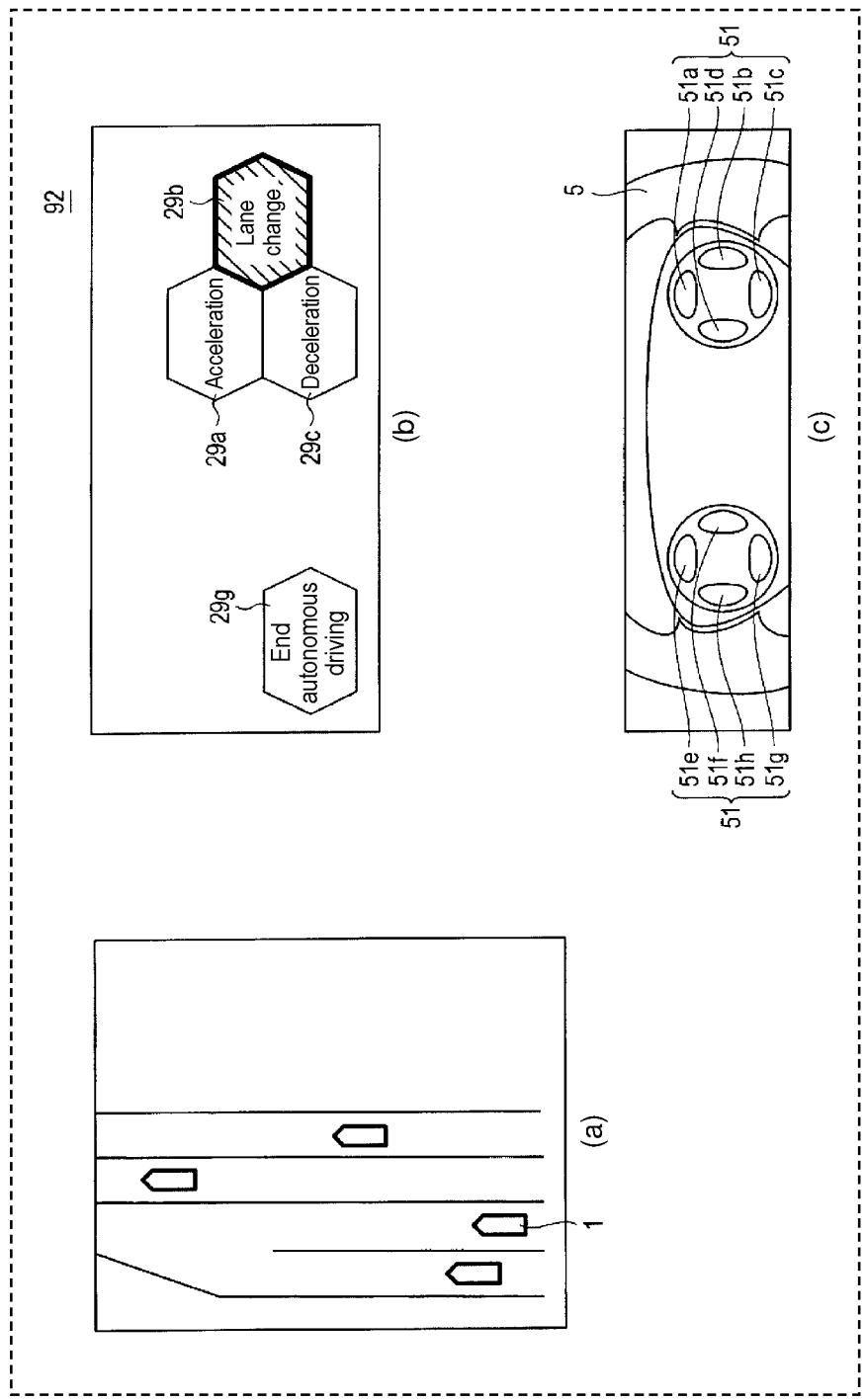
FIG. 2 is a view for describing a first example of a travel environment, a display on a notification unit for the first example of the travel environment, and an operation to an operating unit.

FIG. 2 is a view for describing a first example of a travel environment, a display on notification unit 92 for the first example, and an operation to operating unit 51.

Part (a) of FIG. 2 is an overhead view illustrating the travel environment of vehicle 1. Specifically, part (a) of FIG. 2 illustrates a travel environment in which there is a merging lane ahead on the lane in which vehicle 1 is traveling, there is a vehicle merging from the left side of the lane, and it is possible to change lanes to the right relative to the lane in which vehicle 1 is traveling.

Vehicle controller 7 determines that the travel environment is the one illustrated in part (a) of FIG. 2 based on the information about the travel state and the surrounding situation. Note that vehicle controller 7 may generate the overhead view illustrated in part (a) of FIG. 2, and may cause notification unit 92 to provide notification regarding the generated overhead view in addition to the information about the first behavior and the second behavior.

Part (b) of FIG. 2 illustrates one example of the display on notification unit 92 in response to the travel environment illustrated in part (a) of FIG. 2. In a display range of notification unit 92, options involved with the behavior of vehicle 1 are displayed on the right, and information for switching from autonomous driving to manual driving is displayed on the left.

The first behavior is "lane change" displayed in highlighted display region 29b in display regions 29a to 29c and 29g. The second behavior is "acceleration" and "deceleration" respectively displayed in display regions 29a and 29c. In addition, "end autonomous driving" indicating that the driving mode is switched from autonomous driving to manual driving is displayed in display region 29g.

Part (c) of FIG. 2 illustrates one example of operating unit 51 provided on steering wheel 5. Operating unit 51 includes operation buttons 51a to 51d provided on the right side of steering wheel 5 and operation buttons 51e to 51h provided on the left side of steering wheel 5. Note that the number, shape, and other conditions of operating units 51 provided to steering wheel 5 are not limited to those described above.

In the present exemplary embodiment, display regions 29a to 29c illustrated in part (b) of FIG. 2 correspond to operation buttons 51a to 51c, respectively, and display region 29g corresponds to operation button 51g.

In this configuration, when selecting any one of displays displayed in each display region, the driver presses the operation button corresponding to each display region. For example, to select the behavior of "acceleration" displayed in display region 29a, the driver presses operation button 51a.

Although only character information is displayed in each display region in part (b) of FIG. 2, a symbol or an icon involved with drive of the vehicle may be displayed as described next. According to this configuration, the driver can recognize the display content at a glance.

Figure 3:
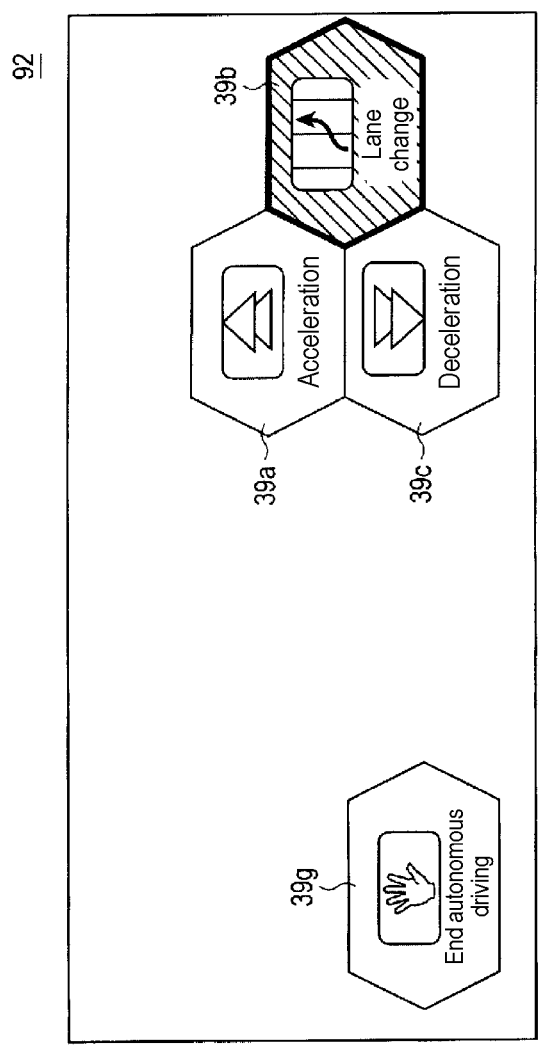
FIG. 3 is a view illustrating another example of a display on the notification unit.

FIG. 3 is a view illustrating another example of a display on notification unit 92. As illustrated in FIG. 3, character information and symbols indicating the information are both displayed in display regions 39a to 39c and 39g. Note that only symbols may be displayed.

Next, a display control flow will be described, using a specific travel environment as one example.

Figure 4:
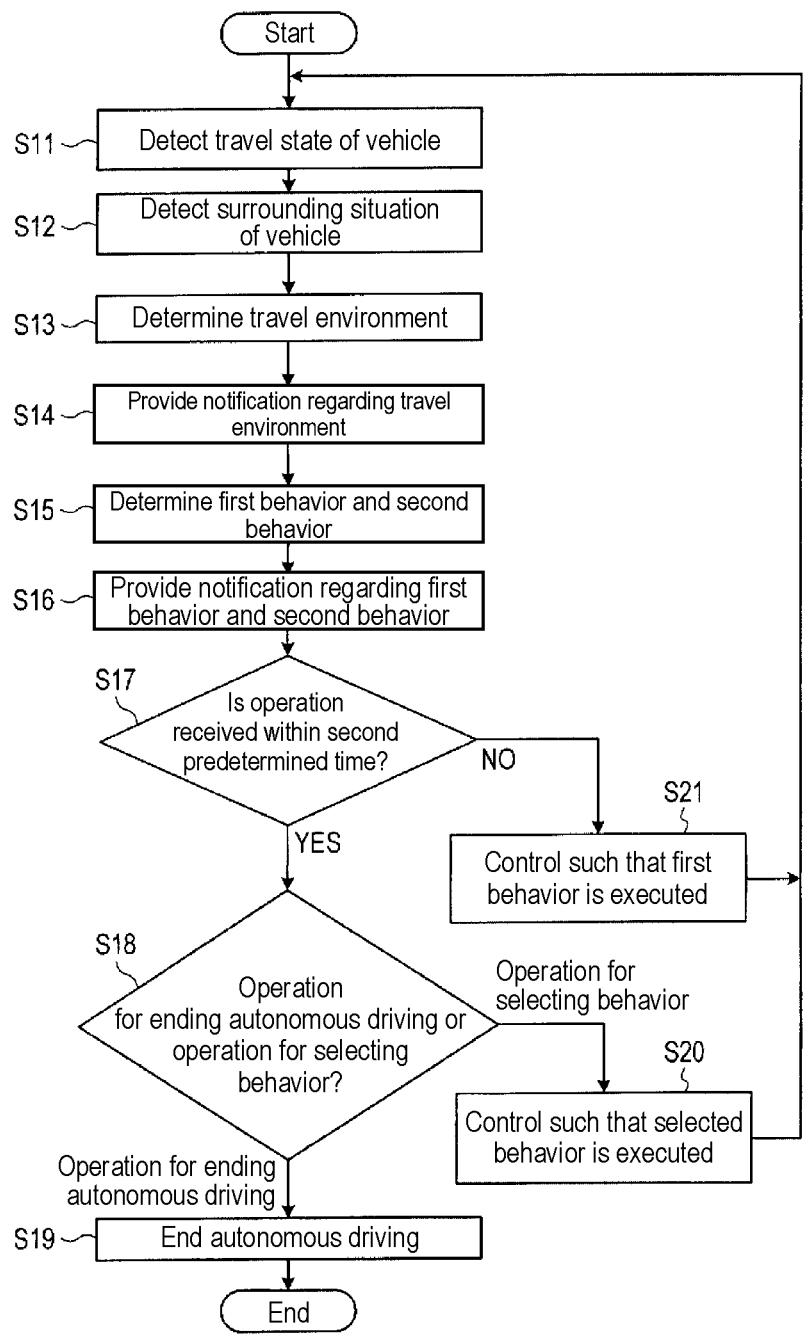
FIG. 4 is a flowchart illustrating a procedure of an information notification process according to the first exemplary embodiment of the present invention.
Figure 5:
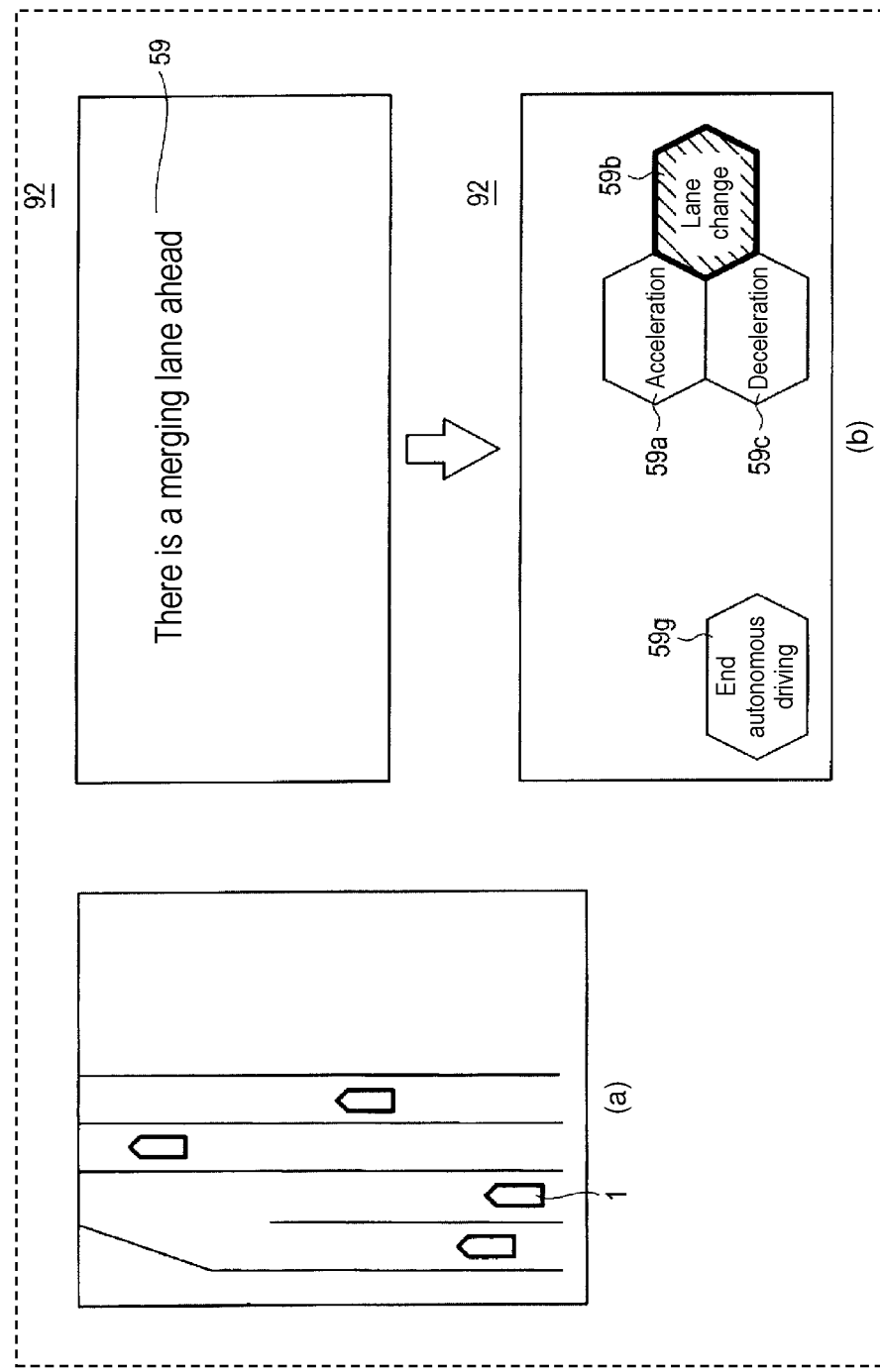
FIG. 5 is a view illustrating the first example of a travel environment, and display control for the first example of the travel environment.

FIG. 4 is a flowchart illustrating a procedure of an information notification process according to the present exemplary embodiment. FIG. 5 is a view illustrating the first example of the travel environment, and display control for this environment.

As illustrated in FIG. 4, detector 6 detects a travel state of the vehicle (step S11). Then, detector 6 detects a surrounding situation of the vehicle (step S12). Detector 6 outputs to vehicle controller 7 the information about the travel state of the vehicle and the surrounding situation of the vehicle which have been detected.

Next, vehicle controller 7 determines the travel environment at present based on the information about the travel state and the surrounding situation (step S13). In the example in part (a) of FIG. 5, vehicle controller 7 determines the travel environment at present to be "a travel environment in which there is a merging lane ahead on the lane in which vehicle 1 is traveling, there is a vehicle merging from the left side of the lane, and it is possible to change lanes to the right relative to the lane in which vehicle 1 is traveling".

Then, vehicle controller 7 causes notification unit 92 of information notification device 9 to provide notification regarding the information about the determined travel environment (step S14). In the example in part (b) of FIG. 5, vehicle controller 7 outputs the information about the determined travel environment to information acquisition unit 91. Notification unit 92 acquires the information about the travel environment from information acquisition unit 91, and displays the acquired information as character information 59. Notably, vehicle controller 7 may cause a speaker or the like to notify the driver, with a sound, of the information about the travel environment, instead of causing notification unit 92 to display the information about the travel environment. Accordingly, the information can reliably be transmitted to the driver, even if the driver does not see or fails to see the display or a monitor.

Next, vehicle controller 7 determines whether or not there is a possibility of updating the behavior for the determined travel environment. When determining that there is a possibility of updating, vehicle controller 7 then determines the first behavior and the second behavior (step S15). Whether or not there is a possibility of updating the behavior for the travel environment is determined based on whether or not the travel environment has been changed. Conceivable behaviors to be executed after the updating include decelerating the vehicle because of a possibility of collision between the vehicle and another vehicle or the like, changing the speed when a leading vehicle disappears in adaptive cruise control (ACC), and changing lanes when the adjacent lane is vacant, for example. Whether or not to perform updating is determined using the conventional technology.

In this case, vehicle controller 7 reads, from storage unit 8, the behavior candidates that can be performed next by vehicle 1 (after a lapse of the first predetermined time) in response to the determined travel environment. Then, vehicle controller 7 determines which is the most suitable for the current travel environment from among the read behavior candidates, and sets the behavior most suitable for the current travel environment as the first behavior. Thereafter, vehicle controller 7 sets the behavior candidates excluding the first behavior as the second behavior.

In the example in part (b) of FIG. 5, vehicle controller 7 reads, from storage unit 8, three behavior candidates which are acceleration of vehicle 1, deceleration of vehicle 1, and lane change of vehicle 1 to the right. Then, vehicle controller 7 determines that the lane change of vehicle 1 to the right is the most suitable behavior based on the speed of the vehicle merging from the left and the condition of the right lane of vehicle 1, and sets this behavior as the first behavior. Thereafter, vehicle controller 7 sets the behavior candidates excluding the first behavior as the second behavior.

Next, vehicle controller 7 causes notification unit 92 of information notification device 9 to provide notification regarding the first behavior and the second behavior (step S16). In the example in part (b) of FIG. 5, notification unit 92 displays character information of "lane change" which is the information about the first behavior in display region 59b in a highlighted manner, and displays "acceleration" and "deceleration", which are the information about the second behavior, in display regions 59a and 59c, respectively.

Next, vehicle controller 7 determines whether or not operating unit 51 receives an operation from the driver within a second predetermined time (step S17).

For example, vehicle controller 7 sets, as the first predetermined time, the time from when vehicle controller 7 determines that the travel environment at present is the one illustrated in part (a) of FIG. 5 until vehicle 1 reaches the merging point. Vehicle controller 7 then sets a second predetermined time shorter than the first predetermined time as a time in which the operation for the behavior to be executed next before the merging point can be received.

When operating unit 51 has received the operation from the driver within the second predetermined time (YES in step S17), vehicle controller 7 determines whether the received operation is an operation for ending autonomous driving or a behavior selecting (in other words, updating) operation (step S18).

As described with reference to FIG. 2, each of the display regions of notification unit 92 corresponds to a corresponding one of the operation buttons of operating unit 51. When selecting "end autonomous driving" in part (b) of FIG. 5, the driver presses operation button 51g illustrated in part (c) of FIG. 2. When performing behavior selection, the driver presses any one of operation buttons 51a to 51c illustrated in part (c) of FIG. 2.

When the operation received by operating unit 51 is an operation for ending autonomous driving (that is, when the depression of operation button 51g is detected), vehicle controller 7 ends autonomous driving (step S19). When the operation received by operating unit 51 is the operation for behavior selection (that is, the depression of any one of operation buttons 51a to 51c is detected), vehicle controller 7 controls vehicle 1 such that vehicle 1 performs the behavior corresponding to the depressed operation button (step S20).

When operating unit 51 has not received any operation performed by the driver within the second predetermined time (NO in step S17), vehicle controller 7 controls vehicle 1 such that vehicle 1 performs the first behavior (step S21).

Figure 6:
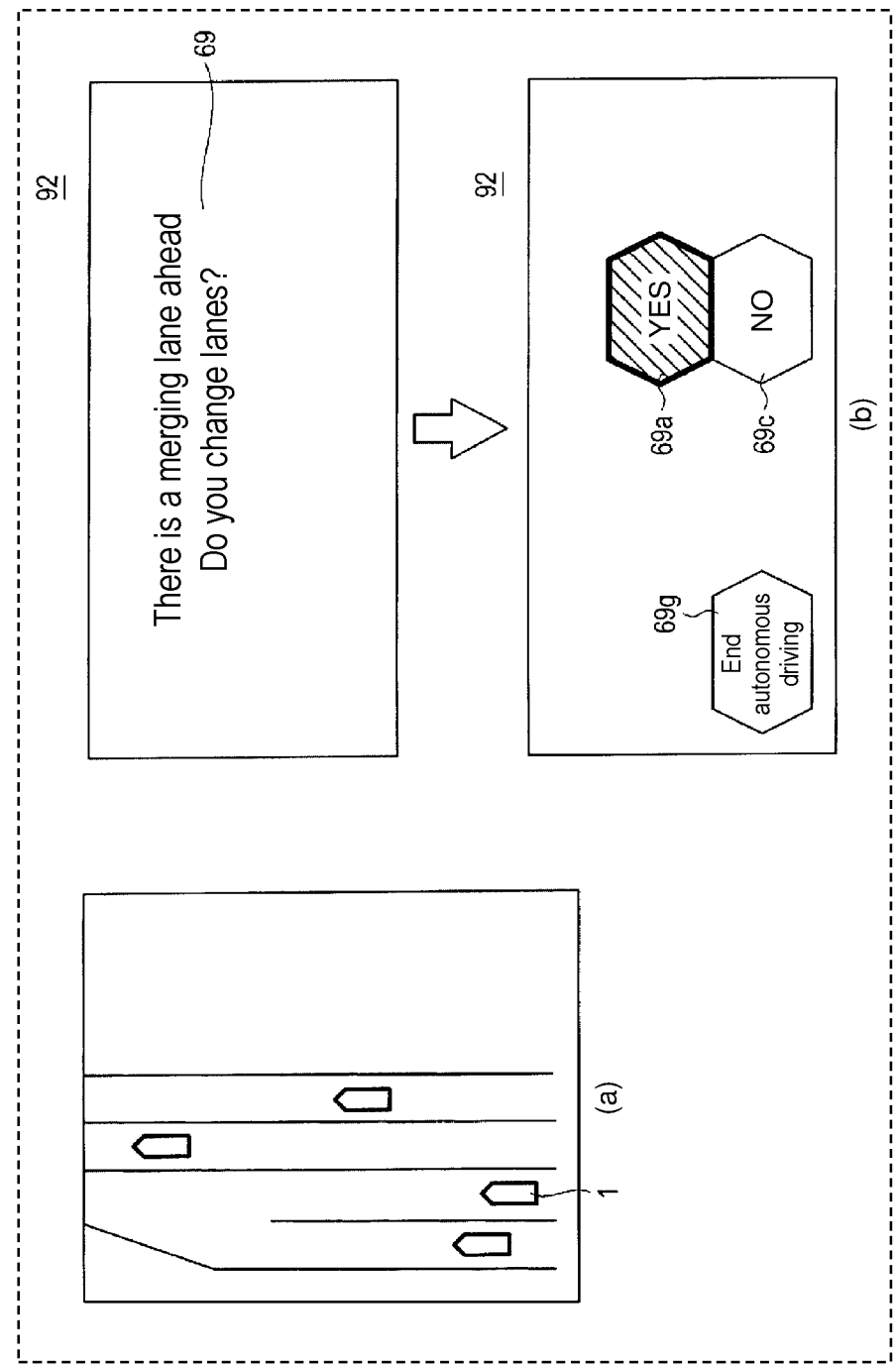
FIG. 6 is a view illustrating the first example of the travel environment, and another display control for the first example of the travel environment.

FIG. 6 is a view illustrating the first example of the travel environment, and another display control for this environment. Part (a) of FIG. 6 is similar to part (a) of FIG. 5, but the display control in part (b) of FIG. 6 is different from the display control in part (b) of FIG. 5.

As in the case described with reference to part (b) of FIG. 5, vehicle controller 7 reads, from storage unit 8, three behavior candidates which are acceleration of vehicle 1, deceleration of vehicle 1, and lane change of vehicle 1 to the right, in response to the travel environment illustrated in part (a) of FIG. 6. In this case, it is supposed that storage unit 8 stores the lane change of vehicle 1 to the right as the behavior with the highest priority.

In this case, vehicle controller 7 causes notification unit 92 to provide notification regarding the information about the travel environment and the information about the first behavior. In part (b) of FIG. 6, vehicle controller 7 creates character information 69 indicating the information about the travel environment and the information about the first behavior, and causes notification unit 92 to display character information 69.

Then, vehicle controller 7 displays, in display regions 69a and 69c, displays for encouraging the driver to determine whether to use the first behavior. Vehicle controller 7 also displays, in display region 69g, the display of "end autonomous driving" indicating that the driving is switchable from autonomous driving to manual driving.

In this case, vehicle controller 7 displays "YES" corresponding to using the first behavior in a highlighted manner. Which one of "YES" and "NO" is displayed in a highlighted manner may be set in advance, the last selected option may be displayed in a highlighted manner, or storage unit 8 may store the number of times each behavior has been previously selected and notification unit 92 may display the most frequently selected behavior in a highlighted manner.

By learning the previously selected behavior in this way, vehicle controller 7 can appropriately notify the driver of information. In addition, the display to be displayed on notification unit 92 can be less than the display in part (b) of FIG. 5, whereby the burden on the driver can be reduced.

Figure 7:
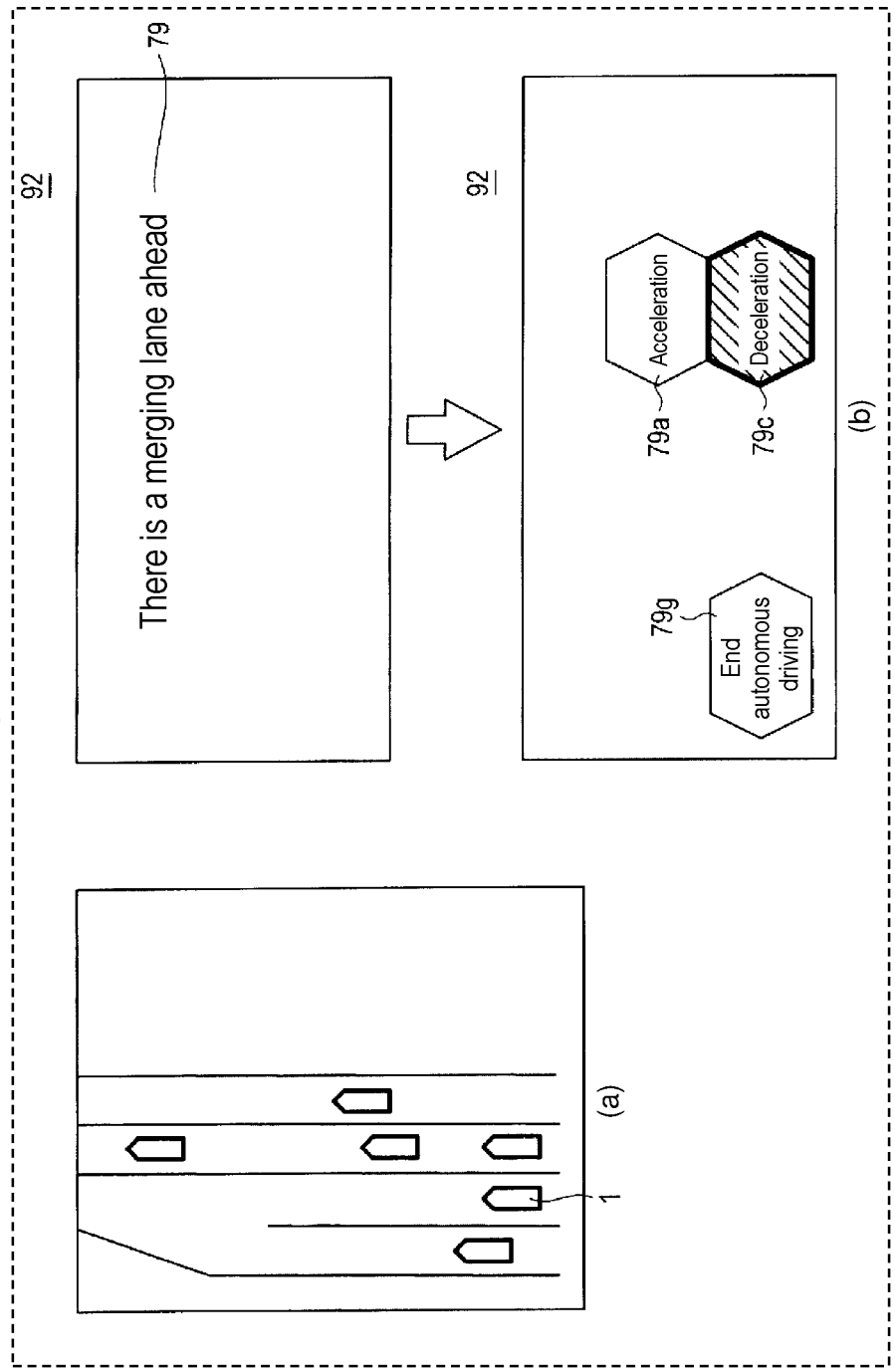
FIG. 7 is a view illustrating a second example of the travel environment, and display control for the second example of the travel environment.

FIG. 7 is a view illustrating a second example of the travel environment, and display control for this environment. Part (a) of FIG. 7 is an overhead view illustrating the travel environment. The travel environment illustrated in part (a) of FIG. 7 is similar to those in part (a) of FIG. 5 and part (a) of FIG. 6 in that there is a merging lane ahead, but different from those in part (a) of FIG. 5 and part (a) of FIG. 6 in that there is a traveling vehicle on the right of vehicle 1. In such a case, vehicle controller 7 determines that it is impossible to change lanes.

When determining that the travel environment of vehicle 1 is the one illustrated in part (a) of FIG. 7, vehicle controller 7 causes notification unit 92 to display information about the determined travel environment as character information 79 as illustrated in part (b) of FIG. 7.

Further, vehicle controller 7 selects only acceleration of vehicle 1 and deceleration of vehicle 1 from among three behavior candidates read from storage unit 8, which are acceleration of vehicle 1, deceleration of vehicle 1, and lane change of vehicle 1 to the right, because the lane change of vehicle 1 to the right is impossible.

In addition, vehicle controller 7 predicts that vehicle 1 becomes too close to the merging vehicle if vehicle 1 is traveling with the current speed, and determines that the deceleration of vehicle 1 is the most suitable behavior, that is, the first behavior.

In this case, which is the most suitable behavior among the three behavior candidates is determined using a conventional technology for determining the most suitable behavior based on the information about the travel state and the surrounding situation. Alternatively, which is the most suitable behavior may be determined in advance, or vehicle controller 7 may store the information about the last selected behavior in storage unit 8, and determine this behavior as the most suitable behavior. Alternatively, vehicle controller 7 may store in storage unit 8 the number of times each behavior has been previously selected, and determine the most frequently selected behavior as the most suitable behavior.

Thereafter, vehicle controller 7 displays "deceleration" in display region 79c as the first behavior, and displays "acceleration" in display region 79a as the second behavior. Vehicle controller 7 also displays, in display region 79g, the display of "end autonomous driving" indicating that the driving is switched from autonomous driving to manual driving.

With this display control, vehicle controller 7 can notify the driver of the behavior most suitable for the travel environment as the first behavior according to the travel environment.

The information about the first behavior may be disposed on an upper side, the information about the second behavior may be disposed on a lower side, and functions of selecting the first behavior and the second behavior may be assigned to operation buttons 51a and 51c, respectively. In addition, the information about a behavior of acceleration may be disposed on an upper side, the information about a behavior of deceleration may be disposed on a lower side, the information about the behavior of lane change to the right may be disposed on a right side, the information about the behavior of lane change to the left may be disposed on a left side, and functions of selecting the behavior of acceleration, the behavior of deceleration, the behavior of lane change to the right, and the behavior of lane change to the left may be assigned to operation buttons 51a, 51b, 51c, and 51d, respectively. Furthermore, these displays may be switchable, and whether priority is placed on action or priority is placed on operation may be displayed separately. In addition, the display size of the first behavior information may be larger, and the display size of the second behavior information may be smaller. It is to be noted that, when behavior information display is arranged corresponding to the behavior in the front-rear direction and left-right direction of the vehicle, the driver can have intuitive recognition and perform operation.

Next, an example of a travel environment other than the travel environment where there is a merging lane ahead will be described.

Figure 8:
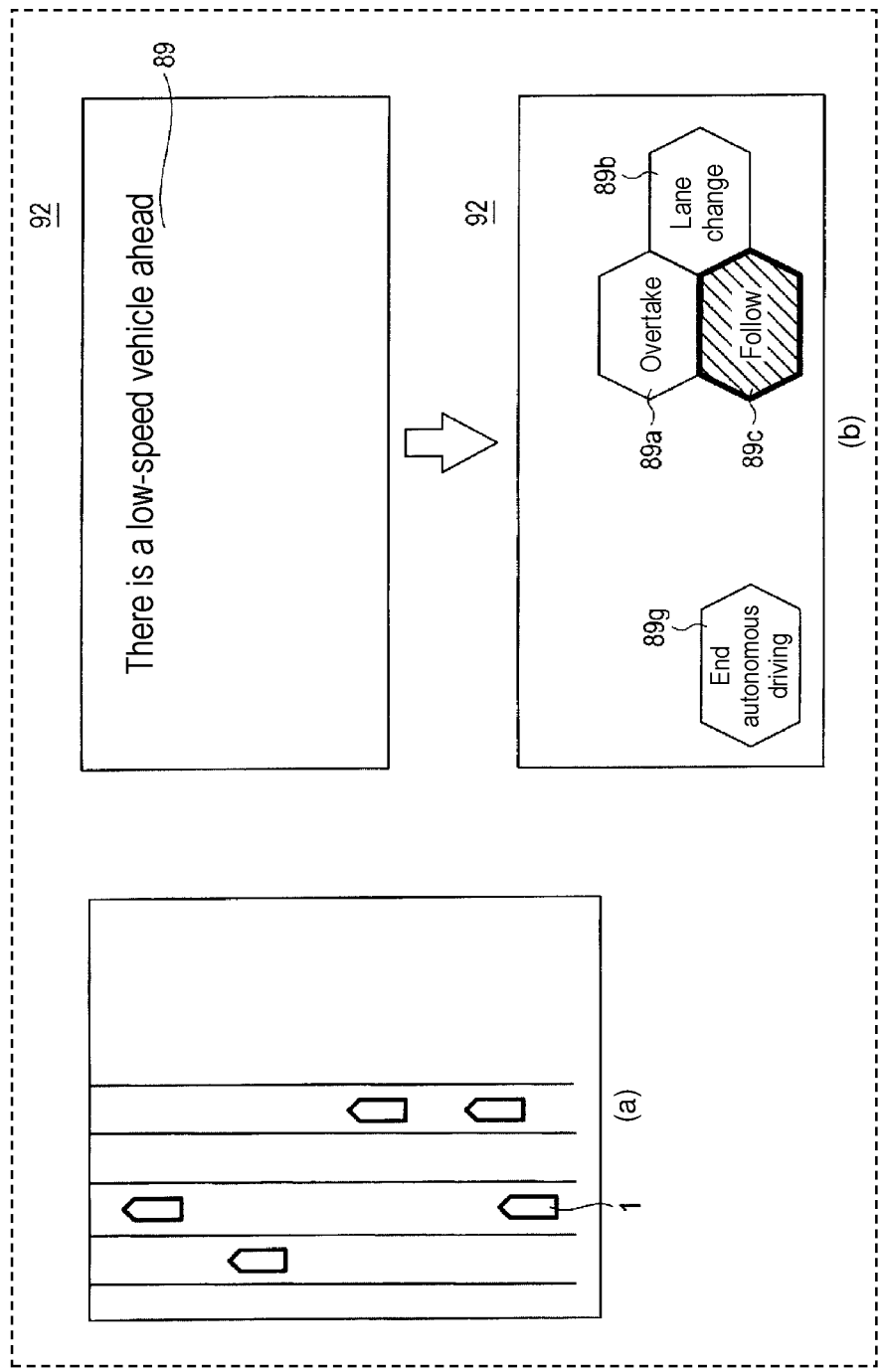
FIG. 8 is a view illustrating a third example of the travel environment, and display control for the third example of the travel environment.

FIG. 8 is a view illustrating a third example of the travel environment, and display control for this environment. Part (a) of FIG. 8 is an overhead view illustrating the travel environment of vehicle 1. Specifically, part (a) of FIG. 8 illustrates the travel environment where a leading vehicle is traveling with a speed lower than the speed of vehicle 1, and a lane change to the adjacent lane is possible.

Vehicle controller 7 determines that the travel environment is the one illustrated in part (a) of FIG. 8 based on the information about the travel state and the surrounding situation. In this case, vehicle controller 7 causes notification unit 92 to display the information about the determined travel environment as character information 89.

Vehicle controller 7 also reads, as behavior candidates corresponding to the determined travel environment, three behavior candidates which are a travel mode for overtaking the leading vehicle, a travel mode for performing a lane change to the adjacent lane, and a travel mode for decelerating vehicle 1 to follow the leading vehicle, from storage unit 8.

For example, vehicle controller 7 determines that the travel mode for decelerating vehicle 1 to follow the leading vehicle is the most suitable behavior, that is, the first behavior, because the speed of the leading vehicle after deceleration is higher than a predetermined value and is allowable.

In this case, which is the most suitable behavior among the three behavior candidates is determined using a conventional technology for determining the most suitable behavior based on the information about the travel state and the surrounding situation. Alternatively, which is the most suitable behavior may be determined in advance, or vehicle controller 7 may store the information about the last selected behavior in storage unit 8, and determine this behavior as the most suitable behavior. Alternatively, vehicle controller 7 may store in storage unit 8 the number of times each behavior has been previously selected, and determine the most frequently selected behavior as the most suitable behavior.

Vehicle controller 7 also displays character information of "follow" indicating the first behavior in display region 89c in a highlighted manner, and character information items of "overtake" and "lane change" indicating the second behavior in display regions 89a and 89b, respectively, as illustrated in part (b) of FIG. 8. Vehicle controller 7 also displays, in display region 89g, the display of "end autonomous driving" indicating that the driving is switched from autonomous driving to manual driving.

The information about the first behavior may be disposed on an upper side, the information about the second behavior may be disposed on a lower side, and functions of selecting the first behavior and the second behavior may be assigned to operation buttons 51a and 51c, respectively; the information about the overtaking behavior may be disposed on an upper side, the information about the following behavior may be disposed on a lower side, the information about the behavior of lane change to the right may be disposed on a right side, the information about the behavior of lane change to the left may be disposed on a left side, and functions of selecting the overtaking behavior, the following behavior, the behavior of lane change to the right, and the behavior of lane change to the left may be assigned to operation buttons 51*a*, 51*c*, 51*b*, and 51*d*, respectively. Furthermore, these displays may be switchable, and whether priority is placed on action or priority is placed on operation may be displayed separately. In addition, the display size of the first behavior information may be larger, and the display size of the second behavior information may be smaller.

Figure 9:
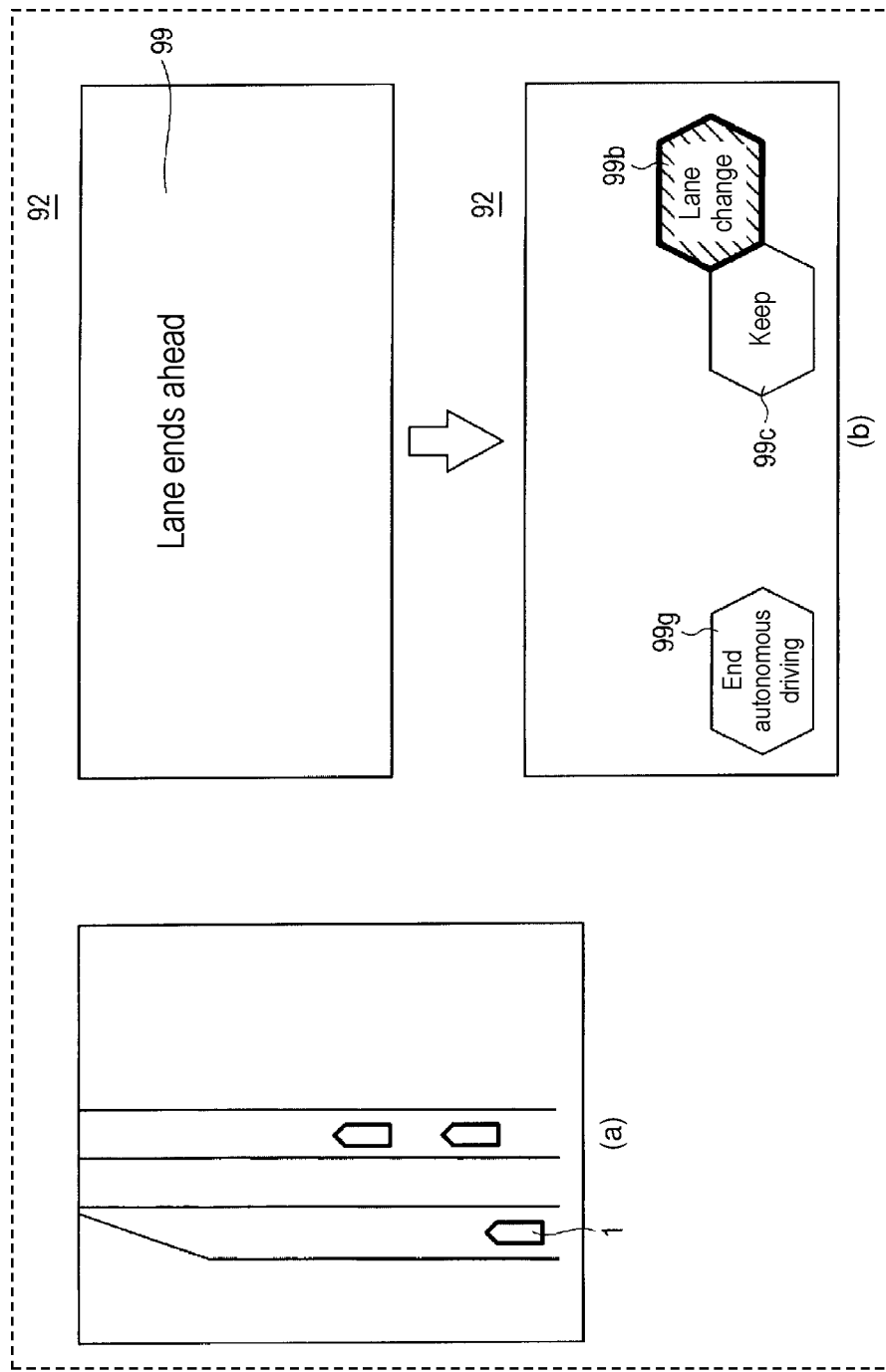
FIG. 9 is a view illustrating a fourth example of the travel environment, and display control for the fourth example of the travel environment.

FIG. 9 is a view illustrating a fourth example of the travel environment, and display control for this environment. Part (a) of FIG. 9 is an overhead view illustrating the travel environment of vehicle 1. Specifically, part (a) of FIG. 9 illustrates the travel environment where the lane in which vehicle 1 is traveling ends ahead.

Vehicle controller 7 determines that the travel environment is the one illustrated in part (a) of FIG. 9 based on the information about the travel state and the surrounding situation. In this case, vehicle controller 7 causes notification unit 92 to display the information about the determined travel environment as character information 99.

Vehicle controller 7 also reads, as behavior candidates corresponding to the determined travel environment, two behavior candidates which are a travel mode for performing a lane change to the adjacent lane, and a travel mode for keeping traveling in the current lane, from storage unit 8.

For example, vehicle controller 7 determines that the travel mode for performing a lane change to the adjacent lane is the most suitable behavior, that is, the first behavior, because TTC to the point where the lane ends is shorter than a predetermined value.

In this case, which is the most suitable behavior between the two behavior candidates is determined using a conventional technology for determining the most suitable behavior based on the information about the travel state and the surrounding situation. Alternatively, which is the most suitable behavior may be determined in advance, or vehicle controller 7 may store the information about the last selected behavior in storage unit 8, and determine this behavior as the most suitable behavior. Alternatively, vehicle controller 7 may store in storage unit 8 the number of times each behavior has been previously selected, and determine the most frequently selected behavior as the most suitable behavior.

Vehicle controller 7 also displays character information of "lane change" indicating the first behavior in display region 99*b* in a highlighted manner, and character information of "keep" indicating the second behavior in display region 99*c*, as illustrated in part (b) of FIG. 9. Vehicle controller 7 also displays, in display region 99*g*, the display of "end autonomous driving" indicating that the driving is switched from autonomous driving to manual driving.

The information about the first behavior may be disposed on an upper side, the information about the second behavior may be disposed on a lower side, and functions of selecting the first behavior and the second behavior may be assigned to operation buttons 51*a* and 51*c*, respectively; information about a behavior of doing nothing may be disposed on a lower side, the information about the behavior of lane change to the right may be disposed on a right side, the information about the behavior of lane change to the left may be disposed on a left side, and functions of selecting the behavior of doing nothing, the behavior of lane change to the right, and the behavior of lane change to the left may be assigned to operation buttons 51*c*, 51*b*, and 51*d*, respectively; or these displays may be switchable, and whether priority is placed on action or priority is placed on operation may be displayed separately. In addition, the display size of the first behavior information may be larger, and the display size of the second behavior information may be smaller. Notably, due to the configuration in which a different function is assigned to each display region depending on a different travel environment as illustrated in FIGS. 7, 8, and 9, notification of information or operation is enabled with fewer regions.

It has been described above that vehicle controller 7 causes notification unit 92 to provide notification regarding a behavior according to the information about the travel environment and surrounding situation. However, the present invention is not limited thereto. For example, it may be configured such that vehicle controller 7 causes notification unit 92 to provide notification regarding a behavior when the driver performs a predetermined operation.

Figure 10:
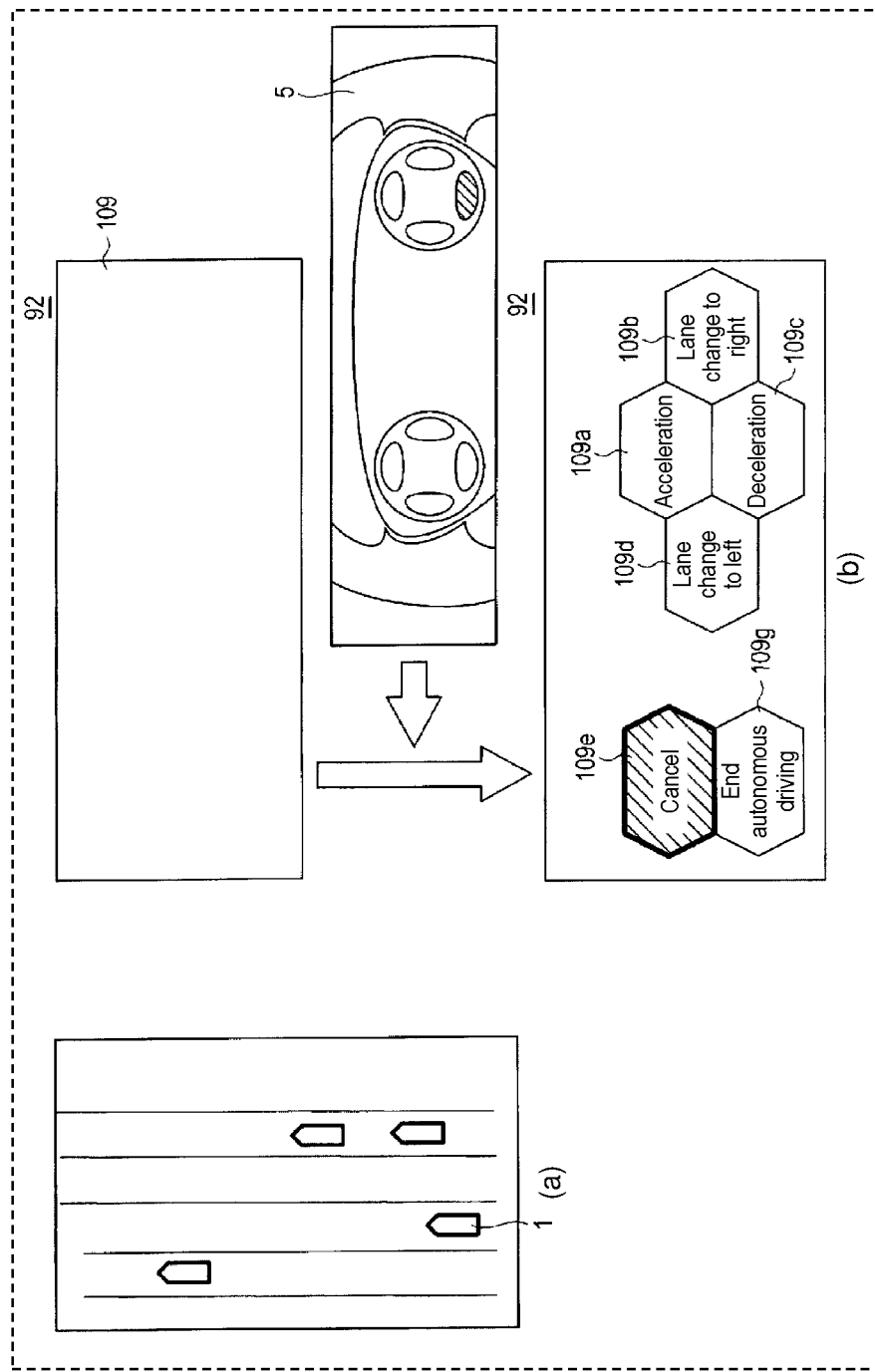
FIG. 10 is a view illustrating a fifth example of the travel environment, and display control for the fifth example of the travel environment.

FIG. 10 is a view illustrating a fifth example of the travel environment, and display control for this environment. Part (a) of FIG. 10 is an overhead view illustrating the travel environment of vehicle 1. Specifically, part (a) of FIG. 10 illustrates the travel environment where vehicle 1 can change lanes to the left and right.

Part (a) of FIG. 10 illustrates the travel environment where, different from the travel environments illustrated in part (a) of FIG. 5 to part (a) of FIG. 9, vehicle 1 can travel in a normal way without requiring a lane change or acceleration and deceleration of the vehicle. In this case, vehicle controller 7 may cause notification unit 92 not to display the information about the travel environment as character information as indicated by display 109 in part (b) of FIG. 10.

When the driver depresses any of the operation buttons on operating unit 51 under the above-described condition where character information is not displayed on notification unit 92, vehicle controller 7 reads the behavior candidates in a normal travel from storage unit 8.

Specifically, storage unit 8 stores four behavior candidates which are acceleration of vehicle 1, deceleration of vehicle 1, lane change of vehicle 1 to the right, and lane change of vehicle 1 to the left, in association with the travel environment of normal travel as illustrated in part (a) of FIG. 10. Vehicle controller 7 reads these behavior candidates, and causes notification unit 92 to display these behavior candidates in display regions 109*a* to 109*d*, respectively.

In addition, vehicle controller 7 displays the display of "end autonomous driving" indicating that the driving is switched from autonomous driving to manual driving in display region 109*g*, and a display of "cancel" indicating that updating of the behavior is canceled in display region 109*e* in a highlighted manner.

The present exemplary embodiment described above can effectively notify the driver of the behavior candidates to be executed next, thereby enabling the driver to select a more preferable behavior.

Note that the driver may directly perform a manual operation on the steering wheel or the like, instead of selecting the behavior he/she desires to do. Thus, the driver can quickly switch to a manual driving operation according to his/her intention.

[Modification]

In the present exemplary embodiment described above, character information is displayed on notification unit 92. However, the present invention is not limited thereto. For example, information may be displayed using a symbol indicating the behavior for enabling the driver to visually recognize the information. Hereinafter, a display using a symbol for enabling the driver to visually recognize information will be described, using the displays in FIGS. 5 and 7 as one example.

Figure 11:
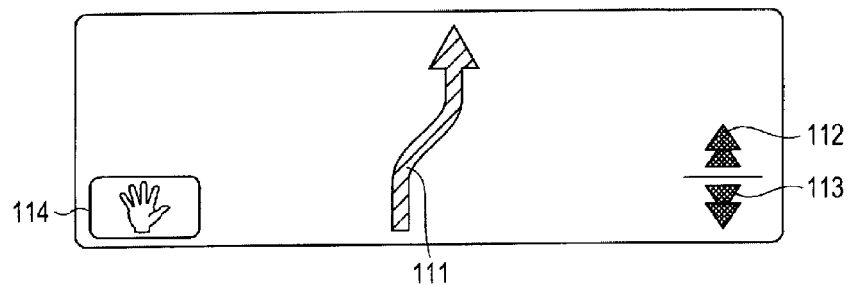
FIG. 11 is a view illustrating another display control for the first example of the travel environment illustrated in FIG. 5.

FIG. 11 is a view illustrating another display control for the first example of the travel environment illustrated in FIG. 5. In this example, the above-described first behavior is a lane change of vehicle 1 to the right, and the second behavior is acceleration of vehicle 1 and deceleration of vehicle 1.

In this case, symbol 111 indicating "lane change" which is the first behavior is displayed bigger on the center, and symbol 112 indicating "acceleration of vehicle 1" and symbol 113 indicating "deceleration of vehicle 1" which are the second behavior are displayed smaller on the right. In addition, symbol 114 indicating ending of autonomous driving is displayed smaller on the left.

If an instruction for changing the behavior of vehicle 1 is not received from the driver, the lane change is performed.

Figure 12:
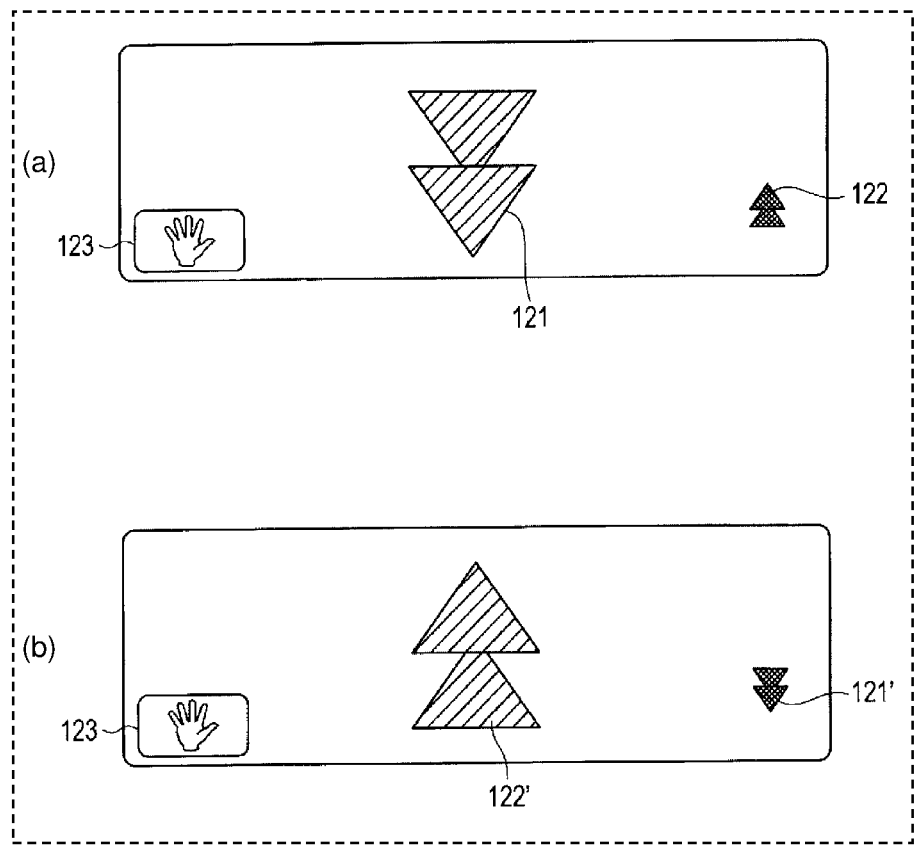
FIG. 12 is a view illustrating another display control for the second example of the travel environment illustrated in FIG. 7.

FIG. 12 is a view illustrating another display control for the second example of the travel environment illustrated in FIG. 7. In this example, different from the first example, a lane change is impossible because another vehicle is traveling on the right of vehicle 1. Therefore, "deceleration of vehicle 1" is set as the first behavior, and "acceleration of vehicle 1" is set as the second behavior, for example.

In this case, as illustrated in part (a) of FIG. 12, symbol 121 indicating "deceleration of vehicle 1" which is the first behavior is displayed bigger on the center, and symbol 122 indicating "acceleration of vehicle 1" which is the second behavior is displayed smaller on the right. In addition, symbol 123 indicating ending of autonomous driving is displayed smaller on the left.

It is supposed here that operating unit 51 receives an operation for selecting "acceleration of vehicle 1" from the driver. In this case, as illustrated in part (b) of FIG. 12, symbol 122' indicating "acceleration of vehicle 1" which is the first behavior is displayed bigger on the center, and symbol 121' indicating "deceleration of vehicle 1" which is the second behavior is displayed smaller on the right.

The present exemplary embodiment described above can effectively notify the driver of the behavior candidates to be executed next, thereby enabling the driver to select a more preferable behavior. On the other hand, the driver can recognize the behaviors to be executed by vehicle 1 or other selectable behaviors, thereby being capable of continuing autonomous driving with a feeling of trust. Alternatively, the driver can smoothly issue an instruction to the vehicle.

In addition, according to the present exemplary embodiment, the options notified by the notification unit, that is, the second behavior, can be variable according to the travel environment.

(Second Exemplary Embodiment)

The first exemplary embodiment has described the configuration in which an operation according to the display on notification unit 92 is performed using operating unit 51 provided on steering wheel 5. The present exemplary embodiment describes a configuration in which a touch panel is provided in place of operating unit 51 provided on steering wheel 5.

Figure 13:
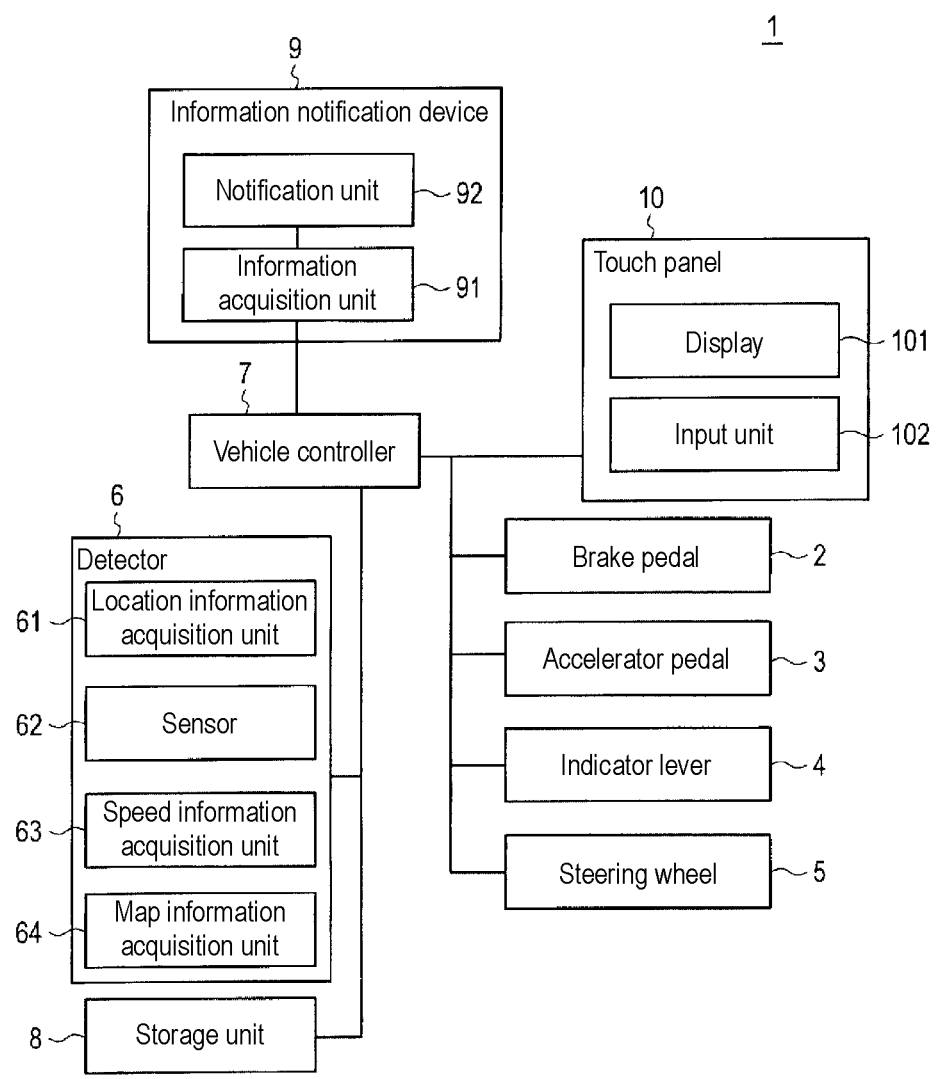
FIG. 13 is a block diagram illustrating a configuration of a main part of a vehicle including an information notification device according to a second exemplary embodiment of the present invention.

FIG. 13 is a block diagram illustrating a configuration of a main part of vehicle 1 including an information notification device according to the second exemplary embodiment. It should be noted that constituent elements in FIG. 13 which are substantially identical to the constituent elements in FIG. 1 are denoted by the identical reference numerals used in FIG. 1 and will not be described in detail. Vehicle 1 illustrated in FIG. 13 is provided with touch panel 10 in place of operating unit 51 on steering wheel 5.

Touch panel 10 is a device including a liquid crystal panel or the like and capable of displaying and inputting information, and is connected to vehicle controller 7. Touch panel 10 includes display 101 that displays information based on control by vehicle controller 7, and input unit 102 that receives an operation from a driver or the like and outputs the received operation to vehicle controller 7.

Next, display control for touch panel 10 will be described. Herein, the display control will be described for the case where vehicle 1 is traveling on the center lane of three lanes, and vehicle 1 is capable of changing the lane to the right lane or the left lane.

Figure 14:
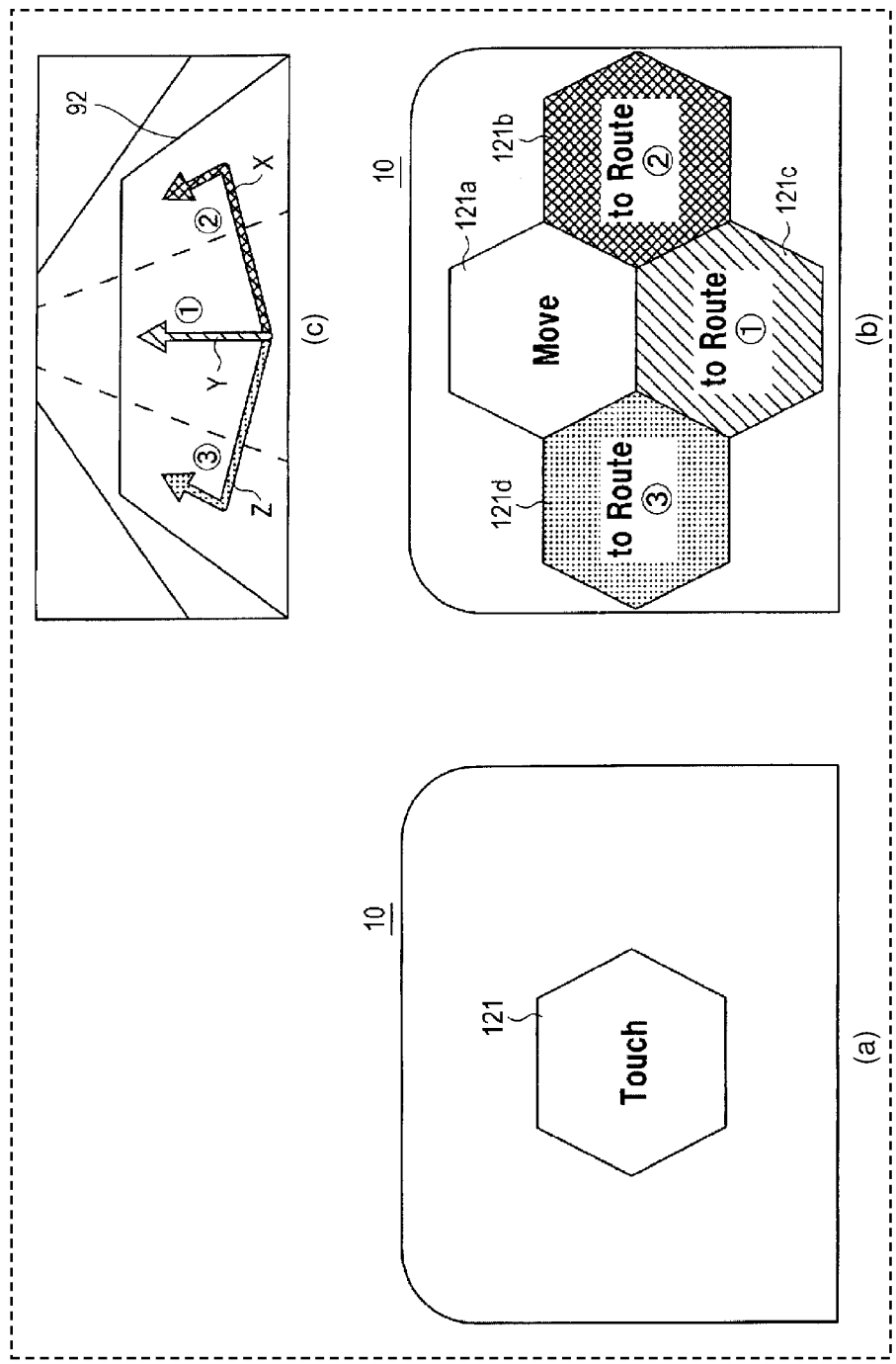
FIG. 14 is a view for describing a display on a touch panel in the second exemplary embodiment.

FIG. 14 is a view for describing the display on touch panel 10 according to the second exemplary embodiment. Part (a) of FIG. 14 illustrates an initial display on display 101 of touch panel 10. When determining that vehicle 1 is capable of changing the lane to the right lane or the left lane, vehicle controller 7 causes display 101 of touch panel 10 to execute the display illustrated in part (a) of FIG. 14. Herein, the display of "Touch" in display region 121 indicates that touch panel 10 is in a mode where a touch operation performed by the driver is acceptable.

When the driver performs the touch operation for touching display region 121 with the display illustrated in part (a) of FIG. 14 being displayed therein, input unit 102 receives this operation, and outputs to vehicle controller 7 information indicating that this operation is performed. When receiving this information, vehicle controller 7 causes display 101 to display the display illustrated in part (b) of FIG. 14, and also causes notification unit 92 to display the display illustrated in part (c) of FIG. 14.

In part (b) of FIG. 14, display region 121a having therein a display of "Move" which is an operation for instructing vehicle 1 to move is illustrated. In addition, display regions 121b to 121d indicating that it is possible for vehicle 1 to travel in each of three lanes are illustrated in part (b) of FIG. 14. Note that display regions 121b to 121d respectively correspond to traveling in lanes indicated by arrows X, Y, and Z in part (c) of FIG. 14.

In addition, each display region in part (b) of FIG. 14 and the corresponding arrow in part (c) of FIG. 14 have the same manner (for example, color, arrangement, and the like). This makes the display easy to be understood by the driver.

In addition, the lanes indicated by arrows X, Y, and Z may be displayed by varying thickness or the like such that the behavior to be executed by the vehicle determined by the vehicle controller and other behaviors selectable by the driver can be distinguished.

The driver touches the display region corresponding to the lane he/she wishes to travel, from among display regions 121b to 121d, to select the behavior of vehicle 1. In this case, input unit 102 receives the behavior selecting operation performed by the driver, and outputs information about the selected behavior to vehicle controller 7. Then, vehicle controller 7 controls vehicle 1 such that vehicle 1 executes the selected behavior. Thus, vehicle 1 travels in the lane the driver wishes to travel.

It is to be noted that the driver may swipe touch panel 10 instead of touching touch panel 10. For example, when the driver wishes to change the lane to the lane indicated by arrow X in part (c) of FIG. 14 in the example in FIG. 14, the driver swipes right on touch panel 10.

In this case, input unit 102 receives the swipe operation, and outputs the information indicating the swipe operation content to vehicle controller 7. Then, vehicle controller 7 controls vehicle 1 such that vehicle 1 executes the selected behavior of changing the lane to the lane indicated by arrow X.

In addition, when display region 121*a* displaying "Move" which indicates the operation for instructing vehicle 1 to move is displayed, the driver may utter "behavior selection" in a voice. Thus, the driver can operate by seeing only the display on the HUD without seeing the touch panel at his/her hand.

In addition, when the driver performs the touch operation or swipe operation, the display manner of the lane corresponding to the selected display region of the touch panel may be changed such that the driver can confirm which lane he/she is about to select before the selection. For example, the moment the driver touches display region 121*b*, the thickness of lane X may be enlarged, and if the driver immediately releases his/her hand, lane X may not be selected and the thickness of lane X may be returned to the original size; and the moment the driver then touches display region 121*c*, the thickness of lane Y may be enlarged, and if the driver keeps this state for a while, lane Y may be selected and may flicker to indicate that lane Y is determined. According to this configuration, the driver can perform the selecting operation or determining operation without viewing his/her hands.

Notably, as in the first exemplary embodiment, vehicle control functions such as acceleration, deceleration, overtake, and keep may be assigned to display regions according to the travel environment.

According to the present exemplary embodiment described above, the driver can perform an intuitive operation due to the touch panel being provided in place of the operating unit. Furthermore, because the number, shape, color, and the like of display regions in the touch panel receiving an operation can freely be changed, the degree of freedom of a user interface is improved.

(Third Exemplary Embodiment)

The first exemplary embodiment has described the case where the first behavior and the second behavior are simultaneously displayed. The present exemplary embodiment describes a configuration in which a first behavior is displayed first on notification unit 92, and when a driver's operation is received, a second behavior is displayed.

The configuration of the present exemplary embodiment is achieved such that a grip sensor for detecting whether or not the driver holds steering wheel 5 is further included in operating unit 51 in the configuration, illustrated in FIG. 1, described in the first exemplary embodiment.

Figure 15:
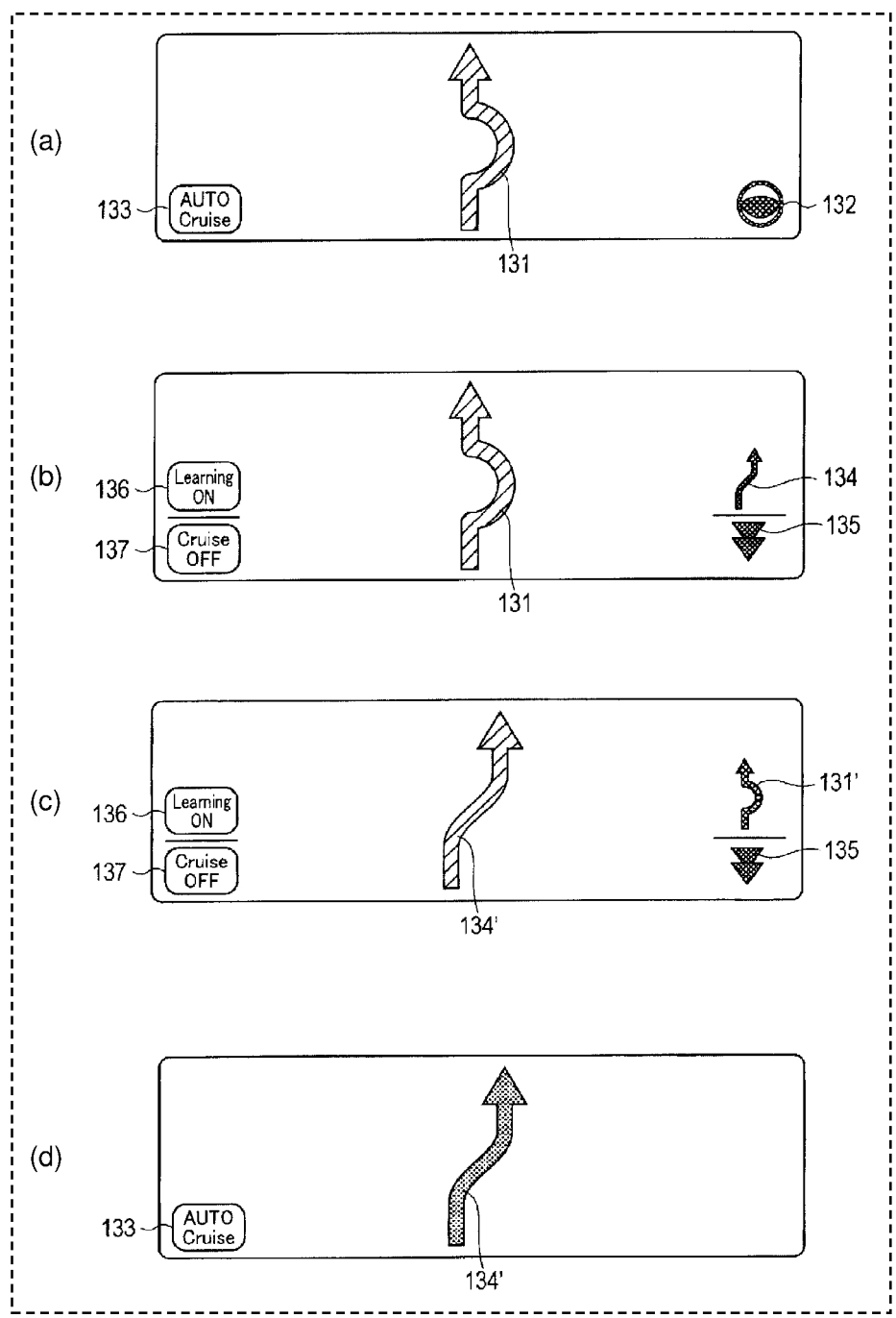
FIG. 15 is a view for describing a display on a notification unit according to a third exemplary embodiment of the present invention.

FIG. 15 is a view for describing a display on notification unit 92 according to the third exemplary embodiment of the present invention. FIG. 15 illustrates an example of a display in a travel environment, similar to that illustrated in part (a) of FIG. 8, where a vehicle traveling ahead of vehicle 1 in the same lane is traveling with a speed lower than the speed of vehicle 1, and a lane change to the adjacent lane is possible.

When determining that the travel environment is the one illustrated in part (a) of FIG. 8, vehicle controller 7 firstly causes notification unit 92 to execute the display illustrated in part (a) of FIG. 15.

In part (a) of FIG. 15, symbol 131 indicating "overtake" which is the first behavior among behavior candidates to be executed after a lapse of a first predetermined time is illustrated in a first manner (for example, in a first color).

When a second predetermined time has elapsed after vehicle controller 7 causes notification unit 92 to execute the display illustrated in part (a) of FIG. 15, vehicle controller 7 causes notification unit 92 to display symbol 131 in a second manner different from the first manner (for example, in a second color different from the first color) from the first manner. Herein, the second predetermined time is similar to the second predetermined time described in the first exemplary embodiment.

Specifically, while symbol 131 is displayed in the first manner, the driver is able to select the second behavior, but when symbol 131 is changed to the second manner, it becomes impossible for the driver to select the second behavior.

Part (a) of FIG. 15 also illustrates steering-wheel-shaped symbol 132 indicating that the second behavior is selectable. When the driver holds steering wheel 5 while symbol 132 is displayed, the second behavior is displayed. Symbol 132 is a display indicating that the second behavior is selectable. However, such configuration may be applied that the driver is notified of the second behavior being selectable by symbol 131 being displayed in the first manner. In this case, symbol 132 may not be displayed.

Part (a) of FIG. 15 also illustrates symbol 133 indicating that vehicle 1 is now in an autonomous driving mode. Symbol 133 is an auxiliary display notifying the driver that vehicle 1 is now traveling in the autonomous driving mode. However, symbol 133 may not be displayed.

When the driver holds steering wheel 5 in response to the display in part (a) of FIG. 15, the grip sensor detects the holding, and outputs information about the detection result to vehicle controller 7. In this case, vehicle controller 7 causes notification unit 92 to execute the display illustrated in part (b) of FIG. 15.

In part (b) of FIG. 15, symbol 131 indicating "overtake" which is the first behavior is illustrated in the first manner (for example, in the first color) as in part (a) of FIG. 15. In addition, symbol 134 indicating "lane change" which is the second behavior and symbol 135 indicating "deceleration" which is the second behavior are also illustrated.

The driver performs changing from the first behavior to the second behavior by operating operating unit 51 on steering wheel 5. For example, the driver updates the behavior to "lane change" (symbol 134) or "deceleration" (symbol 135) by pressing operation button 51*a* or operation button 51*c* (see part (c) of FIG. 2) on operating unit 51.

Further, symbol 136 indicating that vehicle controller 7 is learning the behavior of vehicle 1 is illustrated in part (b) of FIG. 15. While symbol 136 is displayed, vehicle controller 7 learns the behavior selected by the driver. Symbol 136 may not be displayed. Further, vehicle controller 7 may constantly learn behaviors.

Specifically, vehicle controller 7 stores the behavior selected by the driver into storage unit 8, and when vehicle 1 encounters again the similar travel environment, vehicle controller 7 causes notification unit 92 to display the stored behavior as the first behavior. Alternatively, vehicle controller 7 may store, in storage unit 8, the number of times each behavior has been previously selected, and cause notification unit 92 to display the most frequently selected behavior as the first behavior.

In part (b) of FIG. 15, symbol 137 indicating that vehicle 1 is not in the autonomous driving mode is also illustrated. When symbol 137 is displayed, vehicle controller 7 waits until the behavior to be executed after a lapse of the first predetermined time is selected by the driver.

When the driver presses operation button 51*a* on operating unit 51 in response to the display illustrated in part (b) of FIG. 15 to select "lane change", vehicle controller 7 receives the information about the selecting operation, and causes notification unit 92 to execute the display illustrated in part (c) of FIG. 15.

In part (c) of FIG. 15, symbol 134' indicating "lane change" is illustrated in the first manner. When receiving the information about the operation for selecting "lane change", vehicle controller 7 determines that the selected behavior is the behavior that is to be executed next, and causes notification unit 92 to display symbol 134' indicating "lane change" in the first manner.

Further, symbol 131 which has been displayed as the first behavior in part (b) of FIG. 15 is switched to symbol 134, and displayed as symbol 131' in part (c) of FIG. 15.

When the driver presses twice in succession any one of the operation buttons in response to the display illustrated in part (c) of FIG. 15, the selecting operation previously conducted by the driver may be canceled. In this case, vehicle controller 7 receives the information about the operation for pressing any one of the operation buttons twice in succession, and causes notification unit 92 to execute changing from the display illustrated in part (c) of FIG. 15 to the display illustrated in part (b) of FIG. 15.

In a period from the time when vehicle controller 7 causes notification unit 92 to execute the display illustrated in part (a) of FIG. 15 until the second predetermined time has elapsed, vehicle controller 7 changes the display on notification unit 92 to the display illustrated in part (b) of FIG. 15 and the display illustrated in part (c) of FIG. 15 based on the operation performed by the driver. Then, vehicle controller 7 causes notification unit 92 to execute the display illustrated in part (d) of FIG. 15 when the second predetermined time has elapsed after vehicle controller 7 causes notification unit 92 to execute the display illustrated in part (a) of FIG. 15.

Notably, when acquiring, from the grip sensor, the information indicating that the driver releases his/her hand from steering wheel 5, vehicle controller 7 may cause notification unit 92 to display the display illustrated in part (d) of FIG. 15 before the second predetermined time has elapsed.

In this case, part (d) of FIG. 15 illustrates the state where symbol 134' indicating "lane change" selected by the driver as the next behavior is displayed in the second manner, and symbol 133 indicating that vehicle 1 is traveling in the autonomous driving mode is displayed again.

According to the present exemplary embodiment described above, vehicle controller 7 changes the display on notification unit 92 such that the driver can confirm the other behavior candidates, only when the driver intends to update the behavior to be executed next. According to this configuration, the display visually confirmed by the driver can be reduced, whereby the burden on the driver can be reduced.

(Fourth Exemplary Embodiment)

The above-mentioned exemplary embodiments have described some of the methods for determining which is the most suitable behavior from among a plurality of behavior candidates executable by vehicle 1. The present exemplary embodiment describes a case where a driver model constructed in advance by learning is used as the method for determining the most suitable behavior.

The method for constructing the driver model will now be described. The driver model is constructed in such a way that the tendency of an operation performed by a driver for each travel environment is modeled based on information relating to the frequency of each operation. Travel histories of a plurality of drivers are aggregated, and the driver model is constructed from the aggregated travel histories.

The travel history of each driver is formed such that the frequency of a behavior actually selected by the driver from among behavior candidates corresponding to each travel environment is aggregated for each behavior candidate, for example.

FIG. 16 is a diagram illustrating one example of the travel history. FIG. 16 illustrates that driver x selects the behavior candidate of "deceleration" three times, "acceleration" once, and "lane change" five times, in a travel environment where "the vehicle approaches a merging lane". FIG. 16 also illustrates that driver x selects the behavior candidate of "follow" twice, "overtake" twice, and "lane change" once, in a travel environment where "there is a low-speed vehicle ahead". The same is applied to driver y.

The travel history of the driver may be formed by aggregating the behaviors selected during autonomous driving, or by aggregating the behaviors actually executed by the driver during manual driving. Thus, a travel history can be collected according to a driving state, i.e., autonomous driving or manual driving.

The driver model is classified into a clustering type constructed by clustering travel histories of a plurality of drivers, and an individually-adapted type in which a driver model of a specific driver (for example, driver x) is constructed from a plurality of travel histories similar to the travel history of driver x.

Firstly, the clustering type will be described. The clustering-type driver model is constructed in such a way that travel histories of a plurality of drivers illustrated in FIG. 16 are aggregated in advance. Then, a plurality of drivers having a high degree of similarity between the travel histories, that is, a plurality of drivers having a similar driving operation tendency, is grouped to construct a driver model.

FIG. 17 is a diagram illustrating a method for constructing the clustering-type driver model. FIG. 17 illustrates the travel histories of drivers a to f in tabular form. FIG. 17 illustrates that, from the travel histories of drivers a to f, model A is constructed based on the travel histories of drivers a to c, and model B is constructed based on the travel histories of drivers d to f.

The degree of similarity between travel histories may be obtained such that: for example, frequencies (numerical values) in the travel histories of driver a and driver b are treated as frequency distributions; a correlation value in the respective frequency distributions is calculated; and the calculated correlation value is set as the degree of similarity. In this case, when the correlation value calculated from the travel histories of driver a and driver b is higher than a predetermined value, for example, the travel histories of driver a and driver b are grouped into a single group.

Note that the calculation of the degree of similarity is not limited thereto. For example, the degree of similarity may be calculated based on the same number of the behavior having the highest frequency in the travel history of driver a and the travel history of driver b.

Then, the clustering-type driver model is constructed by calculating the average of the frequencies in the travel histories of the drivers in each group, for example.

FIG. 18 is a diagram illustrating one example of the constructed clustering-type driver model. The average frequency of the travel history in each group is derived by calculating the average of the frequencies in the travel histories of the drivers in each group illustrated in FIG. 17. In this way, the clustering-type driver model is constructed using the average frequency for the behavior determined for each travel environment.

It is to be noted that the driver model may be constructed using only the behavior having the highest frequency from among the calculated average frequencies. FIG. 19 is a diagram illustrating another example of the constructed clustering-type driver model. As illustrated in FIG. 19, the most frequent behavior is selected for each travel environment, and the driver model is constructed using the selected behavior.

Now, a method for using the constructed clustering-type driver model will be described with examples.

The driver model illustrated in FIG. 18 is stored in advance in storage unit 8 of vehicle 1. In addition, vehicle controller 7 stores, in storage unit 8, the travel history of driver y in previous driving. Notably, driver y is detected by a camera or the like (not illustrated) installed in the vehicle interior.

Then, vehicle controller 7 calculates the degree of similarity between the travel history of driver y and the travel history of each model in the driver model to determine which model is the most suitable for driver y. For example, regarding the travel history of driver y illustrated in FIG. 16 and the driver model illustrated in FIG. 18, vehicle controller 7 determines that model B is the most suitable for driver y.

Vehicle controller 7 determines that, in actual autonomous travel, the behavior having the highest frequency is the behavior most suitable for driver y, that is, the first behavior, in each travel environment in model B.

In this way, the notification regarding the behavior more suitable for the driver can be provided by constructing in advance the driver model from the travel histories of a plurality of drivers.

For example, even when the frequency of the behavior for the travel environment of "there is a low-speed vehicle ahead" is zero in the travel history of driver y as illustrated in FIG. 16, that is, even when the driver has never selected the behavior of "follow", "overtake", and "lane change" in the travel environment of "there is a low-speed vehicle ahead", vehicle controller 7 can determine the behavior of "follow" as the first behavior in the travel environment of "there is a low-speed vehicle ahead" based on model B illustrated in FIG. 18.

Next, the individually-adapted type will be described. The individually-adapted-type driver model is constructed in such a way that travel histories of a plurality of drivers illustrated in FIG. 16 are aggregated in advance, as in the method for constructing the clustering-type. The different point from the clustering-type is such that the driver model is constructed for each driver. Hereinafter, an example of constructing the driver model for driver y will be described.

Firstly, travel histories of a plurality of drivers having a high degree of similarity with the travel history of driver y are extracted from the aggregated travel histories of a plurality of drivers. Then, the driver model for driver y is constructed from the extracted travel histories of a plurality of drivers.

FIG. 20 is a diagram illustrating a method for constructing the individually-adapted-type driver model. As in FIG. 17, FIG. 20 illustrates the travel histories of drivers a to f in tabular form. FIG. 20 also illustrates that the driver model for driver y is constructed from the travel histories of drivers c to e having a high degree of similarity with the travel history of driver y illustrated in FIG. 16.

The individually-adapted-type driver model is constructed by calculating the average of the frequencies in the extracted travel histories of the drivers.

FIG. 21 is a diagram illustrating one example of the constructed individually-adapted-type driver model. In the travel history of driver y illustrated in FIG. 16 and the travel histories of drivers c to e illustrated in FIG. 20, the average frequency of each behavior is derived for each travel environment. In this way, the individually-adapted-type driver model for driver y is constructed using the average frequency for the behavior corresponding to each travel environment.

Now, a method for using the constructed individually-adapted-type driver model will be described with examples.

The driver model for driver y illustrated in FIG. 21 is stored in advance in storage unit 8 of vehicle 1. In addition, vehicle controller 7 stores, in storage unit 8, the travel history of driver y in previous driving. Notably, driver y is detected by a camera or the like (not illustrated) installed in the vehicle interior.

Vehicle controller 7 then determines that, in actual autonomous travel, the behavior having the highest frequency is the behavior most suitable for driver y, that is, the first behavior, in each travel environment in the driver model for driver y.

In this way, the notification regarding the behavior more suitable for the driver can be provided by constructing in advance the driver model for each driver from the travel histories of a plurality of drivers.

For example, even when the frequency of the behavior for the travel environment of "there is a low-speed vehicle ahead" is zero in the travel history of driver y as illustrated in FIG. 16, that is, even when the driver has never selected the behavior of "follow", "overtake", and "lane change" in the travel environment of "there is a low-speed vehicle ahead", vehicle controller 7 can determine the behavior of "lane change" as the first behavior in the travel environment of "there is a low-speed vehicle ahead" based on the driver model illustrated in FIG. 21.

A description will next be given of a case where driving characteristics of a driver (habit in driving) are acquired, and autonomous driving according to the taste of the driver is performed. In general, the actual action (for example, the level of acceleration or deceleration, or an operation amount of a steering wheel) for one behavior (for example, lane change) differs for each driver. Therefore, if autonomous driving according to the taste of the driver is enabled, more comfortable driving for the driver can be implemented.

Notably, while the case where the driving characteristics of the driver are acquired during manual driving, and the acquired driving characteristics are reflected in autonomous driving will be described below, the present invention is not limited to this case.

Vehicle controller 7 extracts a characteristic amount indicating the driving characteristics of the driver based on the content of an operation performed by the driver for each component in vehicle 1, and stores the acquired amount in storage unit 8. Herein, examples of the characteristic amount include a characteristic amount pertaining to a speed, a characteristic amount pertaining to steering, a characteristic amount pertaining to an operation timing, a characteristic amount pertaining to vehicle exterior sensing, and a characteristic amount pertaining to vehicle interior sensing.

The characteristic amount pertaining to a speed is the speed, acceleration, deceleration, or the like of the vehicle, for example, and these characteristic amounts are acquired from a speed sensor or the like mounted to the vehicle.

The characteristic amount pertaining to steering includes a steering angle, angular velocity, angular acceleration, and the like of the steering, for example, and these characteristic amounts are acquired from steering wheel 5.

The characteristic amount pertaining to an operation timing includes an operation timing of the brake, accelerator, indicator lever, steering wheel, and the like, for example, and these characteristic amounts are acquired respectively from brake pedal 2, accelerator pedal 3, indicator lever 4, and steering wheel 5.

The characteristic amount pertaining to vehicle external sensing includes the distance between vehicle 1 and a vehicle present in front of, at the side of, or at the back of vehicle 1, for example, and these characteristic amounts are acquired from sensor 62 or the like.

The characteristic amount pertaining to vehicle interior sensing includes personal identification information indicating who the driver is and who the fellow passenger is, for example, and these characteristic amounts are acquired from a camera or the like installed in the vehicle interior.

For example, when the driver manually performs a lane change, vehicle controller 7 detects that the driver manually performs the lane change. The detection is performed by analyzing operation time-series data which is acquired from controller area network (CAN) information by establishing rules on operation time-series data for a lane change in advance. Upon detection, vehicle controller 7 acquires the characteristic amount. Vehicle controller 7 stores characteristic amounts in storage unit 8 for each driver, and constructs a driving characteristic model.

Note that vehicle controller 7 may construct the driver model based on the characteristic amount for each driver. Specifically, vehicle controller 7 extracts a characteristic amount pertaining to a speed, a characteristic amount pertaining to steering, a characteristic amount pertaining to an operation timing, a characteristic amount pertaining to vehicle exterior sensing, and a characteristic amount pertaining to vehicle interior sensing, and stores the extracted characteristic amounts into storage unit 8. Then, vehicle controller 7 may construct, based on the characteristic amounts stored in storage unit 8, a driver model in which the operation tendency of the driver for each travel environment and information about the frequency of each operation are associated with each other.

FIG. 22 is a diagram illustrating one example of a driving characteristic model. FIG. 22 illustrates the characteristic amounts for each driver in tabular form. FIG. 22 also illustrates the number of times each driver has previously selected each behavior. Although FIG. 22 illustrates only some of the characteristic amounts described above, any of or all of the characteristic amounts described above may be illustrated.

The characteristic amounts illustrated in FIG. 22 will be described in detail. Numerical values in terms of the speed represent the actual speed in stages. Numerical values in terms of the steering wheel, the brake, and the accelerator represent operation amounts in stages. These numerical values are obtained, for example, by calculating the averages of the speed and the operation amounts for the steering wheel, the brake, and the accelerator during a predetermined previous time period, and by showing the averages in stages.

For example, when driver x performs a lane change without having a fellow passenger in FIG. 22, the speed level is 8, and the operation amount levels for the steering wheel, the brake, and the accelerator are respectively 4, 6, and 8.

While in autonomous driving, vehicle controller 7 selects, from the driving characteristic models in FIG. 22, the driving characteristic model corresponding to the driver, behavior, and fellow passenger, according to who the driver is, what behavior is executed, and who the fellow passenger is.

Then, vehicle controller 7 causes vehicle 1 to travel with the speed corresponding to the selected driving characteristic model, and controls vehicle 1 in combination of the operation amounts and operation timings for the steering wheel, the brake, and the accelerator. Thus, autonomous driving according to the taste of the driver can be implemented. Note that the notification regarding the information about the driving characteristic model illustrated in FIG. 22 can be provided by notification unit 92.

Figure 23:
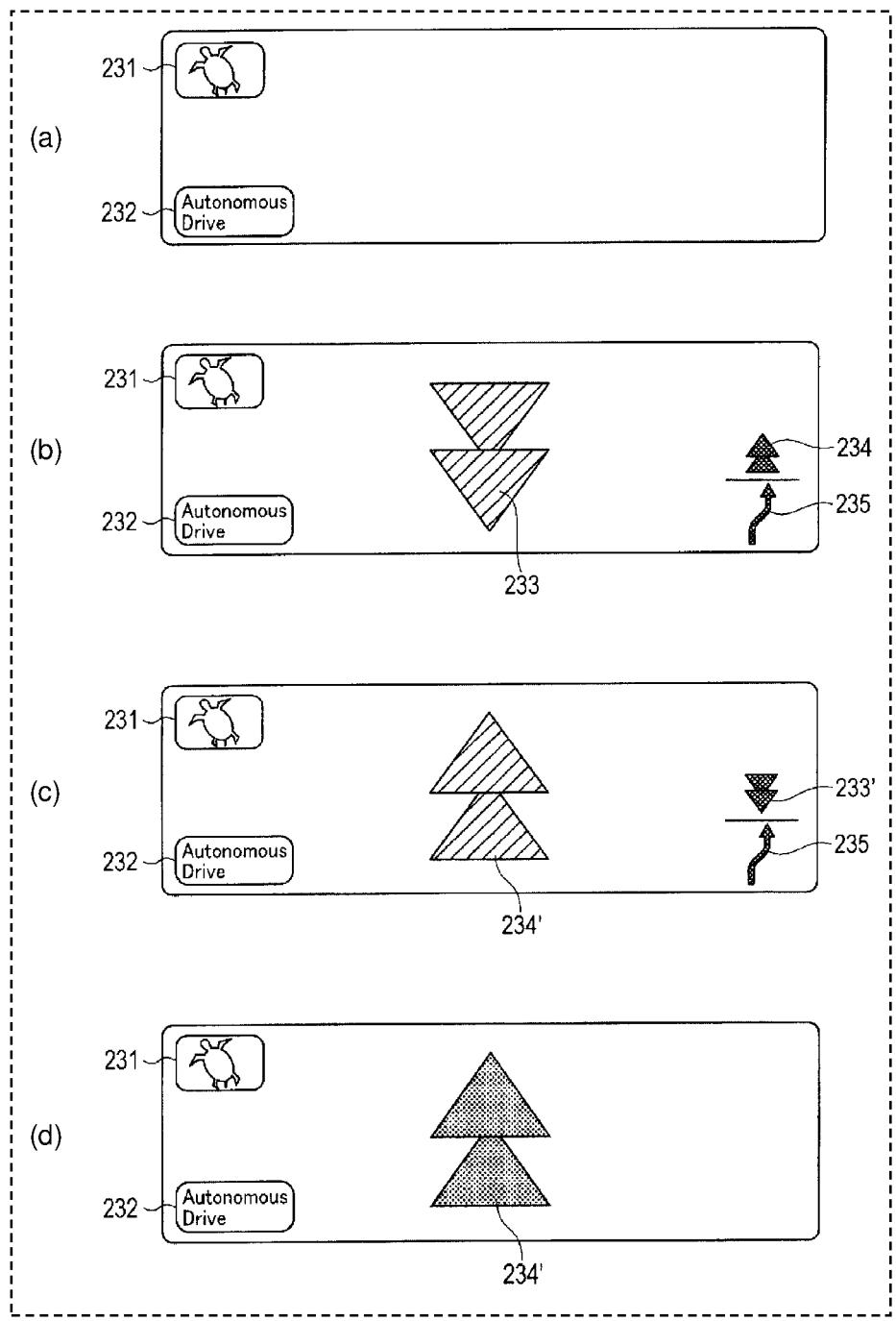
FIG. 23 is a view for describing a display on a notification unit according to a fourth exemplary embodiment of the present invention.

FIG. 23 is a view for describing a display on notification unit 92 according to the fourth exemplary embodiment of the present invention. FIG. 23 is a view illustrating a display in response to the first example of the travel environment illustrated in FIG. 5.

Part (a) of FIG. 23 illustrates a display on notification unit 92 when vehicle 1 performs normal travel without requiring a lane change or acceleration/deceleration of the vehicle. In part (a) of FIG. 23, symbol 231 indicating that the driver has a driving characteristic of "frequently decelerating" and symbol 232 indicating that the vehicle is now in an autonomous driving mode are illustrated.

Vehicle controller 7 determines the driving characteristic of the driver based on the number of times the driver has previously selected each behavior included in the driving characteristic model illustrated in FIG. 22, for example. In this case, vehicle controller 7 causes notification unit 92 to display a display including symbol 231 as illustrated in FIG. 23 for the driver who frequently "decelerates" (that is, the driver who frequently selects the behavior of "deceleration") based on the driving characteristic, for example.

When determining that the travel environment is the one in the first example illustrated in FIG. 5, vehicle controller 7 determines that the first behavior is "deceleration" based on the driver's driving characteristic of "frequently decelerating", and causes notification unit 92 to execute the display in part (b) of FIG. 23.

In part (b) of FIG. 23, symbol 233 indicating "deceleration" which is the first behavior is illustrated in the first manner (for example, in the first color). In addition, symbol 234 indicating "acceleration" which is the second behavior and symbol 235 indicating "lane change" which is the second behavior are illustrated.

When the driver changes the behavior to the behavior of "acceleration" by the operation described in the first exemplary embodiment, vehicle controller 7 causes notification unit 92 to execute the display in part (c) of FIG. 23.

In part (c) of FIG. 23, symbol 234' indicating "acceleration" which is the selected behavior is illustrated in the first manner. Further, symbol 233 which has been displayed as the first behavior in part (b) of FIG. 23 is switched to symbol 234 and displayed as symbol 233'.

Then, vehicle controller 7 causes notification unit 92 to execute the display illustrated in part (d) of FIG. 23 when the second predetermined time has elapsed after vehicle controller 7 causes notification unit 92 to execute the display illustrated in part (a) of FIG. 23. In part (d) of FIG. 23, symbol 234' indicating "acceleration" selected as the next behavior by the driver is displayed in the second manner.

When the behavior to be executed next is determined to be "acceleration", vehicle controller 7 reads characteristic amounts corresponding to the behavior of "acceleration" included in the driving characteristic model, and controls vehicle 1 such that vehicle 1 performs "acceleration" with these characteristic amounts being reflected thereon.

Figure 24:
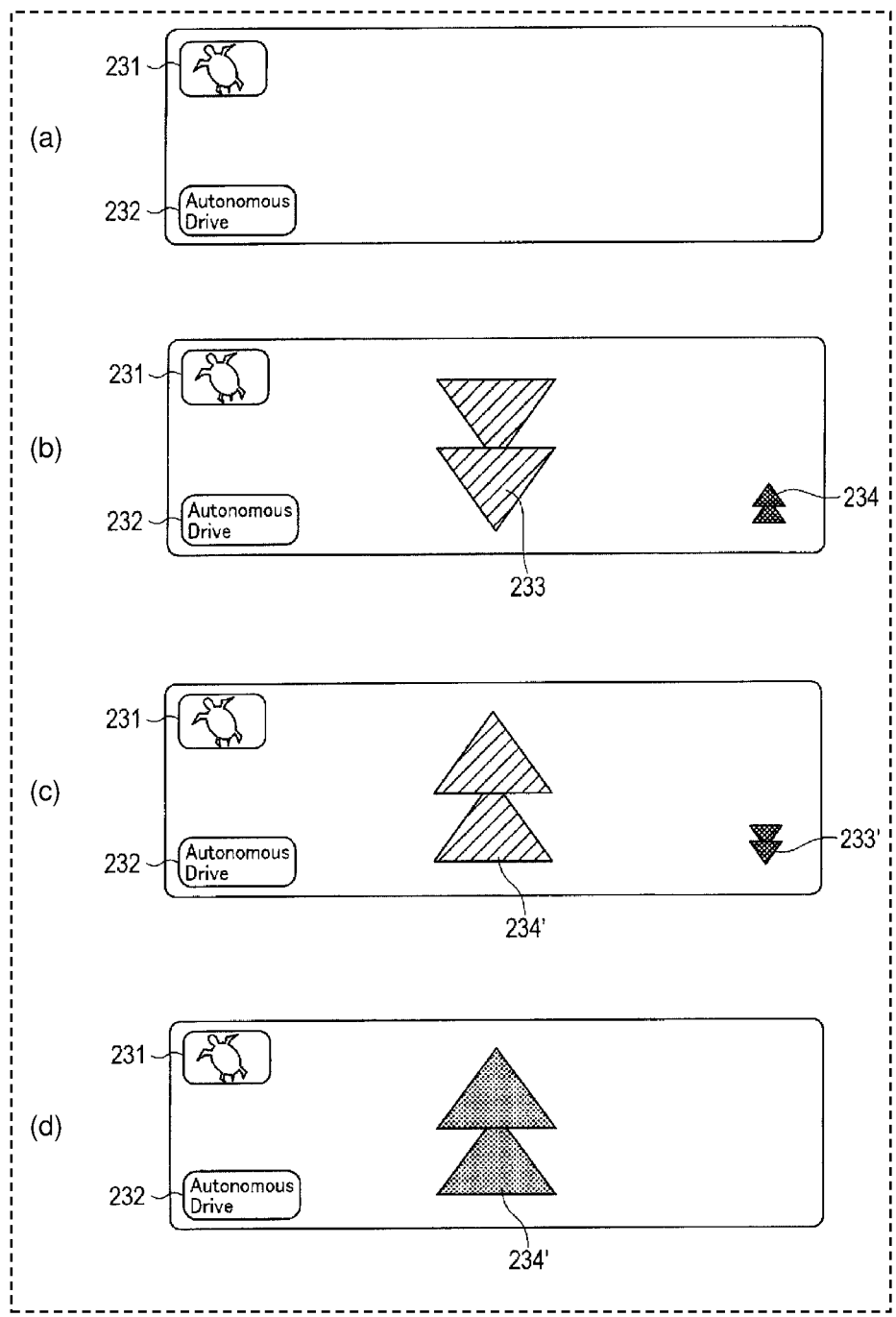
FIG. 24 is a view for describing a display on the notification unit according to the fourth exemplary embodiment of the present invention.

FIG. 24 is a view for describing a display on notification unit 92 according to the fourth exemplary embodiment of the present invention. FIG. 24 is a view illustrating a display in response to the second example of the travel environment illustrated in FIG. 7. It should be noted that constituent elements in FIG. 24 which are substantially identical to the constituent elements in FIG. 23 are denoted by the identical reference numerals used in FIG. 23 and will not be described in detail. FIG. 24 is formed by deleting symbol 235 indicating "lane change" from FIG. 23.

As mentioned previously, in the second example (FIG. 7), different from the first example (FIG. 5), a lane change is impossible because another vehicle is traveling on the right of vehicle 1. Therefore, "lane change" is not displayed in parts (b) and (c) of FIG. 24. Further, in the example in part (c) of FIG. 24, because "acceleration" is selected as in part (c) of FIG. 23, vehicle controller 7 reads characteristic amounts corresponding to the behavior of "acceleration" included in the driving characteristic model, and controls vehicle 1 such that vehicle 1 performs "acceleration" with these characteristic amounts being reflected thereon, as in part (c) of FIG. 23.

Figure 25:
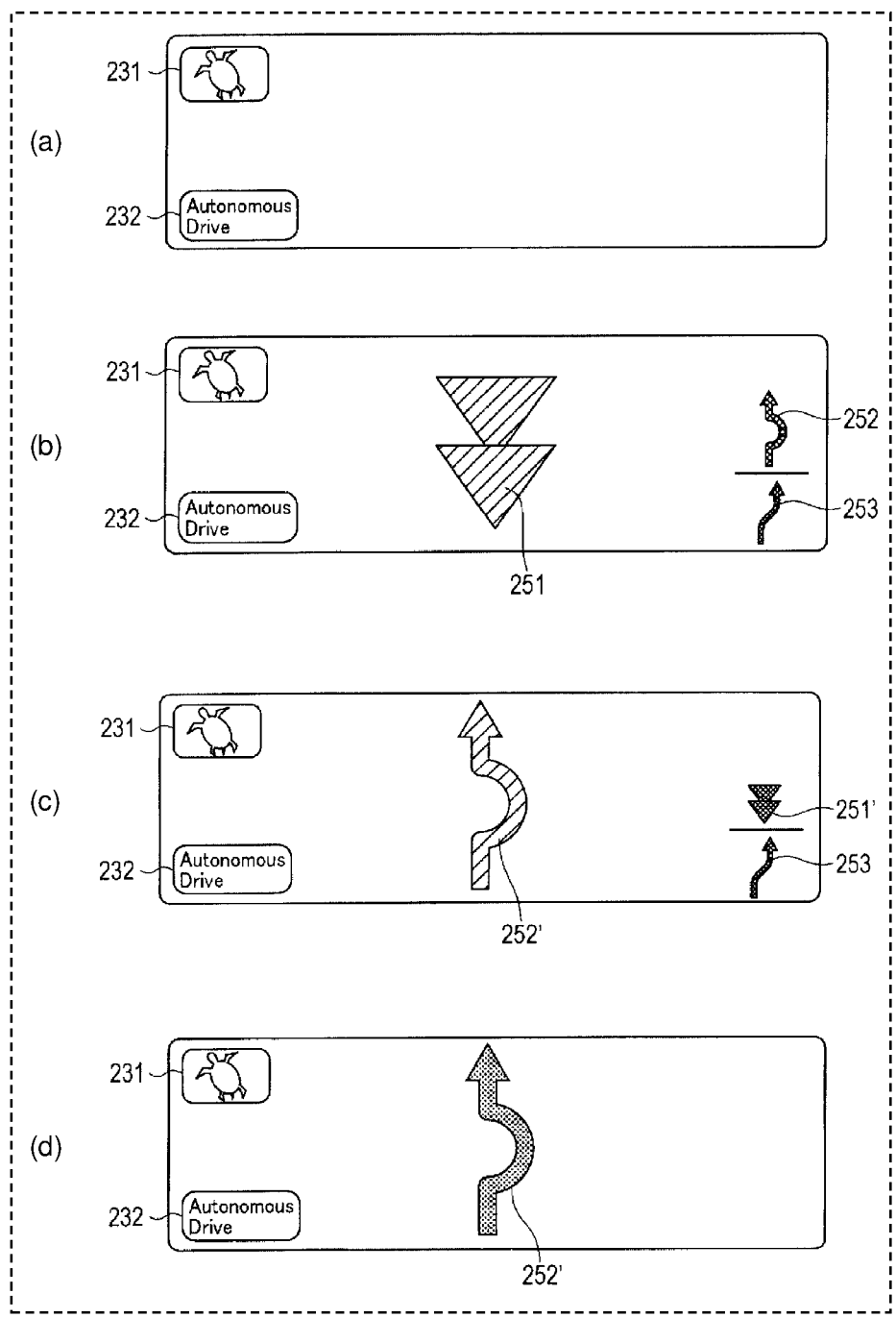
FIG. 25 is a view for describing a display on the notification unit according to the fourth exemplary embodiment of the present invention.

FIG. 25 is a view for describing a display on notification unit 92 according to the fourth exemplary embodiment of the present invention. FIG. 25 is a view illustrating a display in response to the third example of the travel environment illustrated in FIG. 8.

Part (a) of FIG. 25 is the same as part (a) of FIG. 23. When determining that the travel environment is the one in the third example illustrated in FIG. 8, vehicle controller 7 determines that the first behavior is "deceleration" based on the driver's driving characteristic of "frequently decelerating", and causes notification unit 92 to execute the display in part (b) of FIG. 25.

In part (b) of FIG. 25, symbol 251 indicating "deceleration" which is the first behavior is illustrated in the first manner (for example, in the first color). In addition, symbol 252 indicating "overtake" which is the second behavior and symbol 253 indicating "lane change" which is the second behavior are illustrated.

When the driver changes the behavior to the behavior of "overtake" by the operation described in the first exemplary embodiment, vehicle controller 7 causes notification unit 92 to execute the display in part (c) of FIG. 25.

In part (c) of FIG. 25, symbol 252' indicating "overtake" which is the selected behavior is illustrated in the first manner. Further, symbol 251 which has been displayed as the first behavior in part (b) of FIG. 25 is switched to symbol 252 and displayed as symbol 251'.

Then, vehicle controller 7 causes notification unit 92 to execute the display illustrated in part (d) of FIG. 25 when the second predetermined time has elapsed after vehicle controller 7 causes notification unit 92 to execute the display illustrated in part (a) of FIG. 25. In part (d) of FIG. 25, symbol 252' indicating "overtake" selected as the next behavior by the driver is displayed in the second manner.

When the behavior to be executed next is determined to be "overtake", vehicle controller 7 reads characteristic amounts corresponding to the behavior of "overtake" included in the driving characteristic model, and controls vehicle 1 such that vehicle 1 performs "acceleration" with these characteristic amounts being reflected thereon.

A description will next be given of an example of a display when the driving characteristic of the driver is not the driving characteristic of "frequently decelerating".

Figure 26:
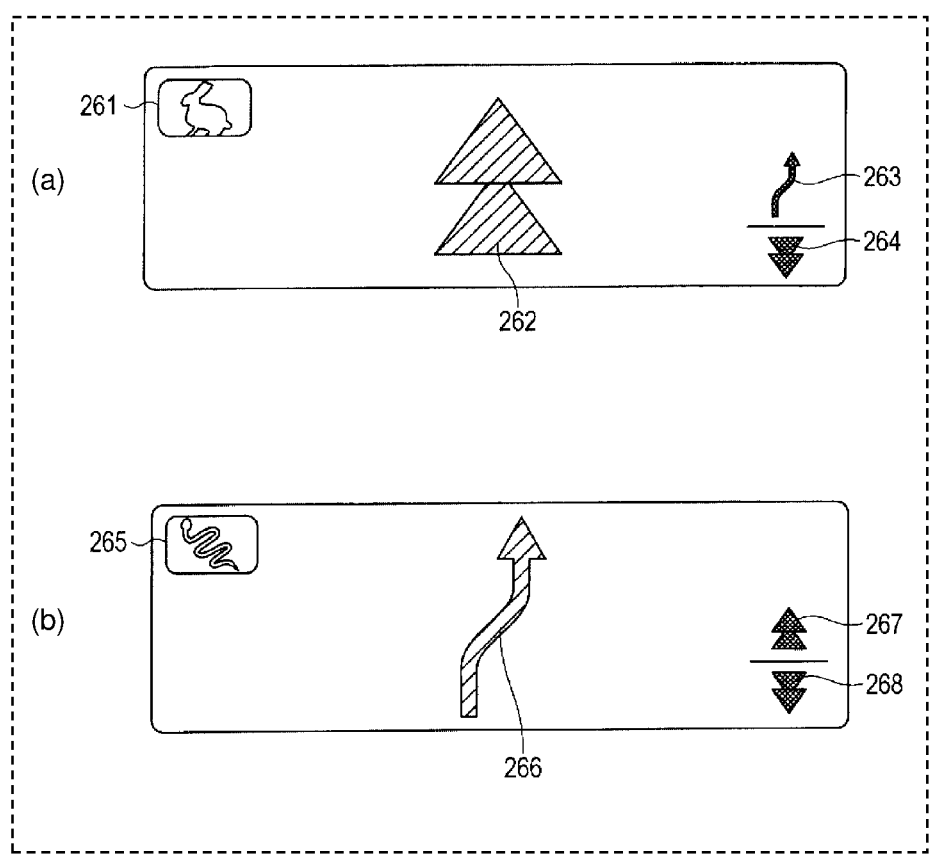
FIG. 26 is a view for describing a display on the notification unit according to the fourth exemplary embodiment of the present invention.

FIG. 26 is a view for describing a display on notification unit 92 according to the fourth exemplary embodiment of the present invention. FIG. 26 is a view illustrating a display in response to the first example of the travel environment illustrated in FIG. 5. It is to be noted that part (a) of FIG. 26 illustrates an example of a case where the driver has a driving characteristic of "frequently accelerating", and part (b) of FIG. 26 illustrates an example of a case where the driver has a driving characteristic of "frequently performing a lane change".

In part (a) of FIG. 26, symbol 261 indicating that the driver has a driving characteristic of "frequently accelerating" is illustrated. Symbol 262 indicating "acceleration" which is the first behavior is also illustrated in the first manner (for example, in the first color). In addition, symbol 263 indicating "lane change" which is the second behavior and symbol 264 indicating "deceleration" which is the second behavior are also illustrated.

Vehicle controller 7 causes notification unit 92 to execute a display including symbol 261 as illustrated in part (a) of FIG. 26 for the driver who has frequently "accelerated" previously (that is, the driver who has frequently selected the behavior of "acceleration" previously) based on the driving characteristic, for example. In addition, vehicle controller 7 determines the first behavior as "acceleration" and causes notification unit 92 to execute the display in part (a) of FIG. 26 based on the driver's driving characteristic of "frequently accelerating".

In part (b) of FIG. 26, symbol 265 indicating that the driver has a driving characteristic of "frequently performing a lane change" is illustrated. Symbol 266 indicating "lane change" which is the first behavior is also illustrated in the first manner (for example, in the first color). In addition, symbol 267 indicating "acceleration" which is the second behavior and symbol 268 indicating "deceleration" which is the second behavior are also illustrated.

Vehicle controller 7 causes notification unit 92 to execute a display including symbol 265 as illustrated in part (b) of FIG. 26 for the driver who has frequently performed "lane change" previously (that is, the driver who has frequently selected the behavior of "lane change" previously) based on the driving characteristic, for example. Vehicle controller 7 determines the first behavior as "lane change" and causes notification unit 92 to execute the display in part (b) of FIG. 26 based on the driver's driving characteristic of "frequently performing a lane change".

The description has been given only using the driving characteristic model. However, the driver model may also be considered, and symbol 231 in FIGS. 23 and 25, and symbols 261, 265 in FIG. 26 may indicate the type of the driver model selected from the operation history of the driver. For example, for the driver model to be applied to a driver frequently selecting "deceleration" for the first example of the travel environment illustrated in FIG. 5, vehicle controller 7 causes notification unit 92 to execute the display including symbol 231 as in FIG. 23 and determines the first behavior as "deceleration". For the driver model to be applied to a driver frequently selecting "acceleration", vehicle controller 7 causes notification unit 92 to execute the display including symbol 261 as in part (a) of FIG. 26 and determines the first behavior as "acceleration". For the driver model to be applied to a driver frequently selecting "lane change", vehicle controller 7 causes notification unit 92 to execute the display including symbol 265 as in part (b) of FIG. 26 and determines the first behavior as "lane change".

According to the present exemplary embodiment described above, when determining a future behavior of the vehicle, the vehicle can learn the previous travel history of the driver and reflect the result in determining the future behavior. In addition, when controlling the vehicle, vehicle controller can learn the driving characteristic (driving taste) of the driver and reflect the result in controlling the vehicle.

Thus, the vehicle can control the autonomous driving at a timing or with an operation amount favored by the driver or the occupant, thereby being capable of suppressing unnecessary operation intervention of the driver during the autonomous driving without causing deviation from a sense of the driver when he/she actually manually drives the vehicle.

Note that, in the present invention, the function similar to the function executed by vehicle controller 7 may be executed by a cloud server or a server device. In addition, storage unit 8 may be provided in the cloud server or the server device, not in vehicle 1. Alternatively, storage unit 8 may store a driver model which has already been constructed, and vehicle controller 7 may determine a behavior by referring to the driver model stored in storage unit 8.

As described above, in the fourth exemplary embodiment, vehicle controller 7 acquires the information about the characteristic amount indicating the driving characteristic of the driver; storage unit 8 stores the information about the characteristic amount; and vehicle controller 7 constructs, for each travel environment of the vehicle, the driver model which indicates the tendency of the behavior of the vehicle selected by the driver in terms of the frequency of the selected behavior, based on the information about the characteristic amount stored in storage unit 8.

In addition, vehicle controller 7 determines, among from a plurality of drivers, the group of the drivers having similar behavior selection, and constructs the driver model for each group or each travel environment of the vehicle.

Further, vehicle controller 7 calculates the average of the frequency of the behavior selected by each driver for each group of the drivers performing a similar operation, and constructs, for each travel environment of the vehicle, a driver model in which the tendency of the behavior of the vehicle selected by the driver is indicated in terms of the calculated average.

Moreover, vehicle controller 7 constructs, based on the vehicle behavior which is selected by another driver having a similar tendency to the vehicle behavior selected by a specific driver, a driver model in which the tendency of the vehicle behavior selected by the specific driver is indicated in terms of the frequency of each selected behavior, for each travel environment of the vehicle.

Accordingly, vehicle controller 7 can construct a driver model more suitable for the driving tendency of the driver, and can perform autonomous driving more appropriate for the driver based on the constructed driver model.

(Modification of Driver Model)

The driver model described above is constructed in such a way that the operation (behavior) tendency of a driver for each travel environment is modeled based on information relating to the frequency of each operation. However, the present invention is not limited thereto.

For example, the driver model may be constructed based on a travel history in which an environmental parameter indicating a travel environment (i.e., situation) through which the vehicle has previously traveled and the operation (behavior) actually selected by the driver in this travel environment are associated with each other. When the environmental parameter is incorporated into the driver model, options can be decided without going through the procedure for individually performing detection and labeling of the travel environment and inputting (storing) the labeling result in the driver model. Specifically, when the difference in travel environment as in FIGS. 23 and 24 is acquired as environmental parameters, and the acquired parameters are directly input (stored) in the driver model, "acceleration", "deceleration", and "lane change" are determined as options in FIG. 23, and "acceleration" and "deceleration" are determined as options in FIG. 24. Hereinafter, an example of constructing such a driver model will be described. Note that the driver model described below may be restated as a situation database.

Now, a travel history for constructing the driver model in the present modification will be described. FIG. 27 is a diagram illustrating one example of the travel history. FIG. 27 illustrates the travel history in which environmental parameters indicating a travel environment through which the vehicle driven by driver x has previously traveled and the operation (behavior) actually selected by the driver in this travel environment are associated with each other.

The environmental parameters in (a) to (c) in the travel history in FIG. 27 respectively indicate the travel environment when the vehicle behavior is presented to the driver as in part (b) of FIG. 8, part (b) of FIG. 5, and part (b) of FIG. 7, for example. The environmental parameters in the travel history are acquired from sensing information or infrastructure information.

The sensing information is information detected by sensors or radars in the vehicle. The infrastructure information includes information from GPS, map information, information acquired through road-to-vehicle communication, for example.

For example, the environmental parameters in the travel history in FIG. 27 include: "host vehicle information"; "leading vehicle information" indicating information about a vehicle traveling in front of host vehicle a in a lane of host vehicle a; "adjacent lane information" indicating information about an adjacent lane of the lane in which the host vehicle is traveling; "merging lane information" indicating, when there is a merging lane on a location where the host vehicle travels, the information about the merging lane; and "location information" indicating information about the location of the host vehicle and the surrounding thereof. In addition, following vehicle information may be included. In this case, a relative speed of the following vehicle relative to the host vehicle, head-to-head spacing, rate of change of the head-to-head spacing, and the like may be used. In addition, vehicle presence information may be included.

For example, the "host vehicle information" includes information about speed Va of the host vehicle. The "leading vehicle information" includes information about relative speed Vba of leading vehicle b relative to the host vehicle, distance DRba between the leading vehicle and the host vehicle, and rate of change RSb of the size of the leading vehicle.

Herein, speed Va of the host vehicle is detected by a speed sensor mounted to the host vehicle. Relative speed Vba and distance DRba between the host vehicle and the leading vehicle are detected by a sensor, radar, or the like. Rate of change RSb of the size is calculated from a relational expression of $RSb = -Vba/DRba$.

The "adjacent lane information" includes information about adjacent following vehicle c traveling behind the host vehicle in the adjacent lane, information about adjacent leading vehicle d traveling in front of the host vehicle in the adjacent lane, and information about remaining adjacent lane length DRda for the host vehicle.

The adjacent following vehicle information includes information about relative speed Vca of the adjacent following vehicle relative to the host vehicle, head-to-head spacing Dca between the adjacent following vehicle and the host vehicle, and rate of change Rca of the head-to-head spacing. Head-to-head spacing Dca between the adjacent following vehicle and the host vehicle is the distance between the front part (head) of the host vehicle and the front part (head) of the adjacent following vehicle measured in the direction along the travel direction of the host vehicle (and the adjacent following vehicle). Note that the head-to-head spacing may be calculated from the inter-vehicular distance or vehicle length. In addition, the head-to-head spacing may be replaced by the inter-vehicular distance.

Relative speed Vca and head-to-head spacing Dca are detected by a sensor, radar, or the like. Rate of change Rca of the head-to-head spacing is calculated from a relational expression of Rca=Vca/Dca.

In addition, the adjacent leading vehicle information includes information about relative speed Vda of the adjacent leading vehicle relative to the host vehicle, head-to-head spacing Dda between the adjacent leading vehicle and the host vehicle, and rate of change Rda of the head-to-head spacing. Head-to-head spacing Dda between the adjacent leading vehicle and the host vehicle is the distance between the front part (head) of the host vehicle and the front part (head) of the adjacent leading vehicle measured along the travel direction of the host vehicle (and the adjacent leading vehicle).

Relative speed Vda and head-to-head spacing Dda are detected by a sensor, radar, or the like. In addition, rate of change Rda of the head-to-head spacing is calculated from a relational expression of Rda=Vda/Dda.

Remaining adjacent lane length DRda for the host vehicle is a parameter indicating the degree of possibility of a lane change to the adjacent lane. Specifically, when the distance between the front part (head) of the host vehicle and the rear part of the adjacent leading vehicle measured along the travel direction of the host vehicle (and the adjacent leading vehicle) is longer than distance DRba between the leading vehicle and the host vehicle, remaining adjacent lane length DRda for the host vehicle is the distance between the front part (head) of the host vehicle and the rear part of the adjacent leading vehicle, and when the distance between the front part (head) of the host vehicle and the rear part of the adjacent leading vehicle is shorter than DRba, remaining adjacent lane length DRda is DRba. Remaining adjacent lane length DRda for the host vehicle is detected by a sensor, radar, or the like.

The "merging lane information" includes information about relative speed Vma of a merging vehicle relative to the host vehicle, head-to-head spacing Dma between the merging vehicle and the host vehicle, and rate of change Rma of the head-to-head spacing. Head-to-head spacing Dma between the merging vehicle and the host vehicle is the distance between the front part (head) of the host vehicle and the front part (head) of the merging vehicle measured in the direction along the travel direction of the host vehicle (and the merging vehicle).

Relative speed Vma and head-to-head spacing Dma are detected by a sensor, radar, or the like. Rate of change Rma of the head-to-head spacing is calculated from a relational expression of Rma=Vma/Dma.

In the example of the travel history illustrated in FIG. 27, the numerical values of the speed, distance, and rate of change described above are classified into a plurality of levels, and the numerical values indicating the classified levels are stored. Note that the numerical values of the speed, distance, and rate of change may be stored without being classified into levels.

The location information includes, for example, "host vehicle location information", "number of travel lanes", "host vehicle travel lane", "distance to start/end point of merging section", "distance to start/end point of branch section", "distance to start/end point of road work section", "distance to start/end point of lane end section", and "distance to accident spot". FIG. 27 illustrates, as examples of the location information, the "host vehicle travel lane" (travel lane in FIG. 27) and the "distance to start/end point of merging section".

For example, numerical information indicating the latitude and longitude acquired from the GPS is stored in the part of the "host vehicle location information". The number of travel lanes on the road where the host vehicle is traveling is stored in the part of the "number of travel lanes". Numerical information indicating the location of the lane where the host vehicle is traveling is stored in the part of the "host vehicle travel lane". When there are start and end points of a merging section within a predetermined distance, the distances to the start and end points of the merging section are classified into a plurality of predetermined levels, and the numerical values of the classified levels are stored in the part of the "distance to start/end point of merging section". When there are no start and end points of a merging section within the predetermined distance, "0" is stored in the part of the "distance to start/end point of merging section".

When there are start and end points of a branch section within a predetermined distance, the distances to the start and end points of the branch section are classified into a plurality of predetermined levels, and the numerical values of the classified levels are stored in the part of the "distance to start/end point of branch section". When there are no start and end points of a branch section within the predetermined distance, "0" is stored in the part of the "distance to start/end point of branch section". When there are start and end points of a road work section within a predetermined distance, the distances to the start and end points of the road work section are classified into a plurality of predetermined levels, and the numerical values of the classified levels are stored in the part of the "distance to start/end point of road work section". When there are no start and end points of a road work section within the predetermined distance, "0" is stored in the part of the "distance to start/end point of road work section".

When there are start and end points of a lane end section within a predetermined distance, the distances to the start and end points of the lane end section are classified into a plurality of predetermined levels, and the numerical values of the classified levels are stored in the part of the "distance to start/end point of lane end section". When there are no start and end points of a lane end section within the predetermined distance, "0" is stored in the part of the "distance to start/end point of lane end section".

When there is an accident spot within a predetermined distance, the distance to the accident spot is classified into a plurality of predetermined levels, and the numerical values of the classified levels are stored in the part of the "distance to accident spot". When there is no accident spot within the predetermined distance, "0" is stored in the part of the "distance to accident spot".

In addition, the location information may include information indicating which lane, out of all lanes on the road where the host vehicle is traveling, is the merging lane, the branch lane, the lane having a road work, the lane which ends, and the lane having an accident spot.

Note that the travel history illustrated in FIG. 27 is merely one example, and the present invention is not limited thereto. For example, when the adjacent lane information is information about the right adjacent lane, the travel history may further include "left adjacent lane information" opposite to the right adjacent lane.

The "left adjacent lane information" includes information about a left adjacent following vehicle traveling behind the host vehicle in the left adjacent lane, information about a left adjacent leading vehicle traveling in front of the host vehicle in the left adjacent lane, and information about remaining left adjacent lane length DRda for the host vehicle.

The left adjacent following vehicle information includes information about relative speed Vfa of the left adjacent following vehicle relative to the host vehicle, head-to-head spacing Dfa between the left adjacent following vehicle and the host vehicle, and rate of change Rfa of the head-to-head spacing. Head-to-head spacing Dfa between the left adjacent following vehicle and the host vehicle is the distance between the front part (head) of the host vehicle and the front part (head) of the left adjacent following vehicle measured in the direction along the travel direction of the host vehicle (and the left adjacent following vehicle).

Here, relative speed Vfa and head-to-head spacing Dfa are detected by a sensor, radar, or the like. In addition, rate of change Rfa of the head-to-head spacing is calculated from a relational expression of Rfa=Vfa/Dfa.

In addition, the left adjacent leading vehicle information includes information about relative speed Vga of the left adjacent leading vehicle relative to the host vehicle, head-to-head spacing Dga between the left adjacent leading vehicle and the host vehicle, and rate of change Rga of the head-to-head spacing. Head-to-head spacing Dga between the left adjacent leading vehicle and the host vehicle is the distance between the front part (head) of the host vehicle and the front part (head) of the left adjacent leading vehicle measured along the travel direction of the host vehicle (and the left adjacent leading vehicle).

Here, relative speed Vga and head-to-head spacing Dga are detected by a sensor, radar, or the like. In addition, rate of change Rga of the head-to-head spacing is calculated from a relational expression of Rga=Vga/Dga.

It is to be noted that, while the description has been given of the case where the vehicle is in the left side of the road, the similar process is also applied for the case where the vehicle is in the right side of the road by inverting left to right.

In addition, the travel history illustrated in FIG. 27 may include "following vehicle information" indicating information about a vehicle traveling behind the host vehicle in the travel lane of the host vehicle.

The following vehicle information includes information about relative speed Vea of the following vehicle relative to the host vehicle, head-to-head spacing Dea between the following vehicle and the host vehicle, and rate of change Rea of the head-to-head spacing. Head-to-head spacing Dea between the following vehicle and the host vehicle is the distance between the front part (head) of the host vehicle and the front part (head) of the following vehicle measured in the direction along the travel direction of the host vehicle (and the following vehicle).

Here, relative speed Vea and head-to-head spacing Dea are detected by a sensor, radar, or the like. Rate of change Rea of the head-to-head spacing is calculated from a relational expression of Rea=Vea/Dea.

It is to be noted that, if the head-to-head spacing cannot be measured because of the vehicles being hidden by a moving body, the measurable distance between vehicles or an approximate value obtained by adding a predetermined vehicle length to the distance between vehicles may be substituted for the head-to-head spacing, or the head-to-head spacing may be calculated by adding the vehicle length of each recognized vehicle type to the distance between vehicles. Alternatively, regardless of whether the head-to-head spacing can be measured, the measurable distance between vehicles or an approximate value obtained by adding a predetermined vehicle length to the distance between vehicles may be substituted for the head-to-head spacing, or the head-to-head spacing may be calculated by adding the vehicle length of each recognized vehicle type to the distance between vehicles.

The travel history may include various types of other information pertaining to the travel environment of the vehicle. For example, the travel history may include information about the size or the type of a leading vehicle, an adjacent vehicle, or a merging vehicle, and information about the relative position relative to the host vehicle. For example, when the vehicle approaching from behind is an emergency vehicle as a result of recognition of the type of the vehicle by a camera sensor, information indicating the vehicle being an emergency vehicle may be included. According to this configuration, notification regarding information for responding to the emergency vehicle can be provided. Alternatively, numerical values indicating, in stages, operation amounts of the steering wheel, the brake, and the accelerator or the information pertaining to a fellow passenger as described with reference to FIG. 22 may be included in the travel history.

In addition, the travel history of the driver may be formed by aggregating the behaviors selected during autonomous driving, or by aggregating the behaviors actually executed by the driver during manual driving. Thus, a travel history can be collected according to a driving state, i.e., autonomous driving or manual driving.

Further, although the environmental parameters included in the travel history in the example in FIG. 27 show the travel environment when a vehicle behavior is presented to the driver, the environmental parameters may show a travel environment when the driver performs behavior selection. Alternatively, the travel history may include both environmental parameters showing the travel environment when a vehicle behavior is presented to the driver and environmental parameters showing the travel environment when the driver performs behavior selection.

Moreover, the following configuration may be applied when vehicle controller 7 generates the display of the overhead view illustrated in part (a) of FIG. 2, part (a) of FIG. 5, part (a) of FIG. 6, part (a) of FIG. 7, part (a) of FIG. 8, part (a) of FIG. 9, or part (a) of FIG. 10 or the display illustrated in part (c) of FIG. 14. Specifically, vehicle controller 7 may generate, as one notification information item, the information about the environmental parameter having a high rate of contribution by which the first behavior and the second behavior are selected, and/or the information (for example, icon) pertaining to this environmental parameter, and may cause notification unit 92 to provide the generated notification information such that, for example, the generated notification information is displayed on the overhead view.

In this case, if distance DRba between the leading vehicle and the host vehicle or rate of change RSb of the size of the leading vehicle has a high rate of contribution, for example, vehicle controller 7 may cause notification unit 92 to display a high luminance region or a color-changed region between the leading vehicle and the host vehicle in the overhead view so as to provide the notification information.

Alternatively, vehicle controller 7 may display, as the notification information, an icon indicating that distance DRba or rate of change RSb has a high rate of contribution, in a region between the leading vehicle and the host vehicle. Still alternatively, vehicle controller 7 may cause notification unit 92 to depict, as the notification information, a line segment connecting the leading vehicle and the host vehicle in the overhead view, or to depict line segments connecting all surrounding vehicles and the host vehicle as the notification information and to highlight only the line segment connecting the leading vehicle and the host vehicle in the overhead view.

Alternatively, vehicle controller 7 may cause notification unit 92 to display, between the leading vehicle and the host vehicle, as the notification information, a region having higher luminance than the surrounding region or a region having a different color from the surrounding region, not in the overhead view, but in a viewpoint image viewed by the driver, thereby implementing augmented reality (AR) display. Alternatively, vehicle controller 7 may cause notification unit 92 to display in the viewpoint image, as the notification information, an AR image of an icon indicating an environmental parameter having a high rate of contribution in a region between the leading vehicle and the host vehicle.

Still alternatively, vehicle controller 7 may cause notification unit 92 to display in the viewpoint image, as the notification information, an AR image of a line segment connecting the leading vehicle and the host vehicle, or to display in the viewpoint image, as the notification information, an AR image of line segments connecting all surrounding vehicles and the host vehicle and to highlight only the line segment connecting the leading vehicle and the host vehicle.

It should be noted that the method for providing notification regarding the environmental parameter having a high rate of contribution or the information pertaining to the environmental parameter is not limited to the methods described above. For example, vehicle controller 7 may generate, as the notification information, an image in which the leading vehicle involved with an environmental parameter having a high rate of contribution is displayed in a highlighted manner, and may cause notification unit 92 to display this image.

In addition, vehicle controller 7 may generate, as the notification information, information indicating the direction of the leading vehicle or the like involved with an environmental parameter having a high rate of contribution in the overhead view or AR display, and display this information in the host vehicle or around the host vehicle.

Alternatively, in place of providing the notification regarding the information about the environmental parameter having a high rate of contribution or the information pertaining to this environmental parameter, vehicle controller 7 may make a leading vehicle or the like which is involved with an environmental parameter having a low rate of contribution unnoticeable by lowering the display luminance of the leading vehicle or the like, generate, as the notification information, the information about the environmental parameter having a high rate of contribution which becomes relatively noticeable or the information pertaining to the environmental parameter, and cause notification unit 92 to display the generated information, for example.

Next, the construction of a driver model based on the travel history of the driver will be described. The driver model is classified into a clustering type constructed by clustering travel histories of a plurality of drivers, and an individually-adapted type in which a driver model of a specific driver (for example, driver x) is constructed from a plurality of travel histories similar to the travel history of driver x.

Firstly, the clustering type will be described. The clustering-type driver model is constructed in such a way that the travel history of the driver illustrated in FIG. 27 is aggregated in advance for each driver. Then, a plurality of drivers having a high degree of similarity between the travel histories, that is, a plurality of drivers having a similar driving operation tendency, is grouped to construct a driver model.

The degree of similarity between travel histories can be determined, for example, based on a correlation value of a vector having, when the behaviors in the travel histories of driver a and driver b are quantified according to a predetermined rule, the numerical value of the environmental parameter and the numerical value of the behavior as an element. In this case, when the correlation value calculated from the travel histories of driver a and driver b is higher than a predetermined value, for example, the travel histories of driver a and driver b are grouped into a single group. Note that the calculation of the degree of similarity is not limited thereto.

Next, the individually-adapted type will be described. The individually-adapted-type driver model is constructed in such a way that travel histories of a plurality of drivers illustrated in FIG. 27 are aggregated in advance, as in the method for constructing the clustering-type. The different point from the clustering-type is such that the driver model is constructed for each driver. For example, when a driver model is constructed for driver y, the travel history of driver y and travel histories of the other drivers are compared, and the travel histories of the drivers having a high degree of similarity are extracted. Then, the individually-adapted-type driver model for driver y is constructed from the extracted travel histories of a plurality of drivers.

Notably, the driver model (situation database) based on the travel history in FIG. 27 is not limited to the clustering type or the individually-adapted type, and may be constructed to include travel histories of all drivers, for example.

Now, a method for using the constructed driver model will be described with examples. A description will next be given of a case where a driver model formed by aggregating travel histories of four drivers a to d is used for driver x. Note that the driver model is constructed by vehicle controller 7.

FIG. 28 is a diagram illustrating a method for using the driver model in the present modification. Part (a) of FIG. 28 illustrates environmental parameters indicating the current travel environment of the vehicle driven by driver x. Part (b) of FIG. 28 illustrates one example of a driver model for driver x.

As illustrated in part (a) of FIG. 28, the behavior (operation) for the environmental parameters indicating the current travel environment is blank. Vehicle controller 7 acquires environmental parameters at predetermined intervals, and determines the next behavior from the driver model illustrated in part (b) of FIG. 28 by using any one of the environmental parameters as a trigger.

For example, the environmental parameter indicating the need to change the operation of the vehicle, such as the case where the distance to the start point of the merging section becomes shorter than or equal to a predetermined distance or the case where the relative speed relative to the leading vehicle becomes less than or equal to a predetermined value, may be used as a trigger.

Vehicle controller 7 compares the environmental parameters illustrated in part (a) of FIG. 28 with the environmental parameters in the travel history of the driver model illustrated in part (b) of FIG. 28, and determines the behavior associated with the most similar environmental parameters as the first behavior. In addition, vehicle controller 7 determines some behaviors associated with the other similar environmental parameters as the second behavior.

The similarity between environmental parameters can be determined from a correlation value of a vector having the numerical values of the environmental parameters as elements. For example, when the correlation value calculated from the vector having the numerical values of the environmental parameters illustrated in part (a) of FIG. 28 as an element and the vector having the numerical values of the environmental parameters in part (b) of FIG. 28 as an element is larger than a predetermined value, these environmental parameters are determined to be similar to each other. Note that the method for determining similarity between environmental parameters is not limited thereto.

In the above, a behavior is determined based on the degree of similarity between environmental parameters. However, for example, a group of environmental parameters having a high degree of similarity may be firstly generated, statistics of the environmental parameters in this group may be taken, and a behavior may be determined from this statistical data.

In this way, the notification regarding the behavior more suitable for the driver can be provided by constructing in advance the driver model for each driver from the travel histories of a plurality of drivers. Notably, to register a safer travel history into a database, it may be configured such that: storage unit 8 stores information indicating a safe travel standard; vehicle controller 7 determines whether or not the travel history satisfies this standard; and vehicle controller 7 further registers the travel history satisfying this standard into the database and does not register the travel history not satisfying this standard.

In addition, due to the association between the parameter indicating the travel environment and the behavior, vehicle controller 7 can determine the next behavior with high accuracy without determining a specific travel environment, i.e., without performing labeling of travel environments.

It is to be noted that the driver model (situation database) may be constructed from the travel history in which the behavior selected by the driver during autonomous driving and the environmental parameters indicating the travel environment when this behavior is presented are associated with each other. Alternatively, the driver model (situation database) may be constructed from the travel history in which the behavior selected by the driver during autonomous driving and the environmental parameters indicating the travel environment when the vehicle performs this behavior are associated with each other.

When the environmental parameters indicate the travel environment when the vehicle performs the behavior selected by the driver, the following configuration may be applied. Specifically, environmental parameters indicating a future travel environment are predicted from the environmental parameters indicating the current travel environment. Then, from among the environmental parameters indicating the travel environment when the vehicle performs the behavior selected by the driver, the behavior associated with the environmental parameter most similar to the predicted environmental parameters may be determined as the first behavior, and some behaviors associated with the other similar environmental parameters may be determined as the second behavior.

For example, the above prediction is conducted by extrapolating the environmental parameters in the future from the environmental parameters indicating the travel environments at the present moment and before the present moment.

Alternatively, the driver model (situation database) may be constructed from both the travel history in which the behavior selected by the driver during autonomous driving and the environmental parameters indicating the travel environment when this behavior is presented are associated with each other, and the travel history in which the behavior selected by the driver during autonomous driving and the environmental parameters indicating the travel environment when the vehicle performs this behavior are associated with each other.

In this case, both of the travel histories are stored in the form illustrated in part (b) of FIG. 28, for example, and vehicle controller 7 determines the next behavior from these travel histories. In this case, vehicle controller 7 may place priority between these travel histories, and may preferentially determine the next behavior from the travel history in which the behavior selected by the driver during autonomous driving and the environmental parameters indicating the travel environment when the vehicle performs this behavior are associated with each other, for example.

Note that, in the present invention, the function similar to the function executed by vehicle controller 7 may be executed by a cloud server or a server device. Particularly, storage unit 8 may be mounted in a server device such as a cloud server, not in vehicle 1, because it has an enormous amount of data with accumulation of travel histories. Alternatively, storage unit 8 may store a driver model which has already been constructed, and vehicle controller 7 may determine a behavior by referring to the driver model stored in storage unit 8.

It is to be noted that, in the configuration in which storage unit 8 is mounted in a cloud server, a cache is desirably provided in case of storage unit 8 being inaccessible due to a drop in a communication speed or disruption of communication.

Figure 29:
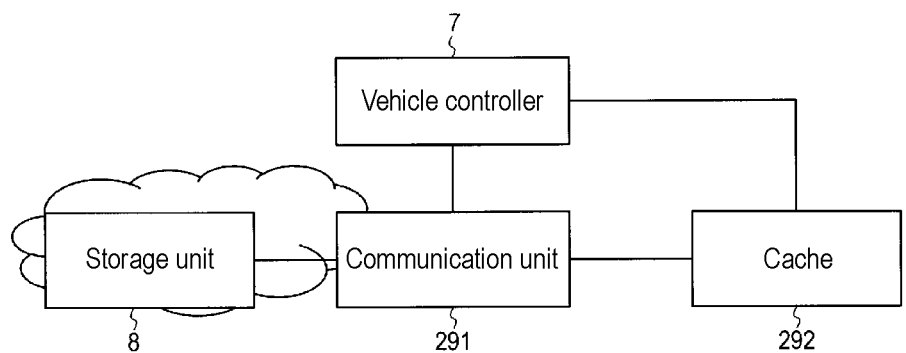
FIG. 29 is a block diagram illustrating one example of a cache arrangement in the present modification.

FIG. 29 is a block diagram illustrating one example of a cache arrangement. Vehicle controller 7 causes storage unit 8 to store the travel history through communication unit 291, and causes cache 292 to store a portion of the driver model (situation database) stored in storage unit 8 through communication unit 291.

Vehicle controller 7 accesses the driver model in cache 292. Conceivable methods for creating a cache in this case include a method for limitation according to presence or absence of an environmental parameter, a method using location information, and a method for processing data. Each of the methods will be described below.

Firstly, the method for limitation according to presence or absence of an environmental parameter will be described. It is possible to extract similar situations through comparison with surrounding situations, if there are sufficient travel environments (situations) having only the same environmental parameters. Therefore, vehicle controller 7 extracts travel environments having only the same environmental parameters from among the travel environments stored in storage unit 8, sorts these travel environments, and holds the resultant in cache 292.

In this case, vehicle controller 7 updates a primary cache at the timing at which the environmental parameters acquired from the detected situation are changed. According to this process, vehicle controller 7 can extract similar surrounding conditions even if the communication speed drops. Notably, the environmental parameters which are determined to be changed may be all environmental parameters or some of the environmental parameters described previously.

Moreover, because the environmental parameters vary from hour to hour, a primary cache and a secondary cache may be prepared in cache 292. For example, vehicle controller 7 holds travel environments having the same environmental parameters in the primary cache. Further, vehicle controller 7 holds, in the secondary cache, a travel environment in which one environmental parameter is added to the travel environment held in the primary cache and/or a travel environment in which one environmental parameter is reduced from the travel environment held in the primary cache.

Accordingly, vehicle controller 7 can extract a similar situation only by using the data in cache 292, even if temporal communication disruption occurs.

Figure 30:
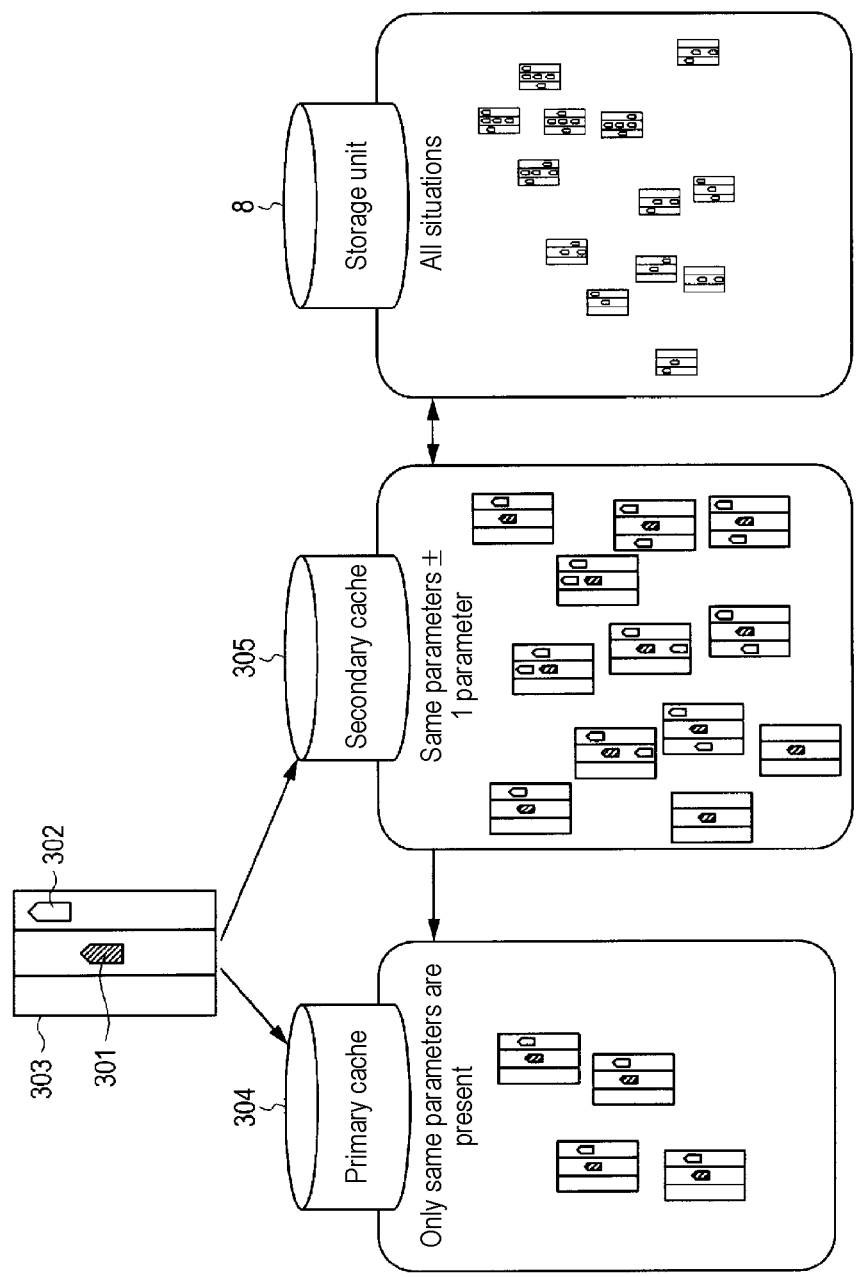
FIG. 30 is a diagram illustrating one example of a method for generating a cache in the present modification.

This case will be more specifically described with reference to FIG. 30. When sensor 62 detects surrounding situation 303 in which only adjacent leading vehicle 302 is present around host vehicle 301, vehicle controller 7 extracts travel environments (travel environments having the same environmental parameters) where only adjacent leading vehicle 302 is present, from storage unit 8 in which all travel environments (situations) are stored, and stores the extracted travel environments in primary cache 304.

In addition, vehicle controller 7 extracts a travel environment where only one vehicle other than adjacent leading vehicle 302 is added (travel environment where one environmental parameter is added to the same environmental parameter) or a travel environment where there is no adjacent leading vehicle 302 (travel environment where one environmental parameter is reduced from the same environmental parameters) from storage unit 8, and stores the extracted travel environments in secondary cache 305.

When surrounding situation 303 detected by sensor 62 is changed, vehicle controller 7 copies the travel environment corresponding to changed surrounding situation 303 to primary cache 304 from secondary cache 305, extracts, from storage unit 8, a travel environment where one environmental parameter is added and a travel environment where one environmental parameter is reduced relative to the travel environment corresponding to changed surrounding situation 303, and stores the extracted travel environments into secondary cache 305. Thus, vehicle controller 7 updates secondary cache 305. Accordingly, vehicle controller 7 can smoothly extract more similar surrounding situations through comparison with the surrounding situations.

Next, the method using location information will be described. When location information is included in environmental parameters, vehicle controller 7 can extract, from storage unit 8, the travel environment (situation) where the location indicated by the location information is included within a certain range around the location of the host vehicle, and store the extracted travel environment in cache 292.

In this case, vehicle controller 7 updates cache 292 when the location indicated by the location information corresponding to the travel environment falls outside the certain range. Accordingly, vehicle controller 7 can extract a similar surrounding situation as long as the location falls within a certain range, even if long-term communication disruption occurs.

In addition, the method for processing data will be described. Operation histories including environmental parameters are accumulated in storage unit 8. Vehicle controller 7 divides the respective environmental parameters for each predetermined range to form a mesh on a multidimensional space. Then, vehicle controller 7 creates a table in which behaviors included in each mesh are counted for each type.

A description will be given of the case where the environmental parameters to be used are limited to two, for example. Vehicle controller 7 maps the environmental parameters included in the operation history on a plane as illustrated in part (a) of FIG. 31, and each axis is equally divided, whereby the plane is divided into a plurality of blocks. This is called a mesh.

Figure 31:
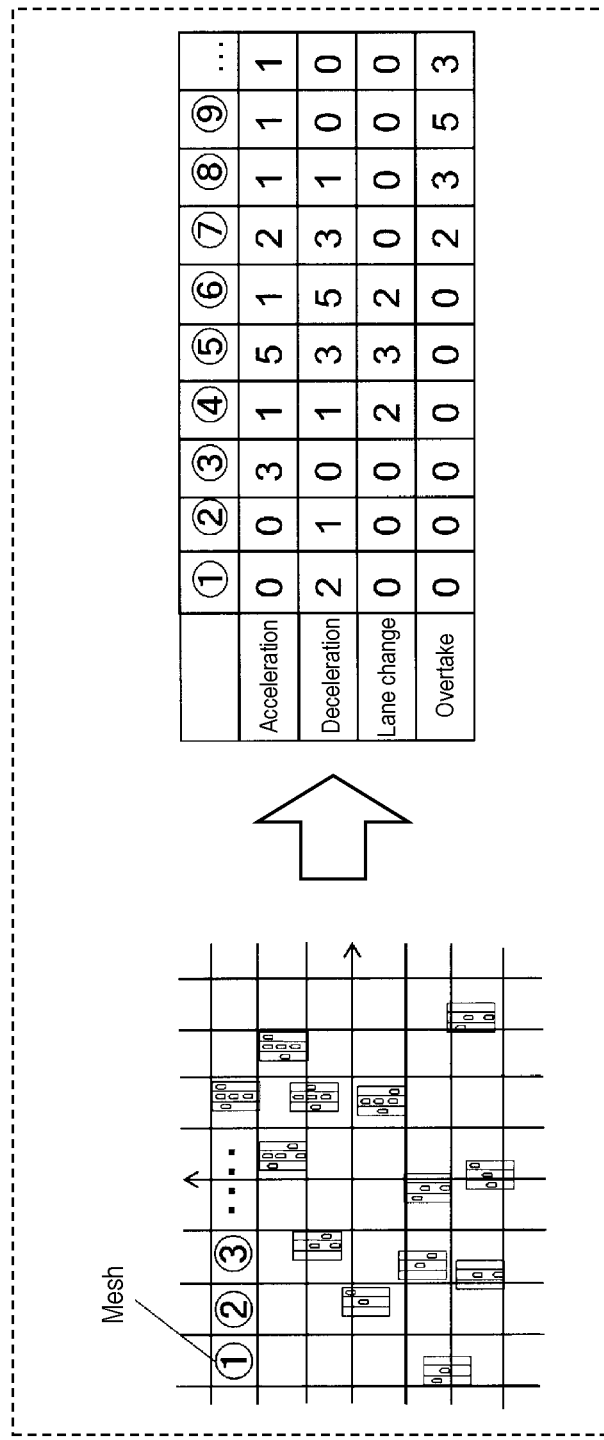
FIG. 31 is a diagram illustrating one example of the method for generating a cache in the present modification.

Vehicle controller 7 counts the number of behaviors included in each mesh for each type (for example, the type such as acceleration, deceleration, lane change, or overtake). Part (b) of FIG. 31 illustrates a table where the number of behaviors included in each mesh is counted for each type.

Vehicle controller 7 stores this content in cache 292. Then, when extracting a similar surrounding situation through the comparison with surrounding situations, vehicle controller 7 determines in which mesh the detected environmental parameter is located, selects the behavior having the highest number from the behaviors included in the determined mesh, and determines the selected behavior as the behavior to be provided as notification.

For example, when determining that the detected environmental parameter is in No. 3mesh, vehicle controller 7 determines operation of the behavior (here, "acceleration") showing the highest number among the behaviors included in the No. 3 mesh as the behavior to be provided as notification. If this method is used, cache 292 can be updated at any timing, and the capacity of cache 292 can be made constant.

The cache is created by using one of these methods or a combination thereof. It is to be noted that the methods described above are merely one example, and the method for creating a cache is not limited thereto.

As described above, in the example of extending the driver model in the fourth exemplary embodiment, vehicle controller 7 acquires information about characteristic amounts indicating a driver's driving characteristic including information about a previous travel environment, storage unit 8 stores the information about the characteristic amounts, and when it is determined that a vehicle behavior is needed to be changed, vehicle controller 7 determines information similar to characteristic amounts indicating the driver's driving characteristic including information about a newly-acquired travel environment, from the information about characteristic amounts stored in storage unit 8, and provides notification regarding the behavior corresponding to the determined information.

In addition, in the example of extending the driver model according to the fourth exemplary embodiment, the information about characteristic amounts indicating the driver's driving characteristic including the information about the previous travel environment is information about characteristic amounts when a vehicle behavior is presented to the driver and/or information about characteristic amounts when the driver performs behavior selection.

In addition, in the example of extending the driver model according to the fourth exemplary embodiment, when the information about characteristic amounts indicating the driver's driving characteristic including the information about the previous travel environment is both the information about characteristic amounts when a vehicle behavior is presented to the driver and the information about characteristic amounts when the driver performs behavior selection, vehicle controller 7 determines information similar to characteristic amounts indicating the driver's driving characteristic including information about a newly-acquired travel environment, from both information items about characteristic amounts, and provides notification regarding the behavior corresponding to the determined information.

In addition, in the example of extending the driver model according to the fourth exemplary embodiment, when the information about characteristic amounts indicating the driver's driving characteristic including the information about the previous travel environment is both the information about characteristic amounts when a vehicle behavior is presented to the driver and the information about characteristic amounts when the driver performs behavior selection, vehicle controller 7 determines information similar to characteristic amounts indicating the driver's driving characteristic including information about a newly-acquired travel environment, preferentially from the information about characteristic amounts when the driver performs behavior selection, and provides notification regarding the behavior corresponding to the determined information.

In addition, in the example of extending the driver model according to the fourth exemplary embodiment, the information about characteristic amounts indicating the driver's driving characteristic including the information about the previous travel environment is information about characteristic amounts indicating the driver's driving characteristic when the vehicle is under one or both of autonomous driving and manual driving.

Accordingly, vehicle controller 7 can construct a driver model more suitable for the driving tendency of the driver, and can perform autonomous driving more appropriate for the driver based on the constructed driver model. Due to the association between parameters indicating the travel environment and the behavior, vehicle controller 7 can determine the next behavior with high accuracy without requiring a process for determining a specific travel environment, i.e., without performing labeling of travel environments.

(Fifth Exemplary Embodiment)

Hereinafter, a fifth exemplary embodiment will be described. The above-mentioned exemplary embodiments have described a method for estimating a driver's driving action. On the other hand, the present exemplary embodiment will describe vehicle speed control, inter-vehicular distance control, and acceleration rate control. Regarding a vehicle speed, an inter-vehicular distance, and an acceleration rate, driving characteristics (habit in driving) of a driver during manual driving are collected, and the collected characteristics are reflected during autonomous driving.

Figure 32:
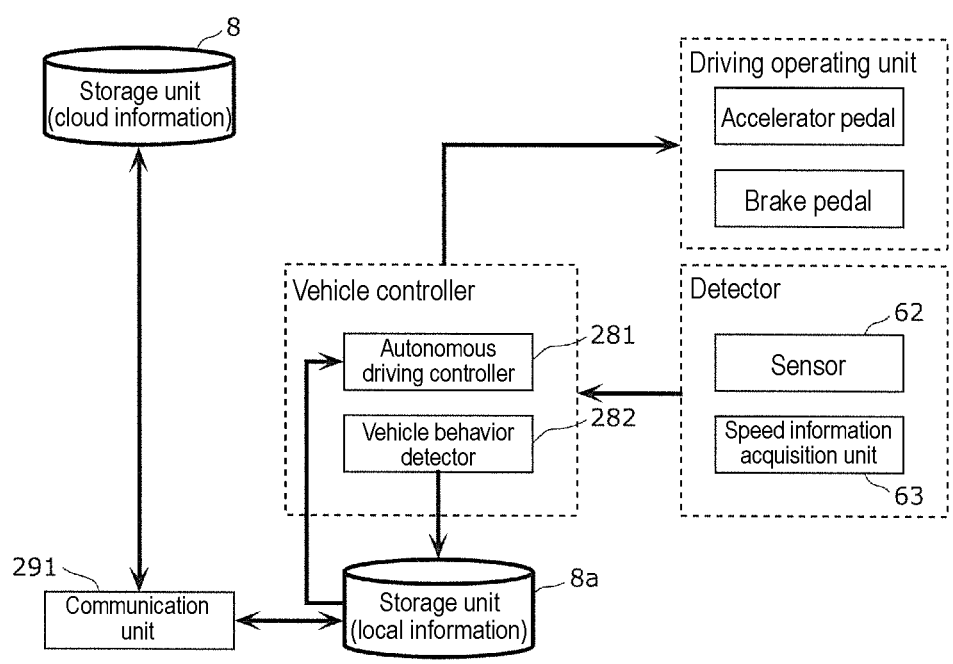
FIG. 32 is a block diagram illustrating a configuration of a main part for estimating a vehicle speed, an inter-vehicular distance, and an acceleration rate according to a fifth exemplary embodiment.

This will be described in more details with reference to FIG. 32. Firstly, a method for collecting data during manual driving will be described.

(Collection of Vehicle Speed)

Figure 33:
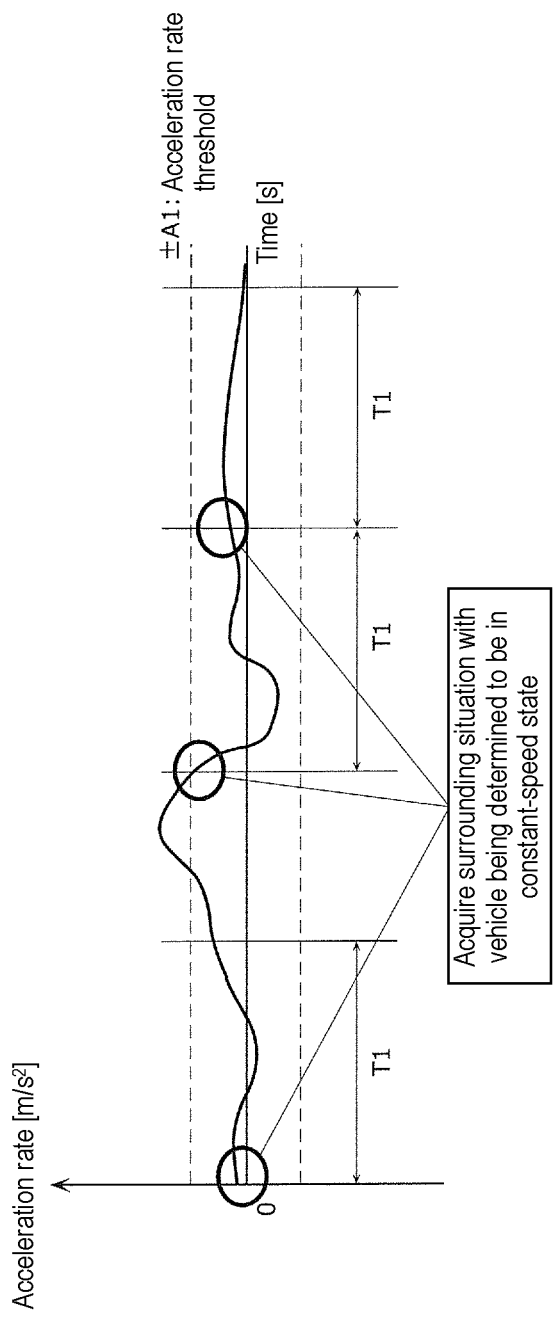
FIG. 33 is a diagram illustrating a timing at which a vehicle speed and an environmental parameter are collected in the fifth exemplary embodiment.

Vehicle behavior detector 282 in the present exemplary embodiment acquires speed information (vehicle speed) of the host vehicle from speed information acquisition unit 63 during manual driving, and detects the presence/absence of a leading vehicle by sensor 62. When detecting that no leading vehicle is detected and the host vehicle is turned into a constant-speed travel state, vehicle behavior detector 282 stores the vehicle speed and the environmental parameters at this moment into storage units 8, 8a. For example, as illustrated in FIG. 33, vehicle behavior detector 282 obtains a speed change, that is, an acceleration rate, and determines a travel state where the state in which the acceleration rate falls within a certain range (threshold ±A1) continues for T1 second as a constant-speed travel state. Then, vehicle behavior detector 282 acquires the vehicle speed and the environmental parameters upon the start of the constant-speed travel state, stores the obtained speed and parameters into storage units 8, 8a, and again starts searching the constant-speed travel state. By repeating such a process, vehicle behavior detector 282 accumulates information into storage units 8, 8a. The environmental parameters are the parameters described in the fourth exemplary embodiment, and they are inter-vehicular distances and relative change rates with vehicles around the host vehicle, a number of lanes, a lane position, a lane width, and a road condition. The lane width is a value of the width of the lane acquired by a sensor or an infrastructure, and the road condition is indicated by a value of showing how slippery the road surface is acquired by a sensor or an infrastructure (for example, 0=normal condition, 1=rainy weather, and 2=icy condition).

(Collection of Inter-vehicular Distance)

Figure 34:
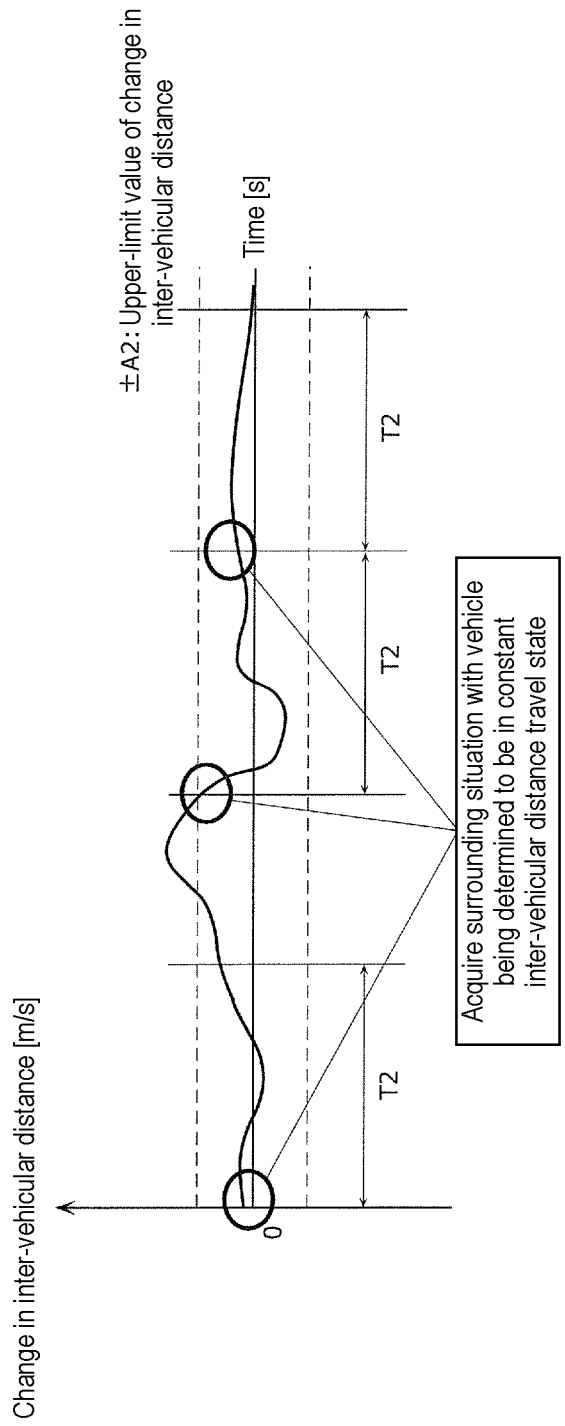
FIG. 34 is a diagram illustrating a timing at which an inter-vehicular distance and an environmental parameter are collected in a sixth exemplary embodiment.

Further, as described above, vehicle behavior detector 282 acquires speed information of the host vehicle from speed information acquisition unit 63 during manual driving, and detects the presence/absence of a leading vehicle by sensor 62. When detecting that there is a leading vehicle and that the host vehicle is turned into a constant inter-vehicular distance travel state, vehicle behavior detector 282 stores the inter-vehicular distance and the environmental parameters at this moment into storage units 8, 8a. For example, as illustrated in FIG. 34, vehicle behavior detector 282 obtains a change in the inter-vehicular distance, and when the state where the change in the inter-vehicular distance falls within a certain range (threshold ±A2) is continued for T2 second, vehicle behavior detector 282 determines that the vehicle is turned into the constant inter-vehicular distance travel state. Then, vehicle behavior detector 282 acquires the distance between the host vehicle and the leading vehicle and the environmental parameters upon the start of the constant inter-vehicular distance travel state, stores the obtained distance and parameters into storage units 8, 8a, and again starts searching the constant inter-vehicular distance travel state. By repeating such a process, vehicle behavior detector 282 accumulates information into storage units 8, 8a. The environmental parameters in this case are the speed of the host vehicle, inter-vehicular distances and relative change rates with vehicles around the host vehicle (note that the distance between the host vehicle and the leading vehicle is excluded), a number of lanes, a lane position, a lane width, and a road condition.

(Collection of Acceleration Rate)

Figure 35:
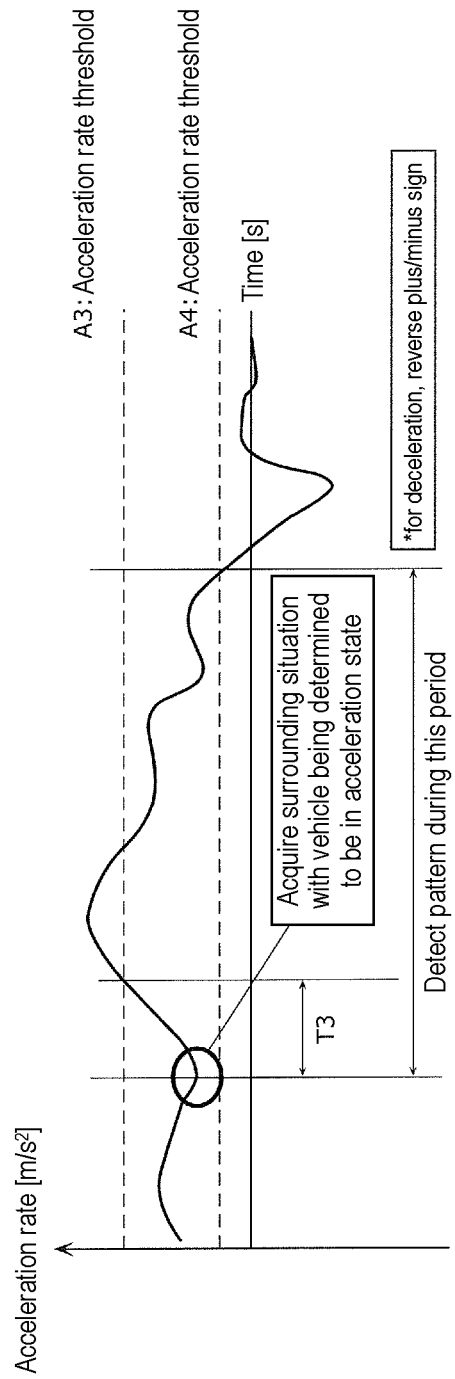
FIG. 35 is a diagram illustrating a timing at which an acceleration rate and an environmental parameter are collected in the fifth exemplary embodiment.
Figure 36:
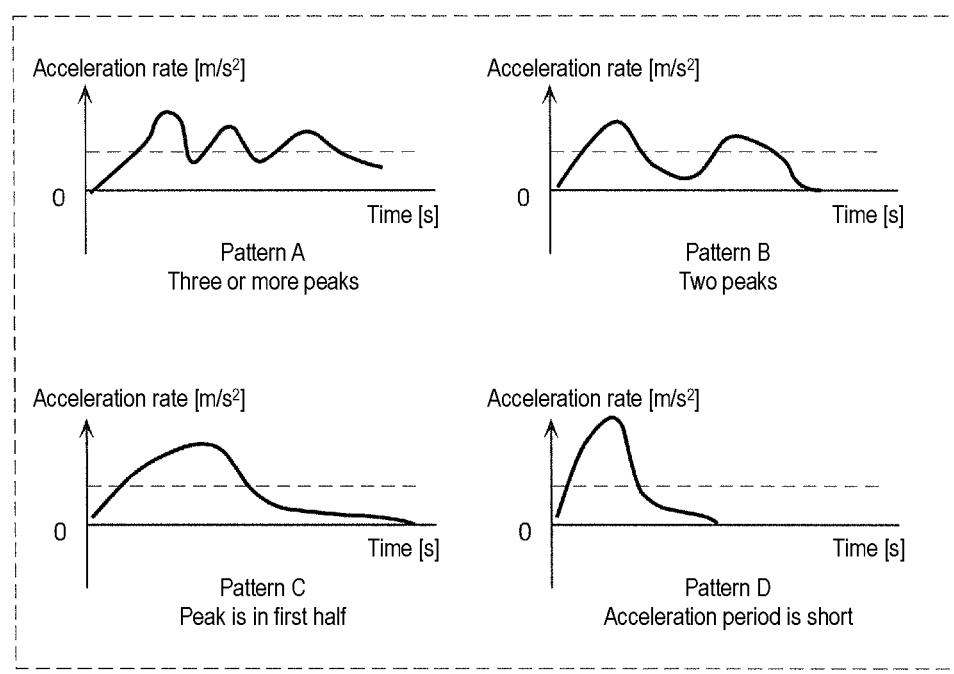
FIG. 36 is a diagram illustrating an example of an acceleration rate pattern in the fifth exemplary embodiment.

In addition, vehicle behavior detector 282 acquires speed information of the host vehicle from speed information acquisition unit 63 during manual driving, and detects the presence/absence of a leading vehicle by sensor 62. When detecting acceleration with an acceleration rate equal to or larger than a certain acceleration rate or deceleration with an acceleration rate equal to or less than a certain acceleration rate, vehicle behavior detector 282 stores acceleration rate patterns before and after the acceleration/deceleration into storage units 8, 8a together with the environmental parameters. For example, as illustrated in FIG. 35, vehicle behavior detector 282 acquires the environmental parameters at the time T3 second before the time when the acceleration rate exceeds a certain threshold A3 as well as the acceleration rate pattern until the acceleration rate exceeds threshold A4 or until the speed becomes zero (when the vehicle decelerates), and stores the obtained parameters and pattern into storage units 8, 8a. The environmental parameters during deceleration are the speed of the host vehicle, inter-vehicular distances and relative change rates with vehicles around the host vehicle (note that the distance between the host vehicle and the leading vehicle is excluded), a number of lanes, a lane position, a lane width, a road condition, a distance to a target stop position (when the vehicle is about to stop), a distance to a next traffic signal, and a lighting state of a traffic signal. The distance to a target stop position is the distance to a target stop position when an autonomous driving system determines to stop, and in other cases, it is set to be zero. The distance to a next traffic signal is set to an actual distance to a next traffic signal when the distance to the next traffic signal is equal to or less than a certain value, and in other cases, it is set to be zero. The lighting state of a traffic signal is set such that (red=0, yellow=1, green=2), for example. It is to be noted that, as illustrated in FIG. 36, the acceleration rate pattern is a pattern classified according to an acceleration or deceleration period, a position of a peak of an acceleration rate, and a number of peaks, for example. Alternatively, the acceleration rate pattern indicates an average acceleration rate during deceleration or acceleration, a period in which the acceleration rate exceeds a certain threshold in such an acceleration or deceleration period, and a speed at that time.

When autonomous driving is set by a driver, autonomous driving controller 281 controls the vehicle speed, inter-vehicular distance, and acceleration rate of the vehicle according to a surrounding situation by using the information items (FIGS. 37 and 38) stored in storage units 8, 8a. The control method therefor is similar to the method in the fourth exemplary embodiment, wherein a client uploads in advance the data stored in storage unit 8a to a cloud through communication unit 291. The cloud compares the driving characteristic with the driving characteristics of other drivers, and creates a driver model based on a group of drivers having similar driving characteristics. In this case, a driver model may individually be created for each of the vehicle speed, the inter-vehicular distance, and the acceleration rate, or a driver model including all of these parameters may be created. The created driver model is transmitted to the client. These processes are performed at a timing such as just after an engine is started.

The driver model may be created according to the method described in the fourth exemplary embodiment. In addition, a model with environmental parameters being an input and a vehicle speed, an inter-vehicular distance, and an acceleration rate pattern being an output may be created by using machine learning, for example. In this case, a combination of environmental parameters and a vehicle speed is learned from the history as supervised data. Examples of an algorithm to be used include a random forest, a support vector machine, and gradient boosting. The model obtained by learning is used as a driver model.

Further, a method for creating a driver model by collecting drivers similar to a certain driver may be the method described in the fourth exemplary embodiment. However, for example, there is a method for constructing a plurality of driver models in such a way that, if a plurality of local peaks is detected in the distribution of driving characteristic (for example, vehicle speed) data on a cloud, a plurality of clusters is considered to be present based on these local peaks, and a model is created considering that the distribution with each local peak being a peak thereof is regarded as one cluster. According to this method: a driver model most matching the history of the driver on the client side may be selected to estimate a vehicle speed; or a plurality of driver models having a high match rate may be used and a vehicle speed may be obtained by using the average of these driver models.

When the driver sets autonomous driving, autonomous driving controller 281 inputs environmental parameters to the driver model, and performs vehicle control according to the obtained vehicle speed, inter-vehicular distance, and acceleration/deceleration rate pattern. According to this control, there is no need for the driver to set the inter-vehicular distance, for example, during autonomous driving by use of a steering switch or the like, whereby the driver can implement autonomous driving close to his/her driving.

[Summary of Fourth and Fifth Exemplary Embodiments]

Figure 39:
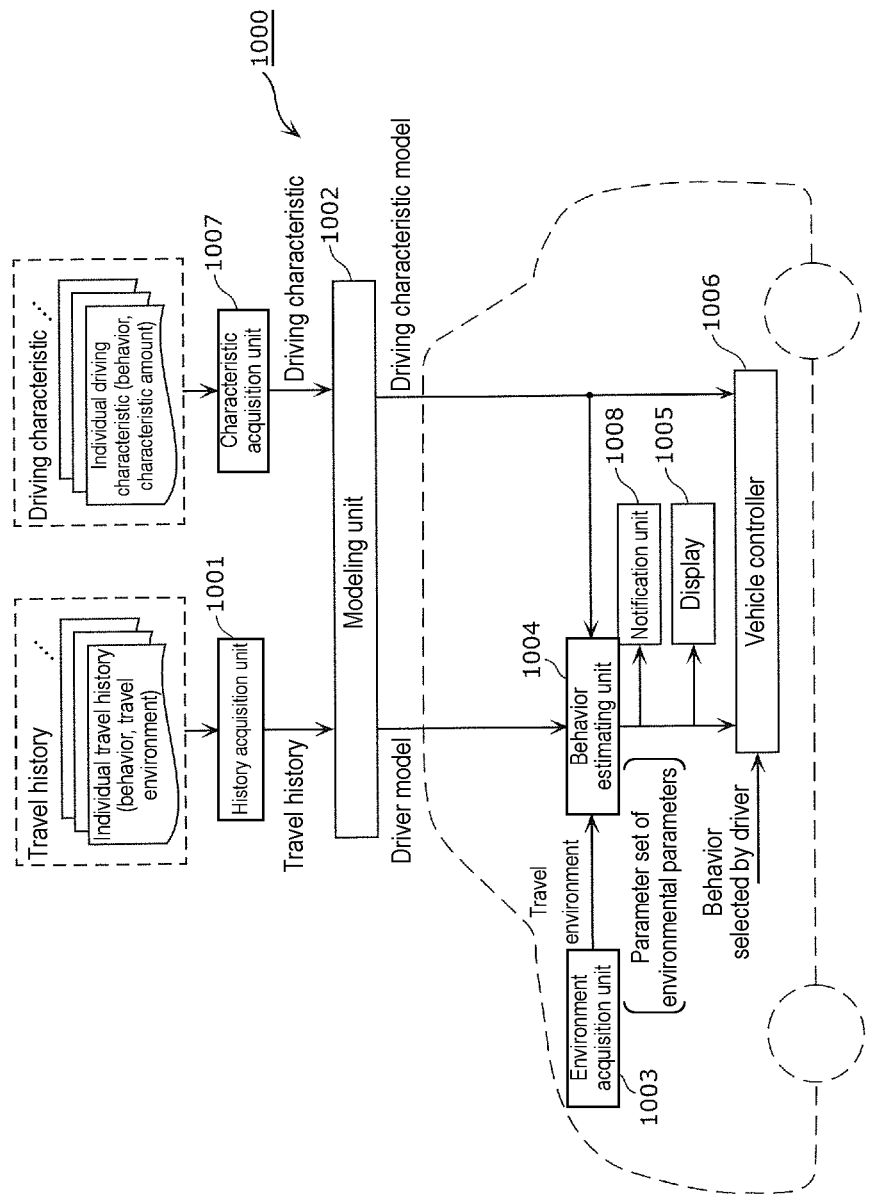
FIG. 39 is a diagram illustrating a configuration of an information processing system according to one exemplary embodiment of the present invention.

FIG. 39 is a diagram illustrating a configuration of an information processing system according to one exemplary embodiment of the present invention.

Information processing system 1000 is provided with history acquisition unit 1001 and modeling unit 1002.

History acquisition unit 1001 acquires an individual travel history of each of a plurality of drivers. The travel history including the individual travel histories is the one illustrated in FIG. 16, 17, or 20, for example, and the individual travel history may be the travel history of driver x illustrated in FIG. 27. The individual travel history indicates, in association with each other, one or a plurality of vehicle behaviors selected by the driver and the travel environment of the vehicle when the one or each of the plurality of behaviors is selected. In the present exemplary embodiment, the behavior indicates a driving action, a driving operation, or an operating state of the vehicle. Further, the one or each of the plurality of vehicle behaviors selected by the driver is the second behavior selected by the driver during autonomous driving in the first exemplary embodiment. Alternatively, the one or each of the plurality of vehicle behaviors selected by the driver may be a behavior executed by the driver during manual driving, that is, a behavior selected during manual driving.

Modeling unit 1002 models the individual travel histories of at least one or more drivers in the travel history, thereby constructing a driver model indicating a relationship between a behavior and a travel environment of the vehicles of the at least one or more drivers. This driver model is the driver model illustrated in FIG. 18, FIG. 21, or part (b) of FIG. 28, for example.

Information processing system 1000 may also be provided with environment acquisition unit 1003 and behavior estimating unit 1004. Environment acquisition unit 1003 acquires a travel environment of a vehicle driven by a driver to be estimated. The travel environment is the one illustrated in FIG. 16, 17, or 20, for example. It is to be noted that environment acquisition unit 1003 may be detector 6 illustrated in FIG. 1. That is, a travel environment may be generated based on the information detected by detector 6, and the generated travel environment may be acquired.

Behavior estimating unit 1004 estimates (or determines) a behavior associated with the travel environment acquired by environment acquisition unit 1003 in the constructed driver model as a behavior of the vehicle driven by the driver to be estimated.

Thus, a behavior of the vehicle driven by the driver to be estimated is estimated by using the driver model, whereby even if the individual travel history of the driver to be estimated is insufficient for behavior estimation, a behavior of the vehicle driven by the driver can appropriately be estimated. That is, a driving action suitable for the driver can be estimated.

Herein, modeling unit 1002 may construct a clustering-type driver model. Specifically, modeling unit 1002 models, for each of groups consisting of a plurality of individual travel histories similar to one another in the travel history, the plurality of individual travel histories similar to one another, to thereby construct a driver model showing a relationship between a behavior and a travel environment of the vehicle for each model driver. Such a clustering-type driver model is the driver model illustrated in FIG. 18, for example.

In this case, behavior estimating unit 1004 selects, from the driver model, a model driver having a relationship of a behavior and a travel environment similar to the individual travel history of the driver to be estimated. Then, behavior estimating unit 1004 estimates, based on the selected model driver's relationship of the behavior and the travel environment, a behavior associated with the travel environment acquired by environment acquisition unit 1003 as a behavior of the vehicle driven by the driver to be estimated.

Thus, the model driver having a relationship of a behavior and a travel environment similar to the individual travel history of the driver to be estimated is selected, and a behavior of the vehicle driven by the driver to be estimated is estimated by using the relationship of the model driver, whereby a behavior (that is, driving action) suitable for the driver can be estimated.

In this case, the individual travel history of each of the plurality of drivers may indicate, for each travel environment, how many times a predetermined one or each of a plurality of behaviors has been selected under the corresponding travel environment.

In this case, for each travel environment, modeling unit 1002 averages, for the predetermined one or each of the plurality of behaviors, frequencies of the behavior indicated in the plurality of individual travel histories similar to one another, thereby modeling the individual travel histories similar to one another.

Thus, the modeling can simply and appropriately be performed.

In addition, modeling unit 1002 may construct an individually-adapted-type driver model. Specifically, modeling unit 1002 constructs a driver model corresponding to the driver to be estimated by modeling a plurality of individual travel histories, in the travel history, similar to the individual travel history of the driver to be estimated. Such an individually-adapted-type driver model is the driver model illustrated in FIG. 21, for example.

According to this, the plurality of individual travel histories similar to the individual travel history of the driver to be estimated in the travel history is modeled, whereby a behavior (that is, driving action) more suitable for the driver can be estimated.

In addition, as illustrated in FIG. 27, the individual travel history of each of the plurality of drivers may indicate a travel environment of the vehicle at the time when one or each of a plurality of behaviors is selected, as a first parameter set which is a parameter set consisting of each numerical value of at least one environmental parameter.

In this case, modeling unit 1002 models the numerical values of the environmental parameters included in the first parameter set indicated by the individual travel histories of at least one or more drivers, thereby constructing a driver model indicating a relationship between a behavior and the first parameter set for the vehicles of the at least one or more drivers. The driver model constructed at this time is the driver model illustrated in part (b) of FIG. 28, for example. Environment acquisition unit 1003 acquires a travel environment of the vehicle driven by the driver to be estimated as a parameter set. Note that this parameter set consists of numerical values of at least one environmental parameter as in the first parameter set. Behavior estimating unit 1004 estimates a behavior associated with the first parameter set similar to the parameter set acquired by environment acquisition unit 1003 in the constructed driver model, as a behavior of the vehicle driven by the driver to be estimated.

Accordingly, because of a travel environment being indicated by using parameters, the travel environment can be categorized in a more detailed manner, and therefore, whatever the travel environment is, a behavior (that is, driving action) according to the travel environment can be estimated.

Information processing system 1000 may also be provided with display 1005 for displaying a behavior candidate. Note that display 1005 may be included in notification unit 92 illustrated in FIG. 1. In addition, the individual travel history of each of the plurality of drivers may further indicate, for each vehicle behavior selected by the driver, a second parameter set as a travel environment at the time when the behavior is displayed as a candidate, in association with the behavior, wherein the second parameter set is a parameter set consisting of each numerical value of at least one environmental parameter. Specifically, the individual travel history indicates, in association with a selected behavior, the first parameter set which shows a travel environment at the time when the behavior is selected, and a second parameter set which shows a travel environment at the time when the behavior is displayed as a candidate. In other words, the second parameter set indicates a travel environment at the time before the first parameter set. Notably, the first parameter set shows a travel environment when the behavior is selected, but also shows a travel environment when the behavior is executed. That is, there is no significant difference between a travel environment at the time when the behavior is selected and a travel environment at the time when the behavior is executed.

In this case, modeling unit 1002 models the numerical values of the environmental parameters included in the first parameter set indicated by the individual travel histories of at least one or more drivers described above, and models the numerical values of the environmental parameters included in the second parameter set, thereby constructing a driver model indicating a relationship between a vehicle behavior and the first or second parameter set for the vehicles of at least one or more drivers described above. Behavior estimating unit 1004 then estimates a behavior associated with the first parameter set or the second parameter set similar to the parameter set acquired by environment acquisition unit 1003 in the constructed driver model as a behavior of the vehicle driven by the driver to be estimated.

The timing at which a behavior candidate is displayed (display timing) is before the timing at which a behavior is selected or executed (selection timing). Also, the travel environment may differ between at the display timing and at the selection timing. At the display timing, a travel environment at that timing can be acquired, but a travel environment at the subsequent selection timing cannot be acquired. Further, it is desirable to estimate a behavior at the display timing.

In view of this, modeling unit 1002 constructs the driver model indicating a relationship among the first parameter set which shows a travel environment at the selection timing, the second parameter set which shows a travel environment at the display timing, and the selected behavior. Further, the parameter set acquired by environment acquisition unit 1003 may be a parameter set at the display timing or a parameter set, at the selection timing, predicted from the parameter set at the display timing through extrapolation. Therefore, when the parameter set acquired by environment acquisition unit 1003 is the parameter set at the display timing, behavior estimating unit 1004 estimates a behavior associated with the second parameter set similar to the parameter set as a behavior of the vehicle driven by the driver to be estimated. Thus, a more suitable behavior (that is, driving action) can be estimated in advance. On the other hand, when the parameter set acquired by environment acquisition unit 1003 is the parameter set at the selection timing, behavior estimating unit 1004 estimates a behavior associated with the first parameter set similar to the parameter set as a behavior of the vehicle driven by the driver to be estimated. Thus, a more suitable behavior (that is, driving action) can be estimated in advance, that is, at the display timing.

In this case, behavior estimating unit 1004 may preferentially estimate a behavior associated with the first parameter set similar to the parameter set acquired by environment acquisition unit 1003 in the constructed driver model as a behavior of the vehicle driven by the driver to be estimated.

Thus, the process for estimating a behavior can be appropriately performed.

The individual travel history may indicate traveling with one or more kinds of vehicle speeds as one or more behaviors as illustrated in FIG. 37. In this case, as illustrated in FIG. 33, environment acquisition unit 1003 acquires a travel environment of the vehicle, which is driven by the driver to be estimated and which is continuously traveling for only a first period with an acceleration rate falling within a predetermined range including zero, as a parameter set. Such a travel state is regarded as a constant-speed travel state. In addition, the first period is T1 second illustrated in FIG. 33, for example. Behavior estimating unit 1004 then estimates traveling at a vehicle speed associated with a first parameter set similar to the parameter set acquired by environment acquisition unit 1003 in the constructed driver model as a behavior of the vehicle driven by the driver to be estimated. Information processing system 1000 is also provided with vehicle controller 1006 that controls the vehicle such that the vehicle travels at the vehicle speed estimated by behavior estimating unit 1004.

Thus, this configuration enables the vehicle to travel at a vehicle speed according to a travel environment and suitable for the driver.

The individual travel history may also indicate traveling with one or more kinds of inter-vehicular distances as one or more behaviors as illustrated in FIG. 37. In this case, as illustrated in FIG. 34, environment acquisition unit 1003 acquires, as a parameter set, a travel environment of the vehicle, which is driven by the driver to be estimated and which is traveling such that a state where an amount of change (inter-vehicular distance change [m/s]) in the distance between the vehicle and another vehicle per unit time falls within a predetermined range including zero continues for a second period. Note that the second period is T2 second illustrated in FIG. 34, for example. Behavior estimating unit 1004 then estimates traveling with an inter-vehicular distance associated with a first parameter set similar to the parameter set acquired by environment acquisition unit 1003 in the constructed driver model as a behavior of the vehicle driven by the driver to be estimated. Vehicle controller 1006 controls the vehicle driven by the driver to be estimated such that the vehicle travels while keeping the inter-vehicular distance estimated by behavior estimating unit 1004.

Thus, this configuration enables the vehicle to travel while keeping an inter-vehicular distance according to a travel environment and suitable for the driver.

The individual travel history may also indicate traveling with one or more kinds of acceleration rate patterns (for example, the acceleration rate patterns illustrated in FIG. 36) as one or more behaviors. In this case, as illustrated in FIG. 35, environment acquisition unit 1003 acquires, as a parameter set, a travel environment of the vehicle at a point corresponding to a period from the time when an absolute value of an acceleration rate of the vehicle driven by the driver to be estimated exceeds a first threshold until the absolute value of the acceleration rate becomes equal to or less than a second threshold lower than the first threshold. For example, the first threshold is acceleration rate threshold A3 in FIG. 35, and the second threshold is acceleration rate threshold A4 in FIG. 35. The point corresponding to the above-mentioned period is the point T3 second before this period in FIG. 35. Behavior estimating unit 1004 then estimates traveling with an acceleration rate pattern associated with a first parameter set similar to the parameter set acquired by environment acquisition unit 1003 in the constructed driver model as a behavior of the vehicle driven by the driver to be estimated. Vehicle controller 1006 controls the vehicle driven by the driver to be estimated such that the vehicle travels with the acceleration rate pattern estimated by behavior estimating unit 1004.

Thus, this configuration enables the vehicle to travel with an acceleration rate pattern according to a travel environment and suitable for the driver. In the example described above, traveling is represented by using an acceleration rate pattern. However, traveling may be represented by using an average acceleration rate.

Figure 40:
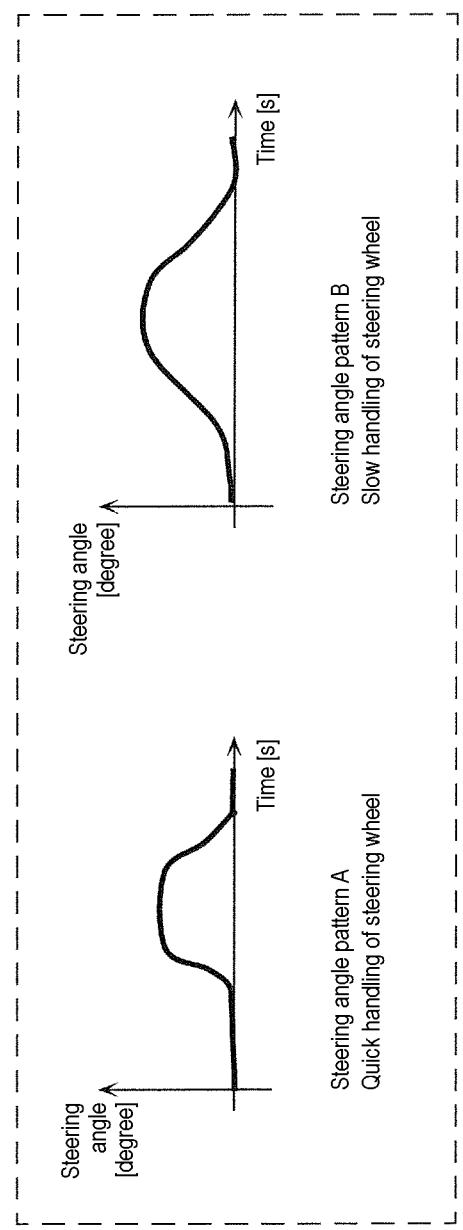
FIG. 40 is a diagram illustrating an example of a steering angle pattern in the information processing system according to one exemplary embodiment of the present invention.
Figure 41:
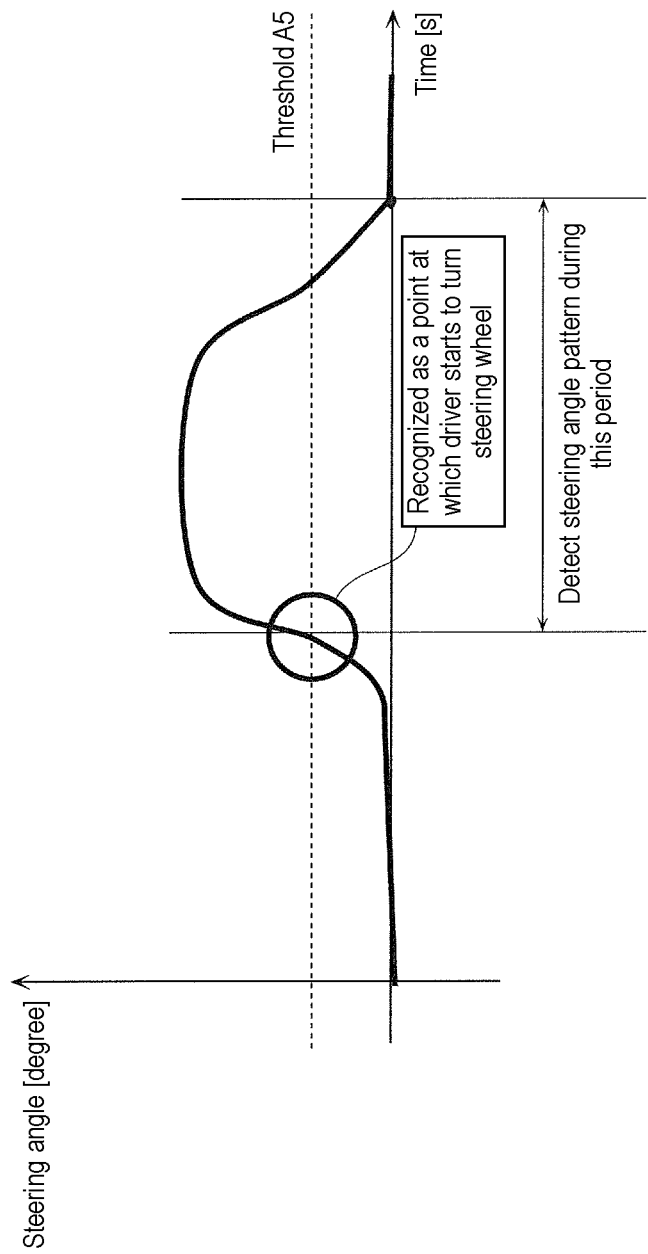
FIG. 41 is a diagram illustrating a timing at which a steering angle and an environmental parameter are collected in the information processing system according to one exemplary embodiment of the present invention.

The individual travel history may also indicate traveling with a steering angle pattern (for example, a steering angle pattern illustrated in FIG. 40) upon a lane change or right/left turn as one or more behaviors. In this case, as illustrated in FIG. 41, environment acquisition unit 1003 acquires, as a parameter set, a travel environment of the vehicle driven by the driver to be estimated at a point corresponding to a period from the time when an absolute value of a steering angle of the vehicle exceeds a first threshold until it becomes zero. For example, the first threshold is steering angle threshold A5 in FIG. 41. Behavior estimating unit 1004 then estimates traveling with a steering angle pattern associated with a first parameter set similar to the parameter set acquired by environment acquisition unit 1003 in the constructed driver model as a behavior of the vehicle driven by the driver to be estimated. Vehicle controller 1006 controls the vehicle driven by the driver to be estimated such that the vehicle travels with the steering angle pattern estimated by behavior estimating unit 1004.

Thus, this configuration enables the vehicle to travel with a steering angle pattern according to a travel environment and suitable for the driver. In the example described above, traveling is represented by using a steering angle pattern. However, traveling may be represented by using a maximum steering angle and a maximum angular velocity of the steering angle.

Information processing system 1000 may also be provided with characteristic acquisition unit 1007. Characteristic acquisition unit 1007 acquires a driving characteristic including an individual driving characteristic of each of a plurality of drivers. As illustrated in FIG. 22, for example, the individual driving characteristic indicates, in association with each other, one or a plurality of behaviors of a vehicle executed by a driving operation performed by the driver and a characteristic amount in the driving operation of the vehicle performed for executing the one or each of the plurality of behaviors. For example, the characteristic amount may be a speed of the vehicle or an operation amount of the steering wheel, brake, and accelerator. In this case, modeling unit 1002 models the individual driving characteristics of at least one or more drivers in the driving characteristic, thereby constructing a driving characteristic model indicating a relationship between a behavior and a travel environment for the vehicles of at least one or more drivers. Note that, similar to the driver model, the driving characteristic model may be of a clustering type or an individually-adapted type. When the one or any of the plurality of behaviors is selected by the driver or behavior estimating unit 1004 as the behavior to be executed, vehicle controller 1006 controls the behavior of the vehicle driven by the driver to be estimated according to the characteristic amount associated with the behavior to be executed in the constructed driving characteristic model. For example, when a behavior of "lane change" is estimated for driver x in a state of having no fellow passenger, vehicle controller 1006 controls the vehicle behavior of "lane change" according to the characteristic amounts such as "8" for the speed, "4" for the steering wheel, "6" for the brake, and "8" for the accelerator, as illustrated in FIG. 22.

Accordingly, a behavior of a vehicle of a driver is performed according to the driving characteristic of the driver, that is, the habit in driving, whereby a driving action more suitable for the driver can be executed.

Notably, a vehicle characteristic model can also be constructed at that time.

Figure 42:
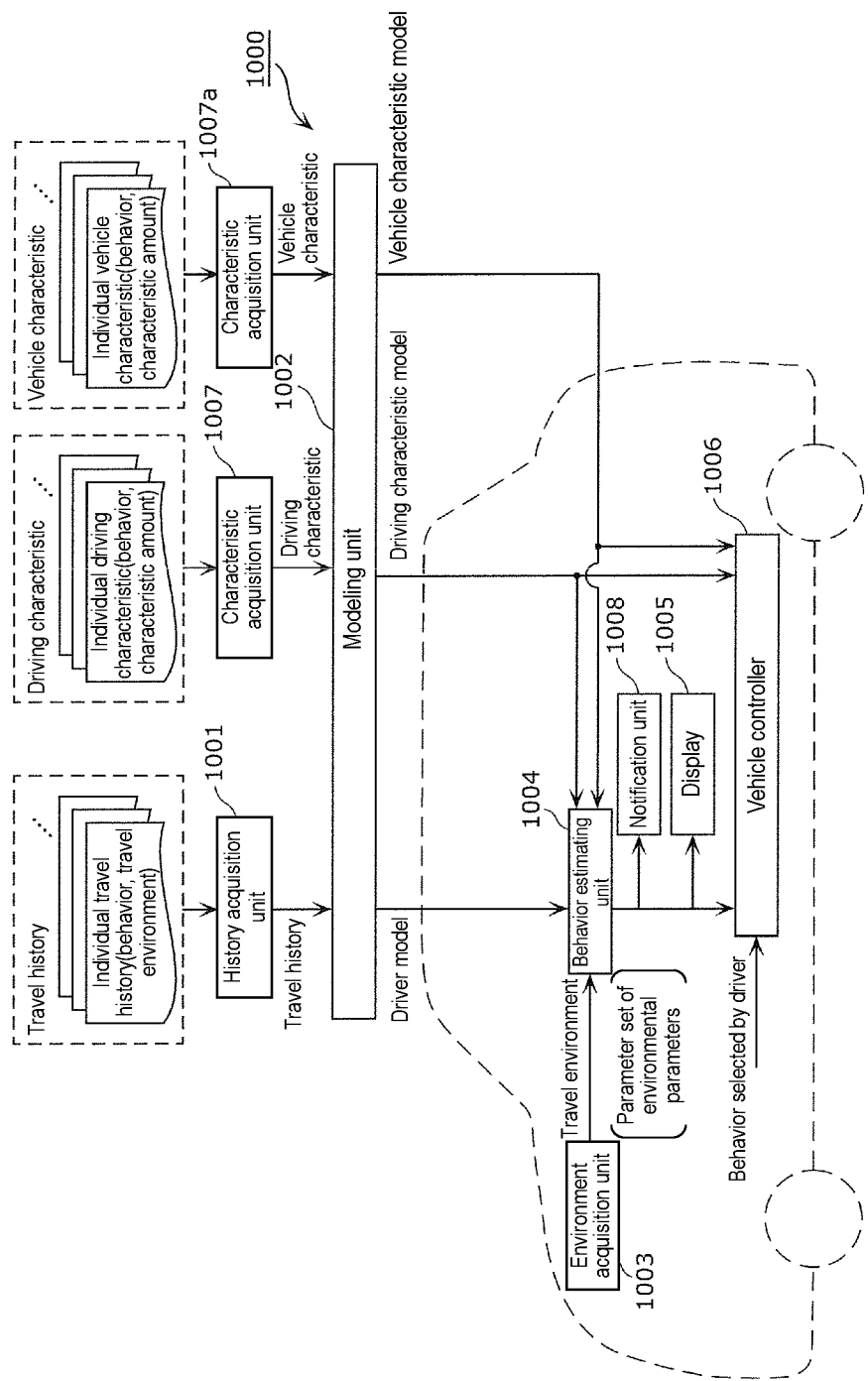
FIG. 42 is a diagram illustrating a configuration of an information processing system for constructing a vehicle characteristic model according to one exemplary embodiment of the present invention.

FIG. 42 is a diagram illustrating a configuration of an information processing system for constructing a vehicle characteristic model. FIG. 43 is a diagram illustrating vehicle characteristics.

Specifically, an effect on the vehicle behavior due to a depressing amount of the brake and accelerator greatly differs for each vehicle. The estimation of such an amount can implement smooth vehicle control. For example, an amount of depression of the brake and a travel environment of the vehicle are acquired as a parameter set together with the acceleration rate when the brake is depressed. The parameter set herein includes a vehicle type ID, vehicle speed, road surface condition (how slippery the road surface is is represented by numerical values in stages), gradient, wind speed (wind speed relative to the advancing direction of the host vehicle), and a total load weight (including occupants). Characteristic acquisition unit 1007a acquires an individual vehicle characteristic of each of a plurality of vehicles. The vehicle characteristic including the individual vehicle characteristics is the one illustrated in FIG. 43, for example. The vehicle characteristic indicates, for each vehicle ID, a situation description parameter (characteristic amount) of the vehicle having the vehicle ID and the amount of depression (behavior) when the vehicle travels with the situation description parameter, in association with each other.

Modeling unit 1002 models the individual vehicle characteristics of at least one or more vehicles in the vehicle characteristic, thereby constructing a vehicle characteristic model indicating a relationship between an amount of depression and a situation description parameter for the at least one or more vehicles. Behavior estimating unit 1004 estimates an amount of depression of the brake as a behavior of the vehicle to be estimated by using the vehicle characteristic model in the manner same as the manner of using the driver model. Specifically, behavior estimating unit 1004 estimates an amount of depression of the brake associated with a first parameter set similar to the parameter set acquired by environment acquisition unit 1003 and the acceleration rate estimated based on the driving characteristic in the constructed vehicle characteristic model as a behavior of the vehicle to be estimated. Vehicle controller 1006 controls the vehicle according to the amount of depression of the brake estimated by behavior estimating unit 1004. The similar control can be applied for the accelerator.

Thus, the vehicle performs a behavior according to the prediction based on the vehicle characteristic, whereby the vehicle control can smoothly be performed.

Information processing system 1000 may also be provided with notification unit 1008 that notifies the driver to be estimated of a behavior estimated by behavior estimating unit 1004 before this behavior is executed. Note that notification unit 1008 may be notification unit 92 in FIG. 1.

According to this configuration, notification regarding the estimated behavior is provided, whereby the driver can easily recognize in advance what behavior is to be executed, and thus, the driver's anxiety can be removed.

It should be noted that all of or some of environment acquisition unit 1003, behavior estimating unit 1004, display 1005, vehicle controller 1006, and notification unit 1008 may be provided to the vehicle driven by the driver to be estimated or provided outside the vehicle. Similarly, all of or some of history acquisition unit 1001, modeling unit 1002, and characteristic acquisition unit 1007 may be provided to the vehicle driven by the driver to be estimated or provided outside the vehicle. When some of the components included in information processing system 1000 are provided to the vehicle and the other components are provided outside of the vehicle, the components outside and inside the vehicle communicate with one another through a network, for example, to execute the respective processes described above.

Further, vehicle controller 1006 may be vehicle controller 7 in FIG. 1. Moreover, history acquisition unit 1001, characteristic acquisition unit 1007, modeling unit 1002, and behavior estimating unit 1004 may be included in vehicle controller 7 illustrated in FIG. 1.

Further, the individual travel history and the individual driving characteristic are generated by vehicle controller 1006 in each vehicle, for example. Vehicle controller 1006 may generate and accumulate the individual travel history or the individual driving characteristic during autonomous driving, or during manual driving.

Figure 44:
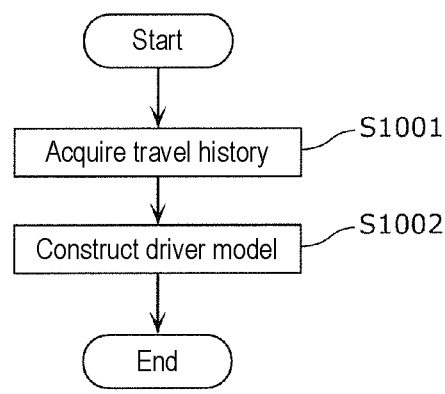
FIG. 44 is a flowchart illustrating an information processing method according to one exemplary embodiment of the present invention.

FIG. 44 is a flowchart illustrating an information processing method according to one exemplary embodiment of the present invention.

The information processing method according to one exemplary embodiment of the present invention includes step S1001 and step S1002.

In step S1001, a travel history is acquired which includes an individual travel history of each of a plurality of drivers, wherein each individual travel history indicates, in association with each other, one or a plurality of vehicle behaviors selected by the driver and a travel environment of the vehicle when the one or each of the plurality of behaviors is selected.

In step S1002, the individual travel histories of at least one or more drivers in the travel history are modeled, whereby a driver model indicating a relationship between a behavior and a travel environment for the vehicles of the at least one or more drivers is constructed.

Thus, a behavior of the vehicle driven by the driver to be estimated is estimated by using the driver model, whereby even if the individual travel history of the driver to be estimated is insufficient for behavior estimation, a behavior of the vehicle driven by the driver can appropriately be estimated. That is, a driving action suitable for the driver can be estimated.

[Modification of Fourth and Fifth Exemplary Embodiments]

In the fourth and fifth exemplary embodiments, a vehicle behavior of a driver (driving action) is estimated, and the vehicle is controlled such that the estimated behavior is executed. On the other hand, the present modification is characterized in that, during manual driving, for example, a dangerous behavior of the vehicle of the driver is estimated, and a warning is issued to the driver so as to inhibit the execution of the dangerous behavior.

Figure 45:
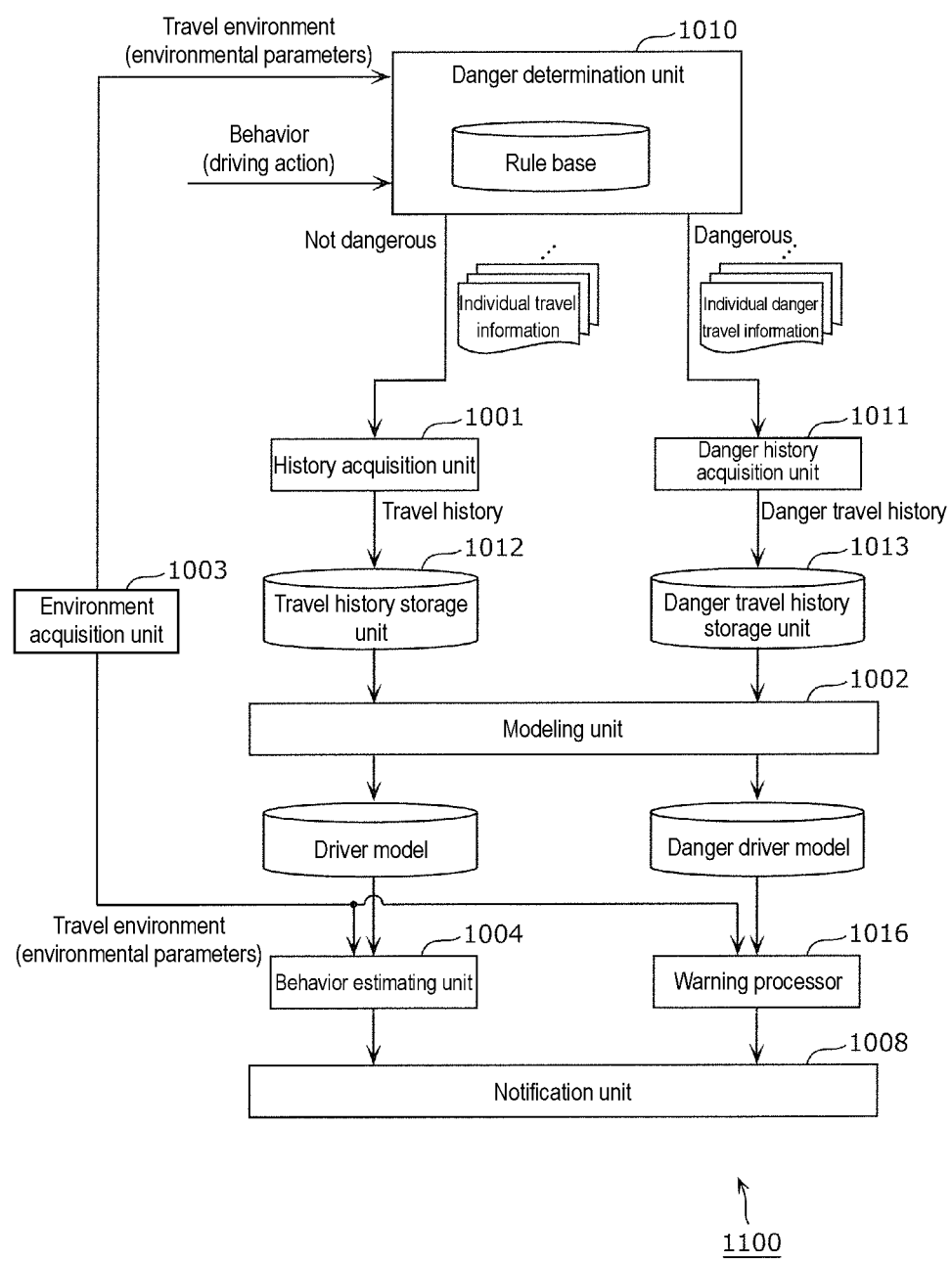
FIG. 45 is a diagram illustrating a configuration of an information processing system according to a modification of one exemplary embodiment of the present invention.

FIG. 45 is a diagram illustrating a configuration of an information processing system according to the present modification.

Similar to information processing system 1000 described above, information processing system 1100 according to the present modification is provided with history acquisition unit 1001, modeling unit 1002, environment acquisition unit 1003, and behavior estimating unit 1004. Information processing system 1100 is also provided with danger determination unit 1010, danger history acquisition unit 1011, travel history storage unit 1012, danger travel history storage unit 1013, and warning processor 1016.

Danger determination unit 1010 acquires a behavior of the vehicle selected by the driver together with a travel environment for the vehicle at the time when the behavior is selected, and determines whether or not the selected behavior is dangerous based on a predetermined determination reference. When being provided to the vehicle, danger determination unit 1010 acquires not only the behavior and the travel environment of the vehicle but also a behavior and a travel environment of another vehicle, and determines whether or not the behavior of the other vehicle is dangerous. Specifically, danger determination unit 1010 acquires, for each of a plurality of drivers, a behavior of the vehicle selected by the driver together with a travel environment for the vehicle at the time when the behavior is selected, and determines whether or not the selected behavior is dangerous based on a predetermined determination reference. Danger determination unit 1010 retains a rule base as the predetermined determination reference. This rule base indicates whether each of a plurality of kinds of behaviors is dangerous or not.

When determining that the behavior is not dangerous, danger determination unit 1010 outputs information including the behavior and the travel environment as individual travel information. On the other hand, when determining that the behavior is dangerous, danger determination unit 1010 outputs information including the behavior and the travel environment as individual danger travel information.

History acquisition unit 1001 acquires, for each of a plurality of drivers, an information group consisting of a plurality of individual travel information items output from danger determination unit 1010 as the individual travel history of the driver. History acquisition unit 1001 then stores a travel history including the individual travel histories of the plurality of drivers into travel history storage unit 1012.

Danger history acquisition unit 1011 acquires, for each of a plurality of drivers, an information group consisting of a plurality of individual danger travel information items output from danger determination unit 1010 as the individual danger travel history of the driver. Danger history acquisition unit 1011 then stores a danger travel history including the individual danger travel histories of the plurality of drivers into danger travel history storage unit 1013.

Modeling unit 1002 constructs not only a driver model using the above-mentioned travel history, but also a danger driver model using the above-mentioned danger travel history. Specifically, modeling unit 1002 models the individual danger travel histories of at least one or more drivers in the danger travel history, thereby constructing a danger driver model indicating a relationship between a dangerous behavior and a travel environment for the at least one or more vehicles. Similar to the driver model, the danger driver model may be of a clustering type or an individually-adapted type.

Warning processor 1016 estimates a dangerous behavior associated with the travel environment acquired by environment acquisition unit 1003 in the constructed driver model as a behavior of the vehicle driven by the driver to be estimated. Then, warning processor 1016 executes a process for issuing a warning regarding the estimated dangerous behavior to the driver. Notification unit 1008 issues a warning to the driver according to the process of warning processor 1016.

FIG. 46 is a diagram illustrating one example of a danger travel history stored in danger travel history storage unit 1013.

For example, the danger travel history indicates, for each driver ID for identifying a driver, the driver ID, a travel environment of the vehicle driven by the driver indicated by the driver ID, and a dangerous behavior (that is, risk) selected under the travel environment. In addition, the travel environment includes environmental parameters such as a vehicle speed (km/h), an inter-vehicular distance (m) with a leading vehicle, a relative change rate of a leading vehicle, an inter-vehicular distance (m) with a leading vehicle on the left side, and a relative change rate of a leading vehicle on the left side, for example. The relative change rate of a leading vehicle is a rate of change of the head-to-head spacing between the head of the host vehicle and the head of the leading vehicle, and the relative change rate of a leading vehicle on the left side is a rate of change of the head-to-head spacing between the head of the host vehicle and the head of the leading vehicle on the left side. Further, the risk includes rear-end collision, lane departure, and minor collision with a following vehicle on the right side, for example.

When a driver having an individual danger travel history similar to the driver to be estimated has previously performed dangerous driving, and the travel environment during the dangerous driving is acquired in the vehicle driven by the driver to be estimated, information processing system 1100 described above issues a warning according to the content of the risk.

For example, when a travel environment having a high possibility of colliding with a leading vehicle is acquired by environment acquisition unit 1003, warning processor 1016 estimates rear-end collision as a dangerous behavior. Specifically, this travel environment indicates a distance between the vehicles and a timing of depressing a brake. If the driver having an individual danger travel history similar to that of the driver to be estimated has previously had rear-end collision under the travel environment, warning processor 1016 determines that a possibility of rear-end collision is high under the travel environment. Warning processor 1016 then displays a warning message for encouraging the driver to depress the brake earlier on notification unit 1008 provided as an HUD, for example.

When a travel environment having a high possibility of lane departure is acquired by environment acquisition unit 1003, warning processor 1016 estimates lane departure as a dangerous behavior. Specifically, this travel environment indicates a vehicle speed, an operation amount (steering angle) of a steering wheel upon braking, a lane width, and a curvature radius of a curve of the road on which the vehicle is traveling. If the driver having an individual danger travel history similar to that of the driver to be estimated has previously experienced lane departure under the travel environment due to a failure to negotiate a curve, for example, warning processor 1016 determines that a possibility of lane departure is high under the travel environment. Warning processor 1016 then displays a warning message for encouraging the driver to reduce the speed of the vehicle on notification unit 1008 provided as an HUD, for example. In this case, warning processor 1016 may display a desired operation amount (steering angle) of the steering wheel or a travel line on notification unit 1008.

When a travel environment having a high possibility of minor collision with another vehicle due to a lane change is acquired by environment acquisition unit 1003, warning processor 1016 estimates minor collision as a dangerous behavior. Specifically, this travel environment indicates a distance between the host vehicle and a following vehicle on the right side, for example. If the driver having an individual danger travel history similar to that of the driver to be estimated has previously had minor collision with a following vehicle on the right side under the travel environment, warning processor 1016 determines that a possibility of minor collision with a following vehicle on the right side is high under the travel environment. Warning processor 1016 then displays a warning message for notifying the driver of an approach of the following vehicle on the right side on notification unit 1008 provided as an HUD, for example.

When a travel environment having a high possibility of minor collision with an obstacle such as a pedestrian is acquired by environment acquisition unit 1003, warning processor 1016 estimates minor collision as a dangerous behavior. Specifically, this travel environment indicates a distance between the host vehicle and an obstacle, for example. If the driver having an individual danger travel history similar to that of the driver to be estimated has previously had minor collision with an obstacle (or has urgently avoided minor collision) under the travel environment, warning processor 1016 determines that a possibility of minor collision with an obstacle is high under the travel environment. Warning processor 1016 then displays a warning message for calling attention to an obstacle on notification unit 1008 provided as an HUD, for example.

When a travel environment having a high possibility of an accident while turning right or left is acquired by environment acquisition unit 1003, warning processor 1016 estimates an accident while turning as a dangerous behavior. Specifically, this travel environment indicates a spot where the vehicle is traveling (specifically, an intersection), and a distance between the host vehicle and an obstacle, for example. If the driver having an individual danger travel history similar to that of the driver to be estimated has previously had an accident while turning under the travel environment, warning processor 1016 determines that a possibility of an accident while turning is high under the travel environment. Warning processor 1016 then displays a warning message for avoiding an accident while turning on notification unit 1008 provided as an HUD, for example.

As described above, according to the present modification, when the driver to be estimated performs manual driving, for example, a warning for avoiding a dangerous behavior such as rear-end collision or lane departure can be issued to the driver, whereby the occurrence of the dangerous behavior can be suppressed.

(Sixth Exemplary Embodiment)

In the fourth or fifth exemplary embodiment, a driver model indicating a relationship between a travel environment and a vehicle behavior is constructed. On the other hand, in the present exemplary embodiment, a driver model indicating a relationship between a travel environment and a driver's condition (hereinafter referred to as a driver condition) is constructed. Such a driver model is used for estimating a driver condition of the driver to be estimated, for example.

Figure 47:
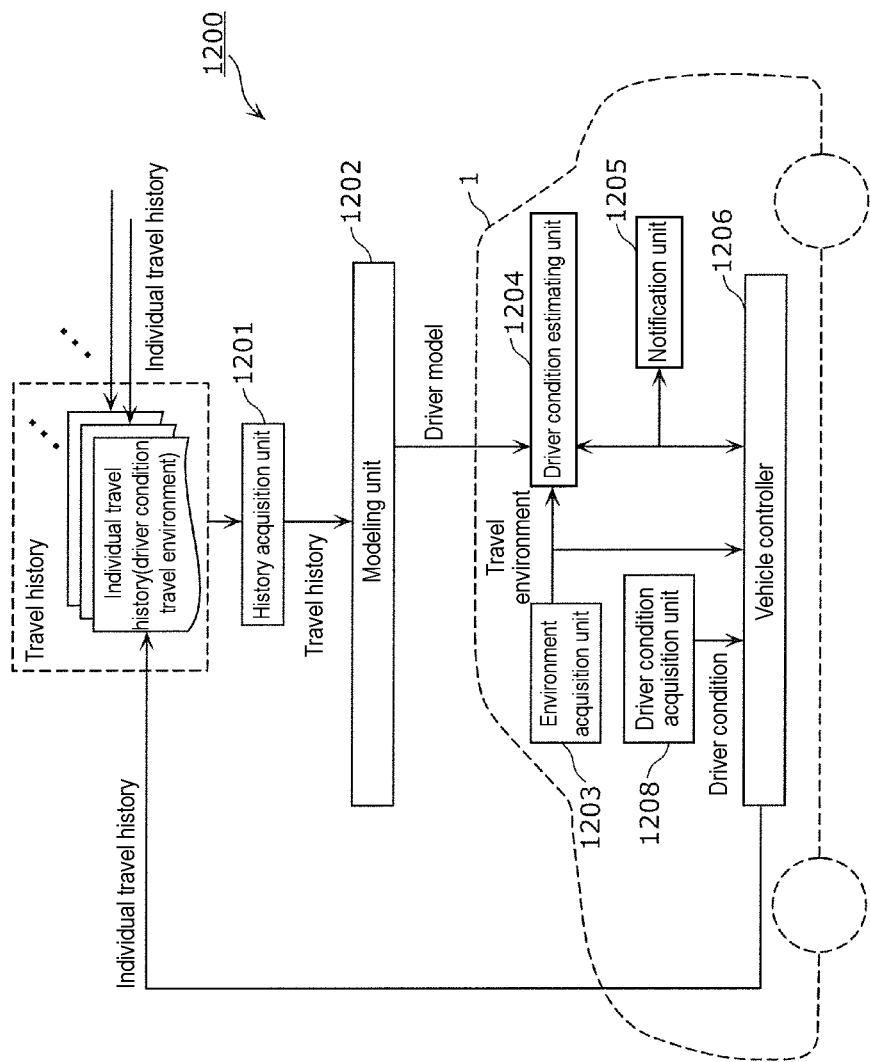
FIG. 47 is a block diagram illustrating a configuration of an information processing system according to the sixth exemplary embodiment.

FIG. 47 is a block diagram illustrating a configuration of an information processing system according to the sixth exemplary embodiment of the present invention.

Information processing system 1200 is provided with history acquisition unit 1201 and modeling unit 1202. These components are disposed in a server, for example.

History acquisition unit 1201 acquires individual travel histories of each of a plurality of drivers including an individual travel history of a driver to be estimated who is driving vehicle 1. The individual travel history indicates, for each travel environment for a vehicle of each driver, the travel environment and a driver condition at the time after a lapse of a predetermined time from the point at which the vehicle encounters the travel environment, in association with each other. History acquisition unit 1201 then outputs a travel history including the acquired individual travel histories of each of the plurality of drivers to modeling unit 1202.

Modeling unit 1202 acquires the travel history from history acquisition unit 1201, and models the individual travel histories of at least one or more drivers from among the individual travel histories of the plurality of drivers based on a degree of similarity among the individual travel histories of the plurality of drivers included in the travel history. A driver model is constructed by such a modeling process. Specifically, modeling unit 1202 performs the modeling process described above to construct a driver model indicating a relationship between driver conditions of at least one or more drivers and the travel environments of at least one or more vehicles. Note that at least one or more drivers may be only one driver. Further, if the individual travel histories of M (M is an integer of two or more) drivers are acquired by history acquisition unit 1201, at least one or more drivers are M drivers or less.

The driver model constructed by modeling unit 1202 may be a clustering-type driver model or an individually-adapted type driver model described in the fourth or fifth exemplary embodiment. Specifically, the driver model is a model constructed from an individual travel history of at least one driver which is similar to the individual travel history of the driver to be estimated.

Specifically, when an individually-adapted type driver model is constructed, modeling unit 1202 performs modeling by extracting an individual travel history of at least one driver having a high degree of similarity (that is, correlation) to the individual travel history of the driver to be estimated. In the case where the individual travel history is a vector (N-dimensional vector) consisting of N numerical values, an individual travel history of at least one driver having a vector which correlates highly with the vector of the individual travel history of the driver to be estimated is extracted. Then, a driver model indicating an average of the vectors of the extracted individual travel history of at least one driver is constructed.

Also, when a clustering-type driver model is constructed, modeling unit 1202 models the individual travel histories of at least one or more drivers described above by clustering such as k-means clustering. If the individual travel history is a vector (N-dimensional vector) consisting of N numerical values, points indicated by each individual travel history in N dimensions are clustered. As a result of clustering, a driver model indicating a centroid position of the individual travel histories of at least one or more drivers is constructed.

Information processing system 1200 is further provided with environment acquisition unit 1203, driver condition estimating unit 1204, vehicle controller 1206, driver condition acquisition unit 1208, and notification unit 1205. These components are disposed in vehicle 1, for example.

Environment acquisition unit 1203 acquires a travel environment of vehicle 1 driven by the driver to be estimated. The travel environment may be the travel environment of "approach to a merging lane" or the travel environment where "there is a low-speed vehicle ahead" as illustrated in FIGS. 16 to 21, or may be a travel environment indicated by at least one environmental parameter as illustrated in FIGS. 27 and 28.

Driver condition acquisition unit 1208 is a driver monitor, installed into vehicle 1, for acquiring a driver condition of the driver to be estimated. Specifically, driver condition acquisition unit 1208 is provided with a camera that captures the driver. Driver condition acquisition unit 1208 may also be provided with a pressure sensor or an infrared sensor, mounted to a driver's seat, for detecting a posture or a heart rate of the driver, or may be provided with other sensors.

The driver condition may be a condition of the driver obtained from an image captured by the camera, a parameter detected by the sensors described above, or a condition of the driver derived from the parameter. Specifically, the driver condition includes visual distraction, gaze to equipment in the vehicle such as a speedometer, drowsiness, biological information, and posture of a driver, for example. If driver condition acquisition unit 1208 has a face authentication function, the driver condition may include identification information for identifying a driver.

Specifically, driver condition acquisition unit 1208 detects a gaze direction of the driver by analyzing an image captured by the camera. Driver condition acquisition unit 1208 then acquires, as a driver condition, a number of times or a time in which the gaze is turned toward equipment in the vehicle, or a number of times or a time (that is, the number of times of visual distraction or visual distraction time) in which the gaze is turned to a direction different from the advancing direction of vehicle 1. Driver condition acquisition unit 1208 also acquires, as a driver condition, a perception delay time from the time when a dangerous object ahead of vehicle 1 is detected by, for example, sensor 62 provided as an advanced driver assistance system (ADAS) until the driver turns his/her gaze to the dangerous object ahead of vehicle 1. Driver condition acquisition unit 1208 also acquires, as a driver condition, a number of times, a time, or an intensity level of drowsiness or doze of the driver by analyzing the captured image. Driver condition acquisition unit 1208 also acquires, as a driver condition, biological information and a posture of the driver through an analysis of the captured image or an output signal from the pressure sensor, for example. The biological information is information indicating a heart rate or a stress intensity level of the driver, or a level of emotion such as comfort or discomfort. The posture indicates a number of times of an unsafe posture of the driver, such as a posture while the driver searches a baggage on a passenger seat, or a number of times or an intensity level of loss of consciousness.

Driver condition estimating unit 1204 acquires the driver model constructed by modeling unit 1202. Driver condition estimating unit 1204 estimates a driver condition associated with a travel environment most similar to the current travel environment acquired by environment acquisition unit 1203 in the constructed driver model as a driver condition of the driver to be estimated.

Vehicle controller 1206 generates, for each travel environment acquired by environment acquisition unit 1203, an individual travel history indicating, in association with each other, the travel environment and a driver condition acquired by driver condition acquisition unit 1208 after a lapse of a predetermined time from the acquisition of the travel environment. Vehicle controller 1206 then transmits the individual travel history to a server, for example. History acquisition unit 1201 described above acquires the individual travel history transmitted from vehicle controller 1206 as one individual travel history included in the travel history.

When the driver condition is estimated by driver condition estimating unit 1204, vehicle controller 1206 determines whether or not the estimated driver condition is dangerous. When determining that the estimated driver condition is dangerous, vehicle controller 1206 executes a danger avoidance process. The danger avoidance process is, for example, a warning process for causing notification unit 1205 to issue a warning to the user. Alternatively, the danger avoidance process is a route guidance process for causing notification unit 1205 to provide the guidance of a route where the driver condition determined to be dangerous does not occur, for example. Notification unit 1205 that provides such route guidance is implemented by a car navigation system, for example. In other words, the car navigation system has a function of notification unit 1205.

Figure 48:
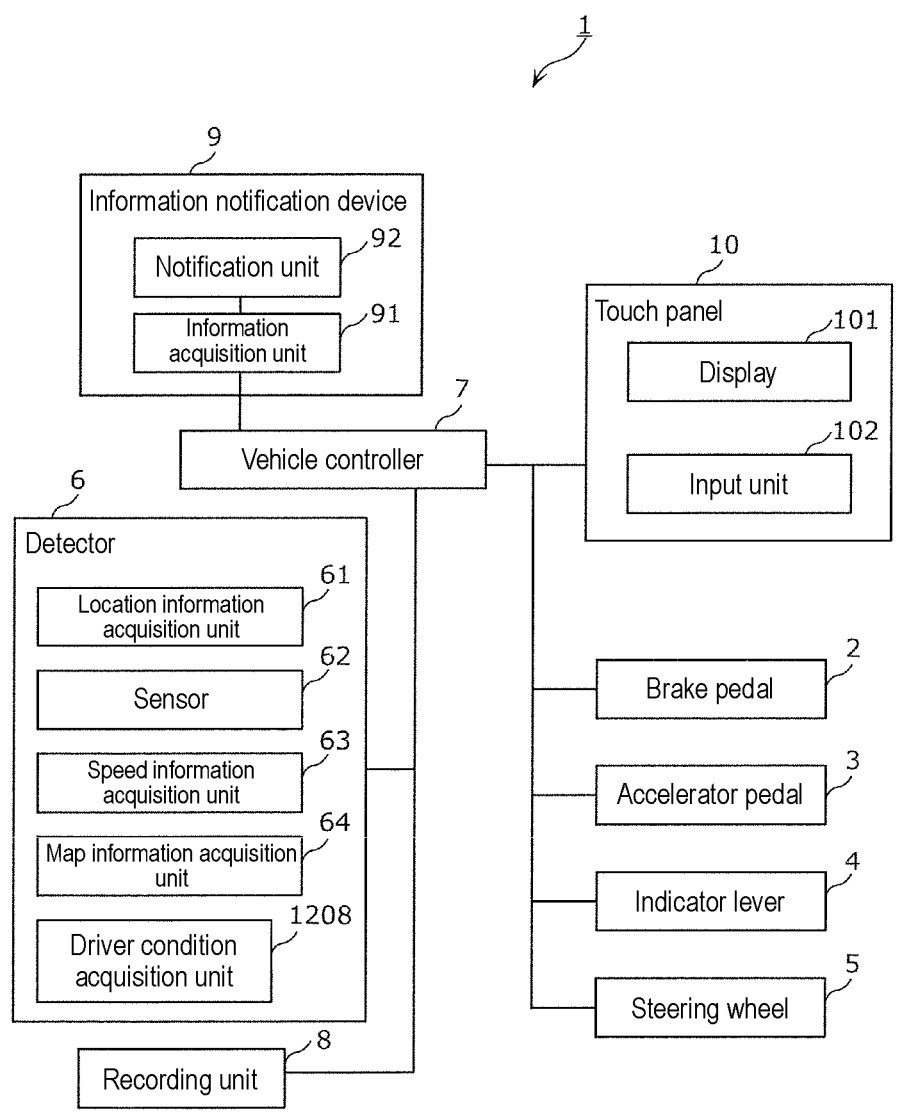
FIG. 48 is a block diagram illustrating a configuration of a main part of a vehicle according to the sixth exemplary embodiment.

FIG. 48 is a block diagram illustrating a configuration of a main part of vehicle 1 according to the sixth exemplary embodiment. It should be noted that constituent elements in FIG. 47 which are substantially identical to the constituent elements in FIG. 1 or 13 are denoted by the identical reference numerals used in FIG. 1 or 13 and will not be described in detail.

Detector 6 in the present exemplary embodiment is provided with location information acquisition unit 61, sensor 62, speed information acquisition unit 63, and map information acquisition unit 64, and further provided with driver condition acquisition unit 1208 described above. That is, a unit including location information acquisition unit 61, sensor 62, speed information acquisition unit 63, and map information acquisition unit 64 corresponds to environment acquisition unit 1203 in FIG. 47. In addition, notification unit 92 included in information notification device 9 corresponds to notification unit 1205 in FIG. 47, and vehicle controller 7 includes vehicle controller 1206 and driver condition estimating unit 1204 in FIG. 47.

FIG. 49 is a diagram illustrating one example of a travel history according to the sixth exemplary embodiment.

The travel history illustrated in FIG. 49 has a configuration similar to the travel history in FIGS. 16 and 17, and indicates a frequency of an occurrence of a dangerous driver condition instead of the frequency of selection of a predetermined behavior. The travel history also includes identification information (that is, driver ID) of the driver recognized by driver condition acquisition unit 1208. Specifically, this travel environment indicates that, under the travel environment of "approach to a merging lane" or the travel environment of "lane change", the driver with driver ID "01" has turned his/her gaze toward the speedometer five times, has had a high stress ten times, and has taken an unsafe posture twice. Note that the high stress means a stress in an intensity level equal to or higher than a threshold. This travel environment also indicates that, under the travel environment of "urban area" or "traffic jam", the driver with driver ID "01" has been visually distracted seven times, has dozed off three times, and has had loss of consciousness once. This travel environment also indicates that, under the travel environment where "there is a dangerous object ahead", the driver with driver ID "01" has had a delay (perception delay) before he/she turns his/her gaze toward the dangerous object four times, and has had a high heart rate seven times. Note that the high heart rate means a heart rate equal to or higher than a threshold.

Modeling unit 1202 constructs, for each of a plurality of travel environments, a driver model indicating a frequency of at least one dangerous driver condition based on the travel history illustrated in FIG. 49.

Driver condition estimating unit 1204 estimates a driver condition having a frequency equal to or larger than the threshold from among at least one driver condition associated with the travel environment acquired by environment acquisition unit 1203 in the driver model as a driver condition of the driver to be estimated. Alternatively, driver condition estimating unit 1204 may estimate the driver condition having the highest frequency from among at least one driver condition associated with the acquired travel environment as a driver condition of the driver to be estimated. In this case, when the driver condition is estimated by driver condition estimating unit 1204, vehicle controller 1206 determines that the estimated driver condition is dangerous.

The travel history illustrated in FIG. 49 indicates the frequency of occurrence of a dangerous driver condition. However, the travel history may indicate the driver condition by using parameters.

FIG. 50 is a diagram illustrating another example of a travel history according to the sixth exemplary embodiment.

The travel history in FIG. 50 indicates a travel environment by using a plurality of environmental parameters as in the travel histories in FIGS. 27 and 28, and indicates a driver condition by using a plurality of condition parameters.

For example, as illustrated in FIG. 50, the travel history indicates an inter-vehicular distance, vehicle speed, degree of lane departure, spot, time, temperature, and the like by environmental parameters. The travel history also indicates visual distraction, drowsiness, stress, heart rate, discomfort level, unsafe posture, and loss of consciousness by condition parameters. The condition parameters excluding the heart rate may be an intensity level or a number of times.

Specifically, the travel history in FIG. 50 indicates that, as the environmental parameters showing the travel environment that the vehicle driven by the driver with driver ID "01" encounters, the inter-vehicular distance is "3", the speed is "5", the degree of lane departure is "0", the spot is "4", the time is "6", and the ambient temperature is "2". It is to be noted that these numerical values may be those obtained by location information acquisition unit 61, sensor 62, speed information acquisition unit 63, or map information acquisition unit 64, or normalized values.

The travel history in FIG. 50 indicates that, as condition parameters associated with the above-mentioned travel environment, the visual distraction is "1", the drowsiness is "5", the stress is "2", the heart rate is "5", the discomfort level is "6", the unsafe posture is "1", and loss of consciousness is "0". It is to be noted that these numerical values may be those obtained by driver condition acquisition unit 1208, or normalized values.

Modeling unit 1202 constructs, for each of a plurality of travel environments, a driver model indicating at least one condition parameter based on the travel history illustrated in FIG. 50. Notably, each of the plurality of travel environments is a set of environmental parameters such as an inter-vehicular distance, speed, and degree of lane departure.

Driver condition estimating unit 1204 estimates at least one condition parameter associated with a travel environment most similar to the travel environment acquired by environment acquisition unit 1203 in the driver model as a driver condition of the driver to be estimated.

When the driver condition is estimated by driver condition estimating unit 1204, vehicle controller 1206 determines whether or not each numerical value of at least one condition parameter which indicates the driver condition is larger than the threshold. When determining that any of the numerical values of the condition parameter is larger than the threshold, vehicle controller 1206 determines that the driver condition of the type corresponding to the condition parameter is dangerous. For example, vehicle controller 1206 compares "5" of the drowsiness which is the estimated condition parameter to the threshold "3". The value "5" of the drowsiness is larger than the threshold "3", and thus, vehicle controller 1206 determines that the driver condition of the type corresponding to the condition parameter, that is, drowsiness, is dangerous.

Figure 51:
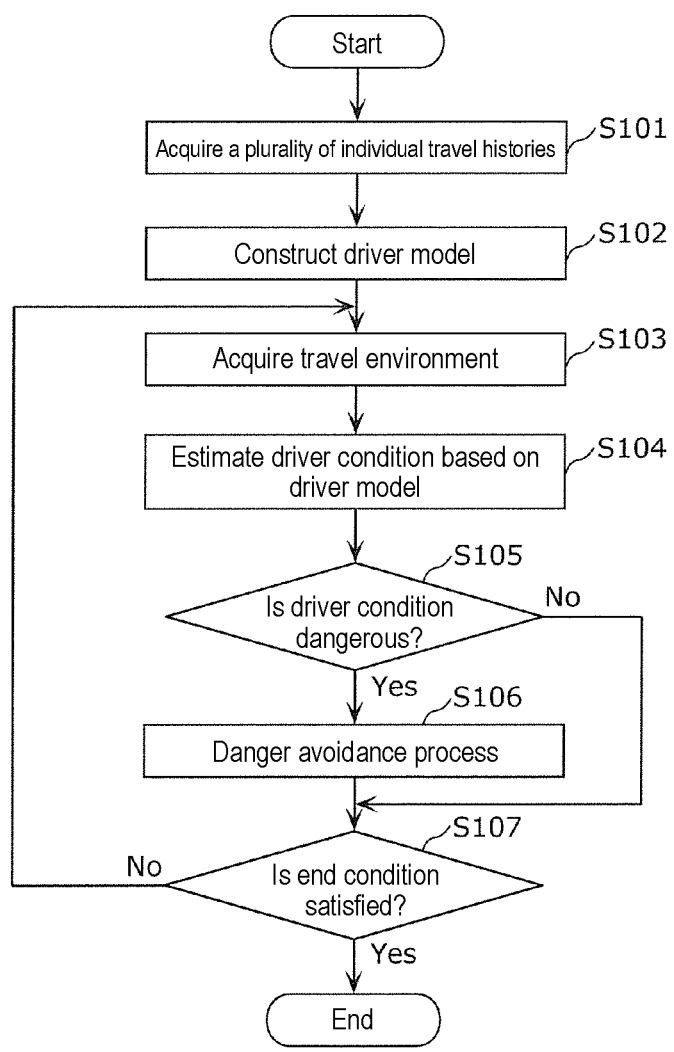
FIG. 51 is a flowchart illustrating a processing operation of the information processing system according to the sixth exemplary embodiment.

FIG. 51 is a flowchart illustrating a processing operation of information processing system 1200 according to the sixth exemplary embodiment.

Firstly, history acquisition unit 1201 acquires a plurality of individual travel histories (step S101). Then, modeling unit 1202 constructs a driver model of the driver to be estimated based on a travel history including the plurality of individual travel histories acquired by history acquisition unit 1201 (step S102).

Environment acquisition unit 1203 acquires a travel environment of vehicle 1 driven by the driver to be estimated (step S103). Driver condition estimating unit 1204 estimates, as a driver condition of the driver to be estimated, a driver condition associated with a travel environment most similar to the acquired travel environment in the driver model constructed through modeling by modeling unit 1202 (step S104).

Vehicle controller 1206 determines whether or not the driver condition estimated in step S104 is dangerous (step S105). When determining that the driver condition is dangerous in step S105 (Yes in step S105), vehicle controller 1206 executes the danger avoidance process (step S106).

After executing the danger avoidance process or when determining that the driver condition is not dangerous in step S105 (No in step S105), vehicle controller 1206 determines whether or not an end condition of the process for estimating the driver condition is satisfied (step S107). When the end condition is determined to be satisfied (Yes in step S107), information processing system 1200 ends the process for estimating the driver condition. On the other hand, when the end condition is determined not to be satisfied (No in step S107), environment acquisition unit 1203, driver condition estimating unit 1204, and vehicle controller 1206 repeatedly execute the process from step S103.

In more details, vehicle controller 1206 executes the following processes as the danger avoidance process.

[Visual Distraction]

For example, in the driver model constructed based on the travel environment illustrated in FIG. 49 or 50, a travel environment (that is, a surrounding environment) is associated with a frequency or a condition parameter of visual distraction which is the driver condition. Therefore, driver condition estimating unit 1204 may estimate the visual distraction or the condition parameter of the visual distraction as a driver condition of the driver to be estimated.

When the visual distraction is estimated as a driver condition, vehicle controller 1206 determines that the visual distraction is dangerous. Alternatively, when the condition parameter of the visual distraction is estimated as a driver condition, vehicle controller 1206 determines whether or not the visual distraction is dangerous based on the numerical value of the condition parameter. When determining that the visual distraction is dangerous, vehicle controller 1206 executes the above-mentioned warning process as the danger avoidance process. That is, vehicle controller 1206 causes notification unit 1205 to issue a warning sound or to display a warning image.

Thus, in an urban area where the driver to be estimated is likely to be visually distracted, a warning sound or the like can be output before the driver to be estimated is visually distracted, whereby the visual distraction of the driver to be estimated can be prevented in advance.

[Gaze]

For example, in the driver model constructed based on the travel environment illustrated in FIG. 49, a travel environment is associated with a frequency of a gaze to a speedometer which is the driver condition. Therefore, driver condition estimating unit 1204 may estimate the gaze to the speedometer as a driver condition of the driver to be estimated.

When the gaze to the speedometer is estimated as a driver condition, vehicle controller 1206 determines that the gaze to the speedometer is dangerous. In this case, vehicle controller 1206 executes the above-mentioned warning process as the danger avoidance process. That is, vehicle controller 1206 causes notification unit 1205 to issue a warning sound or to display a warning image. Alternatively, vehicle controller 1206 may execute a process for displaying a running speed on a head-up display mounted to vehicle 1 as the danger avoidance process.

Thus, under a travel environment where the driver is likely to turn his/her gaze toward the speedometer, a running speed is displayed on the head-up display before the driver to be estimated turns his/her gaze toward the speedometer, whereby inattention of the driver to be estimated to a forward environment can be suppressed in advance.

In addition, in the driver model constructed based on the travel environment illustrated in FIG. 49, a travel environment (specifically, a travel environment where "there is a dangerous object ahead") is associated with a frequency of perception delay which is the driver condition. Therefore, driver condition estimating unit 1204 may estimate the perception delay as a driver condition of the driver to be estimated.

When the perception delay is estimated as a driver condition, vehicle controller 1206 determines that the perception delay which is the driver condition is dangerous. In this case, vehicle controller 1206 executes the above-mentioned warning process as the danger avoidance process. That is, vehicle controller 1206 causes notification unit 1205 to issue a warning sound or to display a warning image.

Thus, before the driver to be estimated perceives the dangerous object ahead, a warning sound or the like can be output, whereby the driver to be estimated can perceive the dangerous object earlier.

[Drowsiness]

For example, in the driver model constructed based on the travel environment illustrated in FIG. 49 or 50, a travel environment is associated with a frequency of dozing off or a condition parameter of drowsiness which is the driver condition. Therefore, driver condition estimating unit 1204 may estimate the condition parameter of doze or drowsiness as a driver condition of the driver to be estimated.

When doze is estimated as a driver condition, vehicle controller 1206 determines that the doze is dangerous. When the condition parameter of drowsiness is estimated as a driver condition, vehicle controller 1206 determines whether or not the drowsiness is dangerous based on the numerical value of the condition parameter. When determining that the drowsiness is dangerous, vehicle controller 1206 executes the above-mentioned warning process as the danger avoidance process. That is, vehicle controller 1206 causes notification unit 1205 to issue a warning sound or to display a warning image. Alternatively, vehicle controller 1206 may execute, as the danger avoidance process, a process for causing notification unit 1205 configured as car audio equipment to play high tempo music.

Thus, while in a traffic jam where the driver to be estimated is likely to doze off, a warning sound, high tempo music, or the like can be output before the driver to be estimated begins to doze off, whereby the driver to be estimated can be prevented from dozing off in advance. That is, the driver to be estimated can be awakened.

[Heart Rate or Stress]

For example, in the driver model constructed based on the travel environment illustrated in FIG. 49 or 50, a travel environment is associated with a frequency of a high heart rate or a condition parameter of a heart rate which is the driver condition. Therefore, driver condition estimating unit 1204 may estimate a high heart rate or the condition parameter of a heart rate as a driver condition of the driver to be estimated.

When a high heart rate is estimated as a driver condition, vehicle controller 1206 determines that the high heart rate is dangerous. When the condition parameter of a heart rate is estimated as a driver condition, vehicle controller 1206 determines whether or not the heart rate is dangerous based on the numerical value of the condition parameter. When determining that the heart rate is dangerous, vehicle controller 1206 executes the above-mentioned route guidance process as the danger avoidance process. Specifically, when a destination and a route to the destination are set and displayed by a car navigation system, vehicle controller 1206 causes notification unit 1205 to provide the guidance of another route (that is, detour route) in place of the current route.

Similarly, in the driver model constructed based on the travel environment illustrated in FIG. 49 or 50, a travel environment is associated with a frequency of a high stress or a condition parameter of a stress which is the driver condition. Therefore, driver condition estimating unit 1204 may estimate a high stress or the condition parameter of a stress as a driver condition of the driver to be estimated.

When a high stress is estimated as a driver condition, vehicle controller 1206 determines that the high stress is dangerous. When the condition parameter of a stress is estimated as a driver condition, vehicle controller 1206 determines whether or not the stress is dangerous based on the numerical value of the condition parameter. When determining that the stress is dangerous, vehicle controller 1206 executes the above-mentioned route guidance process as the danger avoidance process in the same manner as described above.

Thus, before the heart rate or stress is increased due to traveling in an urban area, another route for making a detour around the urban area is displayed, which can prevent the driver to be estimated from being in a dangerous condition.

[Emotion (Comfort or Discomfort)]

For example, in the driver model constructed based on the travel environment illustrated in FIG. 49 or 50, a travel environment is associated with a discomfort frequency or a condition parameter of discomfort level which is the driver condition. Therefore, driver condition estimating unit 1204 may estimate discomfort or the condition parameter of discomfort level as a driver condition of the driver to be estimated.

When the discomfort is estimated as a driver condition, vehicle controller 1206 determines that the discomfort is dangerous. When the condition parameter of discomfort level is estimated as a driver condition, vehicle controller 1206 determines whether or not the discomfort level is dangerous based on the numerical value of the condition parameter. When determining that the discomfort level is dangerous, vehicle controller 1206 executes the above-mentioned route guidance process as the danger avoidance process.

Thus, before the driver feels discomfort due to traveling in an urban area, another route for making a detour around the urban area is displayed, which can prevent the driver to be estimated from feeling discomfort.

[Unsafe Posture]

For example, in the driver model constructed based on the travel environment illustrated in FIG. 49 or 50, a travel environment is associated with a frequency or a condition parameter of an unsafe posture which is the driver condition. Therefore, driver condition estimating unit 1204 may estimate the unsafe posture or the condition parameter of the unsafe posture as a driver condition of the driver to be estimated.

When the unsafe posture is estimated as a driver condition, vehicle controller 1206 determines that the unsafe posture is dangerous. When the condition parameter of an unsafe posture is estimated as a driver condition, vehicle controller 1206 determines whether or not the unsafe posture is dangerous based on the numerical value of the condition parameter. When determining that the unsafe posture is dangerous, vehicle controller 1206 executes the above-mentioned warning process as the danger avoidance process.

Thus, before the driver takes an unsafe posture while performing a lane change, for example, a warning sound or the like can be output, whereby the unsafe posture of the driver to be estimated can be prevented in advance.

[Loss of Consciousness]

For example, in the driver model constructed based on the travel environment illustrated in FIG. 49 or 50, a travel environment is associated with a frequency or a condition parameter of loss of consciousness which is the driver condition. Therefore, driver condition estimating unit 1204 may estimate loss of consciousness or the condition parameter of the loss of consciousness as a driver condition of the driver to be estimated.

When loss of consciousness is estimated as a driver condition, vehicle controller 1206 determines that the loss of consciousness is dangerous. When the condition parameter of loss of consciousness is estimated as a driver condition, vehicle controller 1206 determines whether or not the loss of consciousness is dangerous based on the numerical value of the condition parameter. When determining that the loss of consciousness is dangerous, vehicle controller 1206 executes the above-mentioned warning process as the danger avoidance process.

Thus, before the driver to be estimated loses consciousness, a warning sound or the like can be output, whereby the loss of consciousness can be prevented in advance.

It is to be noted that, if a chronic disease of the driver is associated with a travel environment in the driver model, a driver condition according to the chronic disease and the travel environment can be estimated. Such a chronic disease can be included in the driver model by an input operation performed by the driver.

[Summary of Sixth Exemplary Embodiment]

As described above, information processing system 1200 according to the sixth exemplary embodiment is an information processing system including at least one processor, wherein the at least one processor models, based on a degree of similarity among individual travel histories of a plurality of drivers, individual travel histories of at least one or more drivers from among the individual travel histories of the plurality of drivers to construct a driver model indicating a relationship between conditions of at least one or more drivers and travel environments of at least one or more vehicles. Note that the at least one processor has a function of modeling unit 1202.

According to this configuration, the driver model indicating the relationship between the condition of the driver (that is, driver condition) and the travel environment of the vehicle is constructed, whereby the condition of the driver can be estimated from the travel environment of vehicle 1 by using this driver model.

For example, information processing system 1200 may further include environment acquisition unit 1203 that acquires a travel environment of a driver to be estimated. The at least one processor may estimate a condition of a driver associated with a travel environment acquired by environment acquisition unit 1203 in the constructed driver model as a condition of the driver to be estimated. Note that, in this case, the at least one processor has a function of driver condition estimating unit 1204.

Information processing system 1200 may further include notification unit 1205 that provides notification to the driver to be estimated. The at least one processor may further determine whether or not the estimated condition of the driver to be estimated is dangerous. When determining that the estimated condition is dangerous, the at least one processor may execute a danger avoidance process for causing notification unit 1205 to provide information for avoiding danger to the driver to be estimated. Note that, in this case, the at least one processor has a function of vehicle controller 1206.

According to this configuration, if the estimated condition of the driver to be estimated is dangerous, information for avoiding the danger is presented to the driver, whereby the danger can be avoided in advance.

For example, the at least one processor may estimate a gaze direction of the driver to be estimated as a condition of the driver. When the estimated gaze is not directed to an advancing direction of the vehicle, the at least one processor may determine that the estimated gaze is dangerous, and execute the danger avoidance process. Accordingly, notification unit 1205 issues a warning to the driver to be estimated.

Thus, visual distraction of the driver can be avoided in advance, for example.

Further, the at least one processor may estimate an intensity level of drowsiness of the driver to be estimated as a condition of the driver. When the estimated intensity level of drowsiness is higher than a threshold, the at least one processor may determine that the estimated intensity level is dangerous, and execute the danger avoidance process. Accordingly, notification unit 1205 plays predetermined music, for example, high tempo music.

Thus, the driver can be prevented in advance from dozing off.

Further, the at least one processor may estimate a heart rate of the driver to be estimated as a condition of the driver. When the estimated heart rate is higher than a threshold, the at least one processor may determine that the estimated heart rate is dangerous, and execute the danger avoidance process. Accordingly, notification unit 1205 changes a currently displayed travel route of the vehicle.

Thus, an elevation of the heart rate of the driver can be suppressed in advance by making a detour around a road having heavy traffic, for example.

Further, the at least one processor may estimate a posture of the driver to be estimated as a condition of the driver. When the estimated posture is a predetermined posture, the at least one processor may determine that the estimated posture is dangerous, and execute the danger avoidance process. Accordingly, notification unit 1205 issues a warning to the driver to be estimated.

Thus, a dangerous posture of the driver, such as a posture while the driver searches a baggage on a passenger seat, can be avoided in advance, for example.

(Modification)

The travel histories in FIGS. 49 and 50 indicate a travel environment and a driver condition in association with each other. However, a behavior may further be associated with the travel environment and the driver condition.

Figure 52:
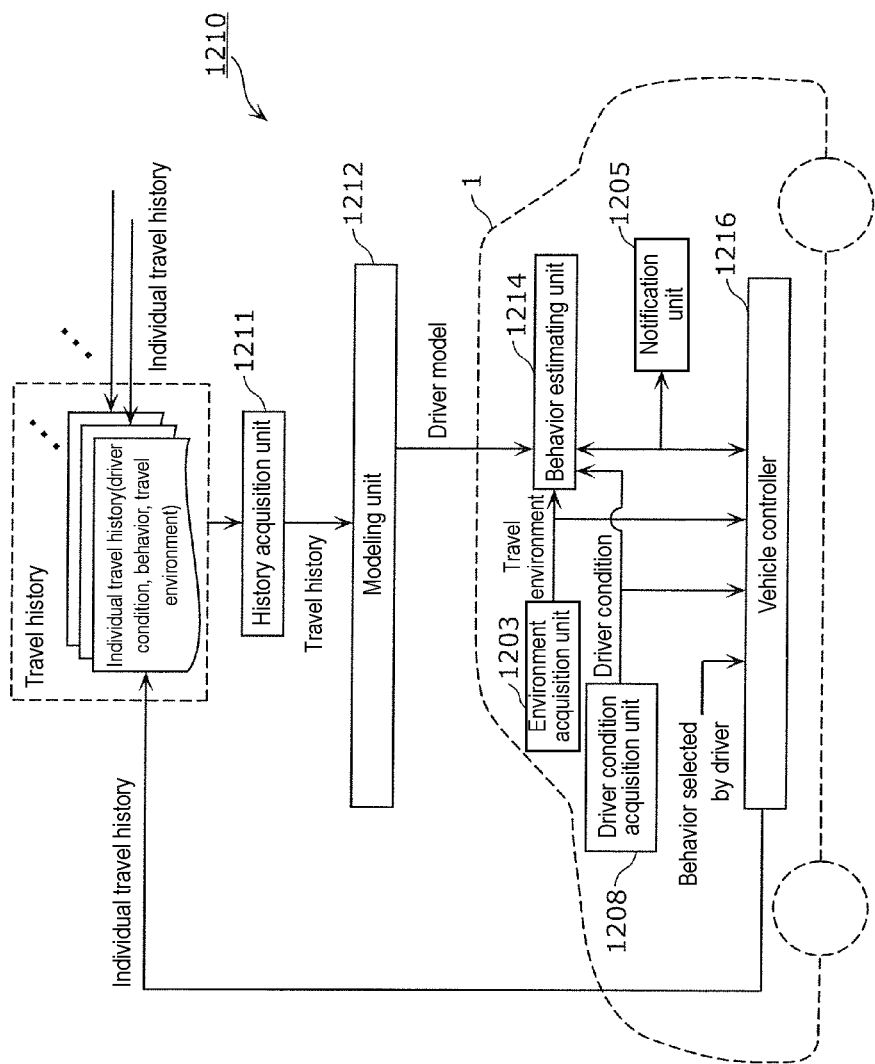
FIG. 52 is a block diagram illustrating a configuration of an information processing system according to a modification of the sixth exemplary embodiment.

FIG. 52 is a block diagram illustrating a configuration of an information processing system according to a modification of the sixth exemplary embodiment.

Information processing system 1210 is provided with history acquisition unit 1211 and modeling unit 1212. These components are disposed in a server, for example.

History acquisition unit 1211 acquires individual travel histories of each of a plurality of drivers including an individual travel history of a driver to be estimated who is driving vehicle 1. The individual travel history indicates, for each of travel environments and driver conditions that the vehicle driven by the driver encounters, the travel environment and the driver condition in association with a behavior of vehicle 1 selected by the driver to be estimated after a lapse of a predetermined time from the time at which the vehicle encounters the travel environment and the driver condition. History acquisition unit 1211 then outputs a travel history including the acquired individual travel histories of each of the plurality of drivers to modeling unit 1212.

Modeling unit 1212 acquires the travel history from history acquisition unit 1211, and models the individual travel histories of at least one or more drivers from among the individual travel histories of the plurality of drivers based on a degree of similarity among the individual travel histories of the plurality of drivers included in the travel history. A driver model is constructed by such a modeling process. Specifically, modeling unit 1212 performs the modeling process described above to construct a driver model indicating a relationship among driver conditions of at least one or more drivers, travel environments of at least one or more vehicles, and behaviors of at least one or more vehicles.

The driver model constructed by modeling unit 1212 may be a clustering-type driver model or an individually-adapted type driver model as described above. Specifically, the driver model is a model constructed from an individual travel history of at least one driver which is similar to the individual travel history of the driver to be estimated.

In this way, modeling unit 1212 according to the present modification constructs the driver model by further using the behavior selected by a user.

Information processing system 1210 is further provided with environment acquisition unit 1203, behavior estimating unit 1214, vehicle controller 1216, driver condition acquisition unit 1208, and notification unit 1205. These components are disposed in vehicle 1, for example.

Behavior estimating unit 1214 acquires the driver model constructed by modeling unit 1212. Behavior estimating unit 1214 estimates a behavior of vehicle 1 driven by the driver to be estimated by using the driver model, the current travel environment acquired by environment acquisition unit 1203, and the current driver condition acquired by driver condition acquisition unit 1208. That is, behavior estimating unit 1214 estimates a behavior associated with a travel environment and a driver condition most similar to the current travel environment and the driver condition which have been acquired in the driver model as a behavior of vehicle 1 driven by the driver to be estimated.

Vehicle controller 1216 generates an individual travel history. Specifically, vehicle controller 1216 acquires a travel environment from environment acquisition unit 1203, and acquires a driver condition from driver condition acquisition unit 1208. Then, vehicle controller 1216 generates an individual travel history indicating the travel environment and the driver condition being in association with a behavior selected by the driver after a lapse of a predetermined time from the time at which the travel environment and the driver condition are acquired.

Vehicle controller 1216 transmits the individual travel history to a server, for example. History acquisition unit 1211 described above acquires the individual travel history transmitted from vehicle controller 1216 as one individual travel history included in the travel history.

FIG. 53 is a diagram illustrating one example of a travel history according to the modification of the sixth exemplary embodiment.

As illustrated in FIG. 53, for example, the travel history in the present modification indicates a travel environment by using a plurality of environmental parameters and indicates a driver condition by using a plurality of condition parameters, as in the travel history in FIG. 50. The travel history indicates, for each of combinations of a travel environment and a driver condition, the combination and a behavior selected by the user in the combination, in association with each other. It is to be noted that, similar to the travel history illustrated in FIG. 49, the travel history according to the present modification may indicate a frequency of occurrence of at least one predetermined dangerous driver condition for each of a plurality of travel environments. That is, the travel history indicates, for each of combinations of a travel environment and each frequency of at least one dangerous driver condition, the combination and a behavior selected by the driver in the combination, in association with each other.

When a behavior is estimated by behavior estimating unit 1214, vehicle controller 1216 according to the present modification controls vehicle 1 such that vehicle 1 executes the estimated behavior. Alternatively, vehicle controller 1216 causes notification unit 1205 to provide the estimated behavior.

As described above, in information processing system 1210 according to the present modification, at least one processor constructs a driver model indicating a relationship among conditions of at least one or more drivers, travel environments of at least one or more vehicles, and behaviors of at least one or more vehicles, when constructing a driver model. Then, at least one processor estimates a behavior of a vehicle associated with a travel environment acquired by environment acquisition unit 1203 and a condition of a driver to be estimated under the acquired travel environment in the constructed driver model as a behavior of vehicle 1 driven by the driver to be estimated. Note that at least one processor has a function of modeling unit 1212 and a function of behavior estimating unit 1214.

In this way, in information processing system 1210 according to the present modification, a driver model is constructed by further using a behavior selected by a driver, and a behavior of vehicle 1 driven by the driver to be estimated is estimated by using the constructed driver model. On the other hand, in the fourth and fifth exemplary embodiments described above, a driver condition is not used in constructing a driver model. However, in information processing system 1210 according to the present modification, a driver model is constructed by using a driver condition as well as a travel environment and a behavior. Therefore, a behavior of vehicle 1 can be estimated with more accuracy based on the travel environment and the driver condition.

It should be noted that, while information processing system 1210 in the present modification is not provided with driver condition estimating unit 1204 in the sixth exemplary embodiment, information processing system 1210 may be provided with driver condition estimating unit 1204. In addition, vehicle controller 1216 may have the function of vehicle controller 1206 in the sixth exemplary embodiment. According to this configuration, information processing system 1210 can estimate a driver condition, and execute a danger avoidance process in response to the estimated driver condition, and besides, it can estimate a behavior of vehicle 1, and cause vehicle 1 to execute the estimated behavior.

In the sixth exemplary embodiment and the present modification, history acquisition units 1201 and 1211 and modeling units 1202 and 1212 are disposed in a server. However, all of or some of these units may be disposed in vehicle 1. Similarly, while driver condition estimating unit 1204, behavior estimating unit 1214, and vehicle controllers 1206 and 1216 are disposed in vehicle 1 in the sixth exemplary embodiment and in the present modification, functions of all of or some of these units may be disposed in a server.

While the exemplary embodiments according to the present invention have been described above with reference to the drawings, the functions of the above-mentioned devices and processing units can be implemented by a computer program.

A computer achieving the above-mentioned functions through execution of a program is provided with an input device such as a keyboard, a mouse, or a touch pad, an output device such as a display or a speaker, a processor, or a central processing unit (CPU), a read only memory (ROM), a random access memory (RAM). The computer is also provided with a storage device such as a hard disk drive or a solid state drive (SSD), a reading device for reading information from a recording medium such as a digital versatile disk read only memory (DVD-ROM) or a universal serial bus (USB) memory, a network card that performs communication through a network, and the like. The respective components are interconnected with a bus.

The reading device reads the program from the recording medium having the program recorded thereon, and the storage device stores the program. Alternatively, the network card performs communication with a server device connected to a network, and a program, downloaded from the server device, for achieving the functions of the respective devices is stored in the storage device.

Then, the processor or the CPU copies the program stored in the storage device on the RAM, sequentially reads commands included in the program from the RAM, and executes the read commands, whereby the functions of the respective devices are achieved.

INDUSTRIAL APPLICABILITY

The information processing system, information processing method, and program according to the present invention are applicable to a device or a system that processes information pertaining to driving of vehicles.

REFERENCE MARKS IN THE DRAWINGS

1: vehicle
2: brake pedal
3: accelerator pedal
4: indicator lever
5: steering wheel
6: detector
7, 1006: vehicle controller
8: storage unit
9: information notification device
10: touch panel
29a to 29c, 29g, 39a to 39c, 39g, 59a to 59c, 59g, 69a, 69c, 69g, 79a, 79c, 79g, 89a to 89c, 89g, 99b, 99c, 99g, 109a to 109d, 109e, 109g, 121, 121a to 121d: display region
51: operating unit
51a to 51h: operation button
59, 69, 79, 89, 99: character information
91: information acquisition unit
92, 1008: notification unit
101, 1005: display
102: input unit
109: display
111, 112, 113, 114, 121, 121', 122, 122', 123, 131, 131', 132, 133, 134, 134', 135 to 137, 231, 232, 233, 233', 234, 234', 235, 251, 251', 252, 252', 253, 261, 262, 263, 264, 265, 266, 267, 268: symbol
291: communication unit
292: cache
301: host vehicle
302: adjacent leading vehicle
303: detected surrounding condition
304: primary cache
305: secondary cache
1000: information processing system
1001: history acquisition unit
1002: modeling unit
1003: environment acquisition unit
1004: behavior estimating unit
1007: characteristic acquisition unit

The invention claimed is:
1. An information processing system comprising at least one processor,
wherein the at least one processor models, based on a degree of similarity among individual travel histories of a plurality of drivers, individual travel histories of at least one or more drivers from among the individual travel histories of the plurality of drivers to construct a driver model indicating a relationship between driver conditions of the at least one or more drivers and travel environments of at least one or more vehicles.

2. The information processing system according to claim 1, further comprising an environment acquisition circuit that acquires a travel environment of a vehicle driven by a driver, whose driving behavior is to be estimated,
wherein the at least one processor further estimates a driver condition associated with the travel environment acquired by the environment acquisition circuit, from among the driver conditions of the at least one or more drivers, in the driver model as a condition of the driver.

3. The information processing system according to claim 2, further comprising a notification circuit that provides notification to the driver,
wherein the at least one processor further determines whether or not the estimated condition of the driver is dangerous, and when determining that the estimated condition of the driver is dangerous, the at least one processor executes a danger avoidance process for causing the notification circuit to provide information for avoiding danger to the driver.

4. The information processing system according to claim 3, wherein the at least one processor estimates a direction of a gaze of the driver as the condition of the driver, and when an estimated gaze is not directed to an advancing direction of the vehicle driven by the driver, the at least one processor determines that the estimated gaze is dangerous, and executes the danger avoidance process to cause the notification circuit to issue a warning to the driver.

5. The information processing system according to claim 3, wherein the at least one processor estimates an intensity level of drowsiness of the driver as the condition of the driver, and when an estimated intensity level of drowsiness is higher than a threshold, the at least one processor determines that the estimated intensity level of drowsiness is dangerous, and executes the danger avoidance process to cause the notification circuit to play predetermined music.

6. The information processing system according to claim 3, wherein
the notification circuit provides a display of a travel route of the vehicle driven by the driver, and
the at least one processor estimates a heart rate of the driver as the condition of the driver, and when an estimated heart rate is higher than a threshold, the at least one processor determines that the estimated heart rate is dangerous, and executes the danger avoidance process to cause the notification circuit to change the travel route of the vehicle to a travel route for avoiding danger.

7. The information processing system according to claim 3, wherein the at least one processor estimates a posture of the driver as the condition of the driver, and when the estimated posture is a predetermined posture, the at least one processor determines that the estimated posture is dangerous, and executes the danger avoidance process to cause the notification circuit to issue a warning to the driver.

8. The information processing system according to claim 1, wherein,
in constructing the driver model,
the at least one processor
constructs the driver model indicating a relationship among the driver conditions of the at least one or more drivers, the travel environments of the at least one or more vehicles, and behaviors of the at least one or more vehicles, and
estimates a behavior of a vehicle associated with the travel environment of the vehicle driven by a driver, whose driving behavior is to be estimated and the condition of the driver in the driver model as a behavior of the vehicle driven by the driver.

9. An information processing method, comprising modeling, based on a degree of similarity among individual travel histories of a plurality of drivers, individual travel histories of at least one or more drivers from among the individual travel histories of the plurality of drivers to construct a driver model indicating a relationship between driver conditions of the at least one or more drivers and travel environments of at least one or more vehicles.

10. A non-transitory readable medium having instructions, the instructions including instructions that cause a processor to perform modeling, based on a degree of similarity among individual travel histories of a plurality of drivers, individual travel histories of at least one or more drivers from among the individual travel histories of the plurality of drivers to construct a driver model indicating a relationship between driver conditions of the at least one or more drivers and travel environments of at least one or more vehicles.

11. The information processing system according to claim 4, wherein the at least one processor estimates an intensity level of drowsiness of the driver as the condition of the driver, and when an estimated intensity level of drowsiness is higher than a threshold, the at least one processor determines that the estimated intensity level of drowsiness is dangerous, and executes the danger avoidance process to cause the notification circuit to play predetermined music.

* * * * *